US010308591B2

(12) United States Patent
Wainer et al.

(10) Patent No.: US 10,308,591 B2
(45) Date of Patent: Jun. 4, 2019

(54) PREPARATION OF (R,R)-FENOTEROL AND (R,R)- OR (R,S)-FENOTEROL ANALOGUES AND THEIR USE IN TREATING CONGESTIVE HEART FAILURE

(71) Applicant: The United States of America, as represented by the Secretary, Department of Health and Human Services, Washington, DC (US)

(72) Inventors: Irving William Wainer, Washington, DC (US); Weizhong Zhu, Philadelphia, PA (US); Khalid Chakir, Baltimore, MD (US); Rui-Ping Xiao, Baltimore, MD (US); Darrell R. Abernethy, Annapolis, MD (US); Farideh M. Beigi Abhari, Durham, NC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/874,747

(22) Filed: Jan. 18, 2018

(65) Prior Publication Data
US 2018/0141894 A1 May 24, 2018

Related U.S. Application Data

(60) Division of application No. 15/347,354, filed on Nov. 9, 2016, now Pat. No. 9,908,841, which is a continuation of application No. 14/199,208, filed on Mar. 6, 2014, now Pat. No. 9,522,871, which is a division of application No. 13/333,866, filed on Dec. 21, 2011, now Pat. No. 8,703,826, which is a continuation of application No. 12/376,945, filed as application No. PCT/US2007/075731 on Aug. 10, 2007, now abandoned.

(60) Provisional application No. 60/927,825, filed on May 3, 2007, provisional application No. 60/837,161, filed on Aug. 10, 2006.

(51) Int. Cl.
C07C 215/60 (2006.01)
(52) U.S. Cl.
CPC .................................. C07C 215/60 (2013.01)
(58) Field of Classification Search
None
See application file for complete search history.

(56) References Cited

U.S. PATENT DOCUMENTS

| 3,341,593 A | 9/1967 | Zeile et al. |
| 3,966,814 A | 6/1976 | Schromm et al. |
| 5,795,564 A | 8/1998 | Aberg et al. |
| 6,015,837 A | 1/2000 | Etlinger et al. |
| 6,589,508 B1 | 7/2003 | Aberg et al. |
| 6,664,424 B2 | 12/2003 | Booth et al. |
| 6,747,043 B2 | 6/2004 | Moran et al. |
| 6,866,839 B2 | 3/2005 | Aberg et al. |
| 7,045,658 B2 | 5/2006 | Biggadike et al. |
| 2002/0132830 A1 | 9/2002 | Morley |
| 2004/0192783 A1 | 9/2004 | Morley |
| 2005/0107417 A1 | 5/2005 | Germeyer et al. |
| 2005/0131072 A1 | 6/2005 | Aberg et al. |

FOREIGN PATENT DOCUMENTS

| CA | 959497 | * 12/1974 | ................... 260/340 |
| GB | 1 031 368 | 6/1966 | |
| GB | 1 283 632 | 8/1972 | |
| GB | 1 350 968 | 4/1974 | |
| GB | 1 360 658 | 7/1974 | |
| JP | 05097707 | 4/1993 | |
| JP | 5302194 | 6/2013 | |
| WO | WO 98/01099 | 1/1998 | |
| WO | WO 99/16430 | 4/1999 | |
| WO | WO 00/18389 | 4/2000 | |
| WO | WO 2005/042486 A1 | 5/2005 | |
| WO | WO 2005/092333 | 10/2005 | |
| WO | WO 2006/015830 A1 | 2/2006 | |
| WO | WO 2006/074897 | 7/2006 | |

OTHER PUBLICATIONS

Wong et al (Lancet 336:1396-1399, 1990—Abstract only) (Year: 1990).*
Irmer et al (Klin Wochenschr 59:639-645, 1981—Abstract only) (Year: 1981).*
Andersson, "Some new positive inotropic agents," *Acta Med Scand Suppl*. 707:65-73, 1986 (Abstract only).
Bryan et al., "Demonstration of Catecholamine and Resorcinolamine Derivatives as Formaldehyde-Induced Fluorescence in Protein Models," Journal of Histochemistry and Cytochemistry, vol. 36, No. 6, pp. 615-620, 1988.
Examination Report issued by the Australian Patent Office, dated Apr. 30, 2013, for corresponding Australian Patent Application No. 2013202127, 4 pp.
Examination Report issued by the Canadian Intellectual Property Office, dated Apr. 16, 2013, for corresponding Canadian Patent Application No. 2,660,707, 5 pp.

(Continued)

*Primary Examiner* — Craig D Ricci
(74) *Attorney, Agent, or Firm* — Klarquist Sparkman, LLP

(57) ABSTRACT

This disclosure concerns the discovery of (R,R)- and (R,S)-fenoterol analogs which are highly effective at binding β2-adrenergic receptors. Exemplary chemical structures for these analogs are provided. Also provided are pharmaceutical compositions including the disclosed (R,R)-fenoterol and fenoterol analogs, and methods of using such compounds and compositions for the treatment of cardiac disorders such as congestive heart failure and pulmonary disorders such as asthma or chronic obstructive pulmonary disease.

4 Claims, 9 Drawing Sheets

(56) References Cited

OTHER PUBLICATIONS

Gleiter, "Fenoterol: Pharmacology and Clinical Use," *Cardiovascular Drug Reviews*, vol. 17, No. 1, pp. 87-106, 1999.
International Search Report dated Jan. 30, 2008 from International Application No. PCT/US2007/075731.
Irmer et al., "Treatment of severe congestive heart failure with the beta-agonist fenoterol," *Klin Wochenschr*. 59(12):639-645, Jun. 15, 1981 (Abstract only).
Jozwiak et al., "Comparative Molecular Field Analysis of the Binding of the Stereoisomers of Fenoterol and Fenoterol Derivatives to the $\beta_2$ Adrenergic Receptor," *J. Med. Chem.* 50(12):2903-2915, 2007.
Kaiser et al., "Identification and Quantification of β-Adrenoceptor Sites in Red Blood Cells from Rats," *Archives of Pharmacology* 305:41-50, 1978.
Lin et al., "Separation of enantiomers of drugs by capillary electrophoresis. Part 8. B-Cyclodextrin as chiral solvating agent," *Talanta*, 46(4), pp. 743-749, 1998.
Mugge et al., "Effects of the beta 2-adrenoceptor agonists fenoterol and salbutamol on force of contraction in isolated human ventricular myocardium," *Klin Wochenschr*. 63(1):26-31, Jan. 2, 1985 (Abstract only).
Notice of Reasons for Rejection (with English-language translation) issued by the Japanese Patent Office dated Sep. 24, 2012, for corresponding Japanese Patent Application No. 2009-524015, 3 pp.
Notice of Reasons for Rejection (with English-language translation) issued by the Japanese Patent Office dated Aug. 13, 2014, for corresponding Japanese Patent Application No. 2013-129406.

Patent Examination Report No. 1 issued by the Australian Patent Office dated Aug. 7, 2015, for corresponding Australian Divisional Patent Application No. 2014224073.
Perrin et al., "Rapid screening for chiral separations by short-end injection capillary electrophoresis using highly sulfated cyclodextrins as chiral selectors," *Electrophoresis*, 22(15), pp. 3203-3215, 2001.
Rominger et al., "Radioimmunoligical Determination of Fenoterol Part II: Antiserum and tracer for the determination of fenoterol," *Drug Research*, 40 (11) No. 8, 1990.
Rominger et al., "Radioimmunological determination of fenoterol part ii, antiserum and tracer for the determination of fenoterol," *Arzneimittel Forschung*, 40(8): 887-895, 1990 (Abstract only).
Ryall et al., "$\beta_2$-Agonist fenoterol has greater effects on contractile function of rat skeletal muscles than clenbuterol," *Am J. Physiol Regul Integr Comp Physiol* 283:R1386-R1394, 2002.
Schirrmacher et al., "Synthesis and preliminary evaluation of (R,R)(S,S) 5-(2-(2-[4-(2-[18F]fluoroethoxy)phenyl]-1-methylethylamino)-1-hydroxyethyl)-benzene-1,3-diol (18F]FEFE) for the in vivo visualization and quanitification of the β2-adrenergic receptor status in lung," *Bioorganic & Medicinal Chemistry Letters*, 13 (16), pp. 2687-2692, 2003.
Williams, "Stereoisomerism and Chirality," *Stereochemistry Review*, Fall 2005.
Woo et al., "Stereochemistry of an Agonist Determines Coupling Preference of $\beta_2$-Adrenoceptor to Different G Proteins in Cardiomyocytes," *Molecular Pharmacology* 75(1):158-65, Jan. 2009.
Xiao et al., "Enhanced $G_i$ Signaling Selectively Negates $\beta_2$-Adrenergic Receptor (AR)- but Not β 1-AR-Mediated Positive Inotropic Effect in Myocytes From Failing Rat Hearts," *Circulation* pp. 1633-1639, Sep. 30, 2003.

* cited by examiner

| Compounds | R1 | R2 |
|---|---|---|
| 2 | CH₃ | 4-methoxyphenyl |
| 3 | CH₃ | phenyl |
| 4 | CH₃ | 4-aminophenyl |
| 5 | CH₃ | naphthyl |
| 6 | CH₃ | sec-butyl |
| 7 | H | phenyl |

47

48

49

50

51

PREPARATION OF (R,R)-FENOTEROL AND (R,R)- OR (R,S)-FENOTEROL ANALOGUES AND THEIR USE IN TREATING CONGESTIVE HEART FAILURE

CROSS REFERENCE TO RELATED APPLICATIONS

This application is a divisional of U.S. patent application Ser. No. 15/347,354, filed Nov. 9, 2016, now issued as U.S. Pat. No. 9,908,841, which is a continuation of U.S. patent application Ser. No. 14/199,208, filed Mar. 6, 2014, now issued as U.S. Pat. No. 9,522,871, which is a divisional of U.S. patent application Ser. No. 13/333,866, filed Dec. 21, 2011, now issued as U.S. Pat. No. 8,703,826, which is a continuation of U.S. patent application Ser. No. 12/376,945, filed Feb. 9, 2009, now abandoned, which is a § 371 U.S. National Stage of International Application No. PCT/US2007/075731, filed Aug. 10, 2007, which in turn claims the benefit of U.S. Provisional Patent Application No. 60/927,825, filed May 3, 2007, and U.S. Provisional Application No. 60/837,161, filed Aug. 10, 2006, all of which are incorporated herein in their entirety by reference.

FIELD

The present disclosure relates to the field of pharmaceutical compositions and in particular, to the preparation of (R,R)-fenoterol and (R,R)- or (R,S)-fenoterol analogues and their use in treating congestive heart failure.

BACKGROUND

Fenoterol, 5-[1-hydroxy-2[[2-(4-hydroxyphenyl)-1-methylethyl]-amino] ethyl]1,2-benzenediol, is a β2-adrenergic receptor agonist that has traditionally been used for the treatment of pulmonary disorders such as asthma. This drug has two chiral (asymmetric) carbons that can each be independently arranged in an R or S configuration, so that the drug exists in distinct (R,R), (R,S), (S,R) and (S,S) forms known as stereoisomers. Fenoterol is commercially available as a racemic mixture of the (R,R)- and (S,S)-compounds.

Fenoterol is known to act as an agonist that binds to and activates the β2-adrenergic receptor. This activity has led to its clinical use in the treatment of asthma because this agonist's activity dilates constricted airways. Additional therapeutic uses for fenoterol remain to be thoroughly explored. Pharmacological studies of the class of drugs that includes fenoterol have shown that only one of the enantiomers is responsible for generating brochodilation. For example, studies have demonstrated that the primary bronchodilatory activity for racemic (±)-fenoterol resides in the (R,R)-isomer of fenoterol. Further, it has recently become apparent that the inactive enantiomer may be associated with adverse effects. For instance, the diastereomer (S,S)-fenoterol has been demonstrated to cause adverse side effects or development of tolerance often associated with β2-adrenergic receptor agonist treatment.

It would therefore be advantageous to provide fenoterol compositions that were effective at treating disorders such as asthma, chronic obstructive pulmonary disease, or congestive heart failure, but had reduced side effects such as hypersensitivity and drug resistance (tolerance).

SUMMARY

This disclosure concerns the discovery of fenoterol analogues that are highly effective at binding β2-adrenergic receptors. Exemplary chemical structures for these analogues are provided throughout the disclosure. By way of example, such compounds are represented by the following general formula:

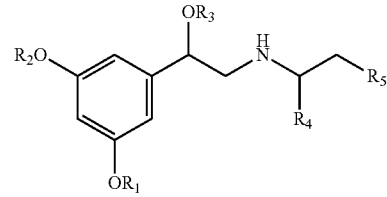

wherein $R_1$-$R_3$ independently are hydrogen, acyl, alkoxy carbonyl, amino carbonyl (carbamoyl) or a combination thereof;

$R_4$ is H or lower alkyl;

$R_5$ is lower alkyl,

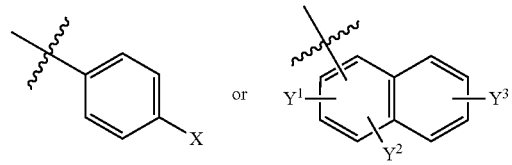

wherein X, $Y^1$, $Y^2$ and $Y^3$ independently are hydrogen, —$OR_6$ and —$NR_7R_8$;

$R_6$ is independently hydrogen, lower alkyl, acyl, alkoxy carbonyl or amino carbonyl; and $R_7$ and $R_8$ independently are hydrogen, lower alkyl, alkoxy carbonyl, acyl or amino carbonyl.

Pharmaceutical compositions containing, and methods of using (R,R)-fenoterol and fenoterol analogues are also provided. For example, the disclosed (R,R)-fenoterol and (R,R)- or (R,S)-fenoterol analogues (e.g., (R,R)-methoxyfenoterol, (R,R)-napthylfenoterol, and (R,S)-napthylfenoterol) are effective at treating cardiac disorders or pulmonary disorders.

The foregoing and other features and advantages will become more apparent from the following detailed description of several embodiments, which proceeds with reference to the accompanying figures.

DETAILED DESCRIPTION OF SEVERAL EMBODIMENTS

I. Introduction

Figure 1:
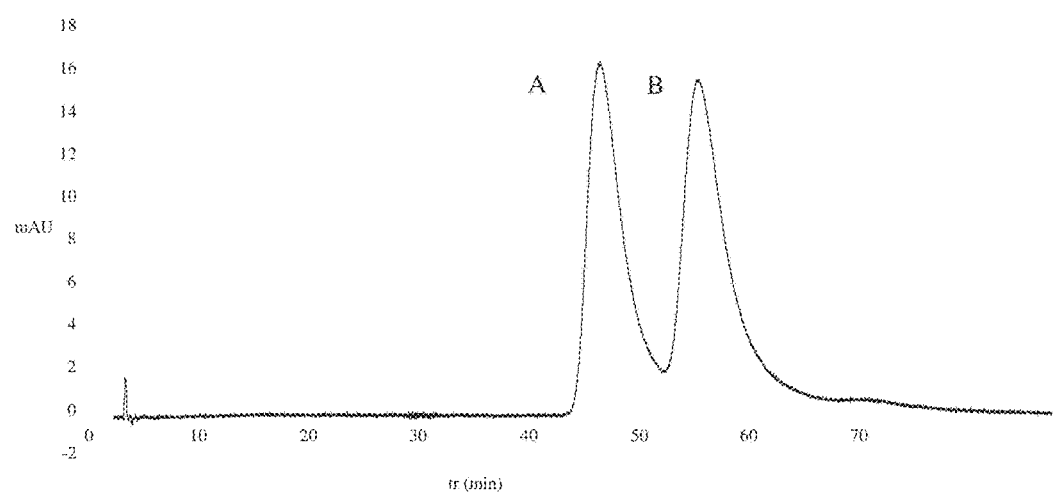
FIG. 1 illustrates the chromatographic separation of (S,S)- and (R,R)-fenoterol.

This disclosure provides fenoterol analogues that bind the β2-adrenergic receptor with comparable or greater activity than fenoterol. In one embodiment, the optically active fenoterol analogues are substantially purified from a racemic mixture. For example, an optically active fenoterol analogue is purified to represent greater than 90%, often greater than 95% of the composition. These analogues can be used to treat pulmonary disorders such as asthma and chronic obstructive pulmonary disease that have previously been treated with (±)-fenoterol. Use of the disclosed fenoterol analogues with an equal to higher efficacy than (±)-fenoterol can possibly reduce adverse effects previously observed with (±)-fenoterol. For example, use of a lower concentration of the fenoterol analogues to obtain a therapeutic effective response is expected to reduce side-effects such as hypersensitivity and drug resistance (tolerance) observed with the commercially available (±)-fenoterol. Also, purification of the analogues removes contaminants such as the inactive enantiomer which can be responsible for these adverse effects.

The present disclosure also demonstrates that (R,R)-fenoterol is the active component of commercially available (±)-fenoterol. It is specifically contemplated that (R,R)-fenoterol as well as disclosed (R,R)- and (R,S)-fenoterol analogues can be used to treat cardiac disorders such as congestive heart failure. Use of substantially optically pure (R,R)-fenoterol or (R,R)- or (R,S)-fenoterol analogues to treat congestive heart failure is expected to reduce the incidence of side-effects caused by physiologically less active forms of the drug.

II. Abbreviations and Terms

AR: adrenergic receptor
CD: circular dichroism
CoMFA: comparative molecular field analysis
HPLC: high performance liquid chromatography
IAM-PC: immobilized artificial membrane chromatographic support
ICYP: [$^{125}$I]cyanopindolol
UV: ultraviolet Unless otherwise explained, all technical and scientific terms used herein have the same meaning as commonly understood by one of ordinary skill in the art to which the disclosed subject matter belongs. Definitions of common terms in chemistry terms may be found in *The McGraw-Hill Dictionary of Chemical Terms*, 1985, and *The Condensed Chemical Dictionary*, 1981. As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Except as otherwise noted, any quantitative values are approximate whether the word "about" or "approximately" or the like are stated or not. The materials, methods, and examples described herein are illustrative only and not intended to be limiting. Any molecular weight or molecular mass values are approximate and are provided only for description. Except as otherwise noted, the methods and techniques of the present invention are generally performed according to conventional methods well known in the art and as described in various general and more specific references that are cited and discussed throughout the present specification. See, e.g., Loudon, *Organic Chemistry*, Fourth Edition, New York: Oxford University Press, 2002, pp. 360-361, 1084-1085; Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978.

In order to facilitate review of the various embodiments disclosed herein, the following explanations of specific terms are provided:

Acyl: A group of the formula RC(O)— wherein R is an organic group.

Acyloxy: A group having the structure —OC(O)R, where R may be an optionally substituted alkyl or optionally substituted aryl. "Lower acyloxy" groups are those where R contains from 1 to 10 (such as from 1 to 6) carbon atoms.

Alkoxy: A radical (or substituent) having the structure —O—R, where R is a substituted or unsubstituted alkyl. Methoxy (—OCH$_3$) is an exemplary alkoxy group. In a substituted alkoxy, R is alkyl substituted with a non-interfering substituent. "Thioalkoxy" refers to —S—R, where R is substituted or unsubstituted alkyl. "Haloalkyloxy" means a radical —OR where R is a haloalkyl.

Alkoxy carbonyl: A group of the formula —C(O)OR, where R may be an optionally substituted alkyl or optionally substituted aryl. "Lower alkoxy carbonyl" groups are those where R contains from 1 to 10 (such as from 1 to 6) carbon atoms.

Alkyl: An acyclic, saturated, branched- or straight-chain hydrocarbon radical, which, unless expressly stated otherwise, contains from one to fifteen carbon atoms; for example, from one to ten, from one to six, or from one to four carbon atoms. This term includes, for example, groups such as methyl, ethyl, n-propyl, isopropyl, isobutyl, t-butyl, pentyl, heptyl, octyl, nonyl, decyl, or dodecyl. The term "lower alkyl" refers to an alkyl group containing from one to ten carbon atoms. Unless expressly referred to as an "unsubstituted alkyl," alkyl groups can either be unsubstituted or substituted. An alkyl group can be substituted with one or more substituents (for example, up to two substituents for each methylene carbon in an alkyl chain). Exemplary alkyl substituents include, for instance, amino groups, amide, sulfonamide, halogen, cyano, carboxy, hydroxy, mercapto, trifluoromethyl, alkyl, alkoxy (such as methoxy), alkylthio, thioalkoxy, arylalkyl, heteroaryl, alkylamino, dialkylamino, alkylsulfano, keto, or other functionality.

Amino carbonyl (carbamoyl): A group of the formula —OCN(R)R'—, wherein R and R' are independently of each other hydrogen or a lower alkyl group.

Asthma: Asthma is a disease of the respiratory system in which the airways constrict, become inflamed, and are lined with excessive amounts of mucus, often in response to one or more "triggers," such as exposure to an environmental stimulant (or allergen), cold air, exercise, or emotional stress. This airway narrowing causes symptoms such as wheezing, shortness of breath, chest tightness, and coughing. The disorder is a chronic or recurring inflammatory condition in which the airways develop increased responsiveness to the various stimuli, characterized by bronchial hyper-responsiveness, inflammation, increased mucus production, and intermittent airway obstruction.

Carbamate: A group of the formula —OC(O)N(R)—, wherein R is H, or an aliphatic group, such as a lower alkyl group or an aralkyl group Cardiac Disorder or Disease: In general, a cardiac disorder/disease is a class of disorders/diseases that involve the heart and/or blood vessels (arteries and veins). In a particular example, cardiac disorder/disease includes congestive heart failure.

Chronic Obstructive Pulmonary Disease: A group of respiratory tract diseases including chronic bronchitis, emphysema and bronchiectasis that are characterized by airflow obstruction or limitation that is not fully reversible. The airflow limitation is usually progressive and associated with an abnormal inflammatory response of the lungs to noxious particles or gases.

Congestive Heart Failure: Heart failure in which the heart is unable to maintain an adequate circulation of blood in the bodily tissues or to pump out the venous blood returned to it by the veins.

Derivative: A chemical substance that differs from another chemical substance by one or more functional groups. Preferably, a derivative (such as a fenoterol analogue) retains a biological activity (such as β2-adrenergic receptor stimulation) of a molecule from which it was derived (such as a fenoterol).

Isomers: Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers, respectively). A chiral compound can exist as either an individual enantiomer or as a mixture thereof. A mixture containing equal proportions of the enantiomers is called a "racemic mixture."

The compounds described herein may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., March, *Advanced Organic Chemistry*, 4th edition, New York: John Wiley and Sons, 1992, Chapter 4).

Optional: "Optional" or "optionally" means that the subsequently described event or circumstance can but need not occur, and that the description includes instances where said event or circumstance occurs and instances where it does not.

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more therapeutic compounds or molecules, such as one or more nucleic acid molecules, proteins or antibodies that bind these proteins, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phenyl: Phenyl groups may be unsubstituted or substituted with one, two or three substituents, with substituent(s) independently selected from alkyl, heteroalkyl, aliphatic, heteroaliphatic, thioalkoxy, halo, haloalkyl (such as —$CF_3$), nitro, cyano, —OR (where R is hydrogen or alkyl), —N(R)R' (where R and R' are independently of each other hydrogen or alkyl), —COOR (where R is hydrogen or alkyl) or —C(O)N(R')R" (where R' and R" are independently selected from hydrogen or alkyl).

Pulmonary Disorder or Disease: In general, pulmonary disorder/disease includes any disorder/disease pertaining to the lungs. In a particular example, pulmonary disorder/disease includes asthma and chronic obstructive pulmonary disease.

Purified: The term "purified" does not require absolute purity; rather, it is intended as a relative term. Thus, for example, a purified preparation is one in which a desired component such as an (R,R)-enantiomer of fenoterol is more enriched than it was in a preceding environment such as in a (±)-fenoterol mixture. A desired component such as (R,R)-enantiomer of fenoterol is considered to be purified, for example, when at least about 70%, 80%, 85%, 90%, 92%, 95%, 97%, 98%, or 99% of a sample by weight is composed of the desired component. Purity of a compound may be determined, for example, by high performance liquid chromatography (HPLC) or other conventional methods. In an example, the specific fenoterol analogue enantiomers are purified to represent greater than 90%, often greater than 95% of the other enantiomers present in a purified preparation. In other cases, the purified preparation may be essentially homogeneous, wherein other stereoisomers are less than 1%.

Compounds described herein may be obtained in a purified form or purified by any of the means known in the art, including silica gel and/or alumina chromatography. See, e.g., *Introduction to Modern Liquid Chromatography*, 2nd Edition, ed. by Snyder and Kirkland, New York: John Wiley and Sons, 1979; and *Thin Layer Chromatography*, ed. by Stahl, New York: Springer Verlag, 1969. In an example, a compound includes purified fenoterol or fenoterol analogue with a purity of at least about 70%, 80%, 85%, 90%, 92%, 95%, 97%, 98%, or 99% of a sample by weight relative to other contaminants. In a further example, a compound includes at least two purified stereoisomers each with a purity of at least about 70%, 80%, 85%, 90%, 92%, 95%, 97%, 98%, or 99% of a sample by weight relative to other contaminants. For instance, a compound can include a substantially purified (R,R)-fenoterol analogue and a substantially purified (R,S)-fenoterol analogue.

Subject: The term "subject" includes both human and veterinary subjects, for example, humans, non-human primates, dogs, cats, horses, rats, mice, and cows. Similarly, the term mammal includes both human and non-human mammals.

Treating or treatment: With respect to disease, either term includes (1) preventing the disease, e.g., causing the clinical symptoms of the disease not to develop in a subject that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

Therapeutically Effective Amount: A quantity of a specified agent sufficient to achieve a desired effect in a subject being treated with that agent. For example, this may be the amount of (R,R)-fenoterol or (R,R)- or (R,S)-fenoterol analogue useful in preventing, reducing, and/or inhibiting, and/or treating a cardiac disorder such as congestive heart failure. Ideally, a therapeutically effective amount of an agent is an amount sufficient to prevent, reduce, and/or inhibit, and/or treat the disorder in a subject without causing a substantial cytotoxic effect in the subject. The effective amount of an agent useful for preventing, reducing, and/or inhibiting, and/or treating a disorder in a subject will be dependent on the subject being treated, the severity of the disorder, and the manner of administration of the therapeutic composition.

III. (R,R)-Fenoterol and Fenoterol Analogues

A. Chemical Structure

Some exemplary fenoterol analogues disclosed herein have the formula:

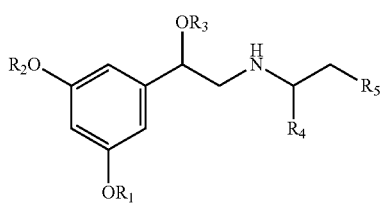

wherein $R_1$-$R_3$ independently are hydrogen, acyl, alkoxy carbonyl, amino carbonyl or a combination thereof;
$R_4$ is H or lower alkyl;
$R_5$ is lower alkyl,

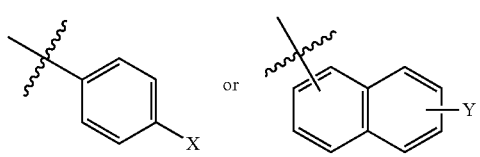

wherein X and Y independently are selected from hydrogen, lower —$OR_6$ and —$NR_7R_8$;
$R_6$ is lower alkyl or acyl; and
$R_7$ and $R_8$ independently are hydrogen, lower alkyl, alkoxy carbonyl, acyl or amino carbonyl.

With continued reference to the general formula for fenoterol analogues above, Y may be —OH In one embodiment, $R_5$ is a 1- or 2-napthyl derivative optionally having 1, 2 or 3 substituents. Examples of such $R_5$ groups are represented by the formula

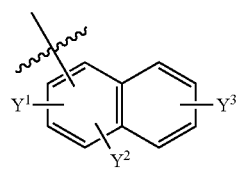

wherein $Y^1$, $Y^2$ and $Y^3$ independently are hydrogen, lower —$OR_6$ and —$NR_7R_8$;
$R_6$ is independently for each occurrence selected from lower alkyl and acyl; and
$R_7$ and $R_8$ independently are hydrogen, lower alkyl, alkoxy carbonyl, acyl or amino carbonyl (carbamoyl). In particular compounds at least one of $Y^1$, $Y^2$ and $Y^3$ is —$OCH_3$.

Particular $R_5$ groups include those represented by the formulas

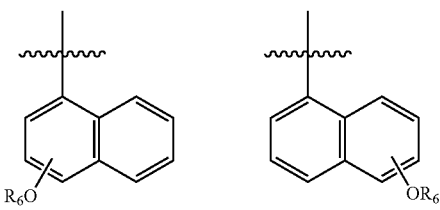

wherein $R_6$ is lower alkyl, such as methyl, ethyl, propyl or isopropyl or acyl, such as acetyl.

Exemplary $R_5$ groups include

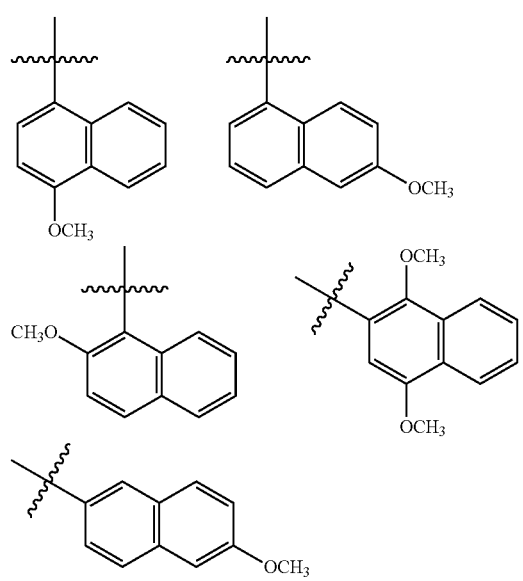

-continued

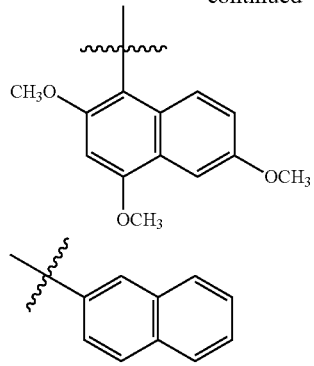

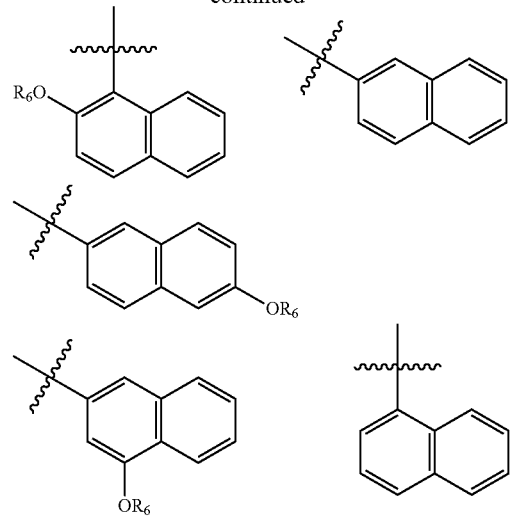

In one example, R$_4$ is lower alkyl and R$_5$ is

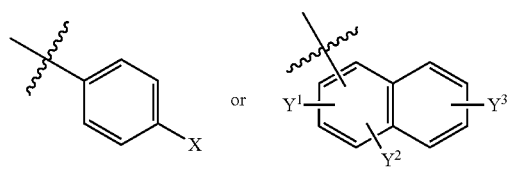

wherein X and Y independently are selected from H, lower alkyl —OR$_6$ and —NR$_7$R$_8$;
R$_6$ is lower alkyl; and
R$_7$ and R$_8$ independently are hydrogen or lower alkyl.
In a further example, R$_4$ is selected from ethyl, n-propyl, and isopropyl and R$_5$ has the formula

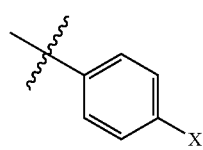

wherein X is H, —OR$_6$ or —NR$_7$R$_8$. For example, R$_6$ may be methyl or R$_7$ and R$_8$ are hydrogen.
In an additional example, R$_5$ has the formula

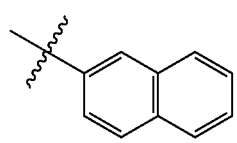 [SMILES: *c1ccc2ccccc2c1]

In further embodiments, R$_4$ is selected from methyl, ethyl, n-propyl and isopropyl and R$_5$ represents

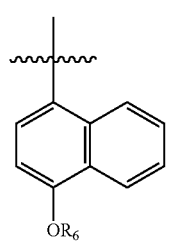

Examples of suitable groups for R$_1$-R$_3$ that can be cleaved in vivo to provide a hydroxy group include, without limitation, acyl, acyloxy and alkoxy carbonyl groups. Compounds having such cleavable groups are referred to as "prodrugs." The term "prodrug," as used herein, means a compound which includes a substituent that is convertible in vivo (e.g., by hydrolysis) to a hydroxyl group. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed), *Design and Application of Prodrugs, Textbook of Drug Design and Development*, Chapter 5, 113 191 (1991); Bundgaard, et al., *Journal of Drug Delivery Reviews*, 8:1 38 (1992); Bundgaard, *Pharmaceutical Sciences*, 77:285 et seq. (1988); and Higuchi and Stella (eds.) *Prodrugs as Novel Drug Delivery Systems*, American Chemical Society (1975).

An exemplary (R,R)-compound has the chemical structure of:

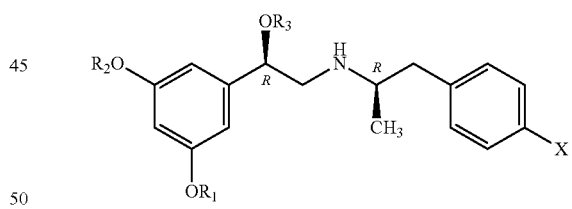

X and R$_1$-R$_3$ are as described above.
An additional exemplary (R,R)-compound has the chemical structure:

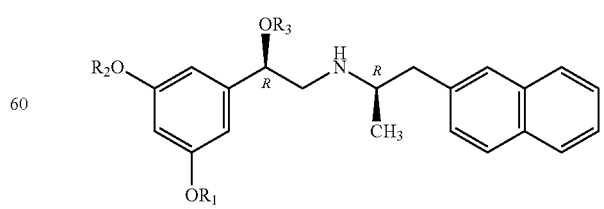

An exemplary (R,S)-compound has the chemical structure:

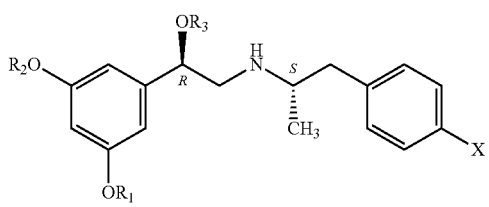

wherein X and $R_1$-$R_3$ are as described above.

An additional exemplary (R,S)-compound has the chemical structure:

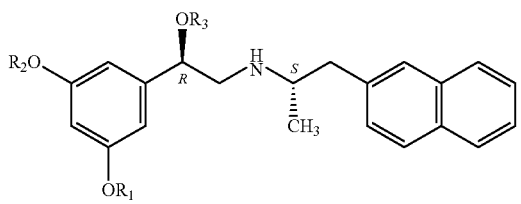

An exemplary (S,R)-compound has the chemical structure:

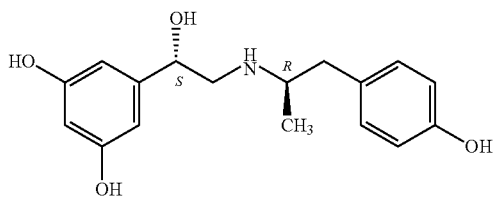

wherein X and $R_1$-$R_3$ are as described above.

An exemplary (S,S)-compound has the chemical structure:

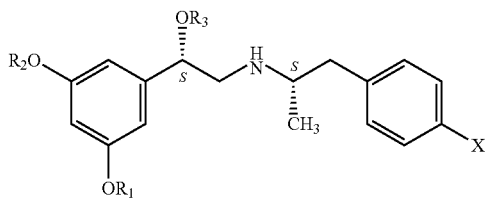

wherein X and $R_1$-$R_3$ are as described above.

Examples of chemical structures illustrating the various stereoisomers of fenoterol are provided below.

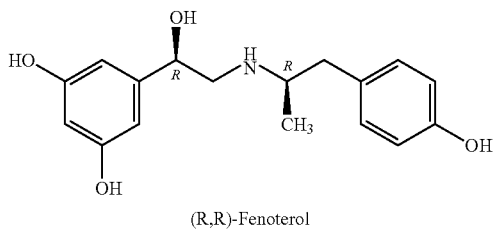

(R,R)-Fenoterol

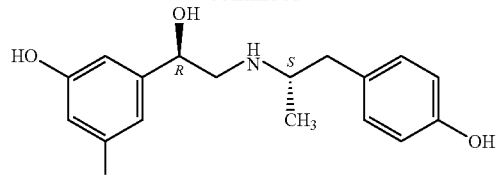

(R,S)-Fenoterol

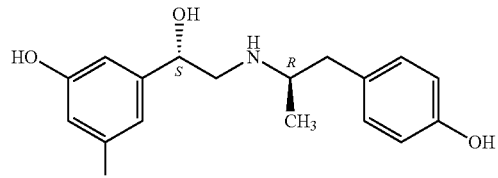

(S,R)-Fenoterol

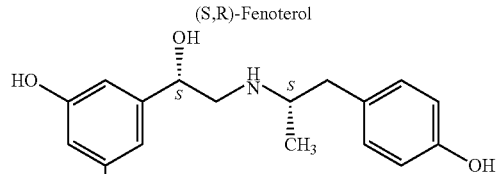

(S,S)-Fenoterol

Particular method embodiments contemplate the use of solvates (such as hydrates), pharmaceutically acceptable salts and/or different physical forms of (R,R)-fenoterol or any of the fenoterol analogues herein described.

1. Solvates, Salts and Physical Forms

"Solvate" means a physical association of a compound with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compound, methanol associated compounds, and the like. "Hydrate" is a solvate wherein the solvent molecule(s) is/are $H_2O$.

The disclosed compounds also encompass salts including, if several salt-forming groups are present, mixed salts and/or internal salts. The salts are generally pharmaceutically-acceptable salts that are non-toxic. Salts may be of any type (both organic and inorganic), such as fumarates, hydrobromides, hydrochlorides, sulfates and phosphates. In an example, salts include non-metals (e.g., halogens) that form group VII in the periodic table of elements. For example, compounds may be provided as a hydrobromide salt.

Additional examples of salt-forming groups include, but are not limited to, a carboxyl group, a phosphonic acid group or a boronic acid group, that can form salts with suitable bases. These salts can include, for example, nontoxic metal cations which are derived from metals of groups IA, IB, IIA and IIB of the periodic table of the elements. In one embodiment, alkali metal cations such as lithium, sodium or potassium ions, or alkaline earth metal cations such as magnesium or calcium ions can be used. The salt can also be a zinc or an ammonium cation. The salt can also be formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts.

Exemplary compounds disclosed herein possess at least one basic group that can form acid-base salts with inorganic acids. Examples of basic groups include, but are not limited to, an amino group or imino group. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In a currently preferred embodiment, fenoterol is provided as a hydrobromide salt and exemplary fenoterol analogues are provided as their fumarate salts.

Additional counterions for forming pharmaceutically acceptable salts are found in *Remington's Pharmaceutical Sciences,* 19th Edition, Mack Publishing Company, Easton, Pa., 1995. In one aspect, employing a pharmaceutically acceptable salt may also serve to adjust the osmotic pressure of a composition.

In certain embodiments the compounds used in the method are provided are polymorphous. As such, the compounds can be provided in two or more physical forms, such as different crystal forms, crystalline, liquid crystalline or non-crystalline (amorphous) forms.

2. Use for the Manufacture of a Medicament

Any of the above described compounds (e.g., (R,R)-fenoterol or fenoterol analogues or a hydrate or pharmaceutically acceptable salt thereof) or combinations thereof are intended for use in the manufacture of a medicament for β2-adrenergic receptor stimulation in a subject or for the treatment of pulmonary and cardiac disorders (e.g., asthma and congestive heart failure). Formulations suitable for such medicaments, subjects who may benefit from same and other related features are described elsewhere herein.

B. Methods of Synthesis

The disclosed fenoterol analogues can be synthesized by any method known in the art. Many general references providing commonly known chemical synthetic schemes and conditions useful for synthesizing the disclosed compounds are available (see, e.g., Smith and March, *March's Advanced Organic Chemistry: Reactions, Mechanisms, and Structure,* Fifth Edition, Wiley-Interscience, 2001; or Vogel, *A Textbook of Practical Organic Chemistry, Including Qualitative Organic Analysis,* Fourth Edition, New York: Longman, 1978).

Compounds as described herein may be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via open column chromatography or prep chromatography.

Suitable exemplary syntheses of fenoterol analogues are provided below:

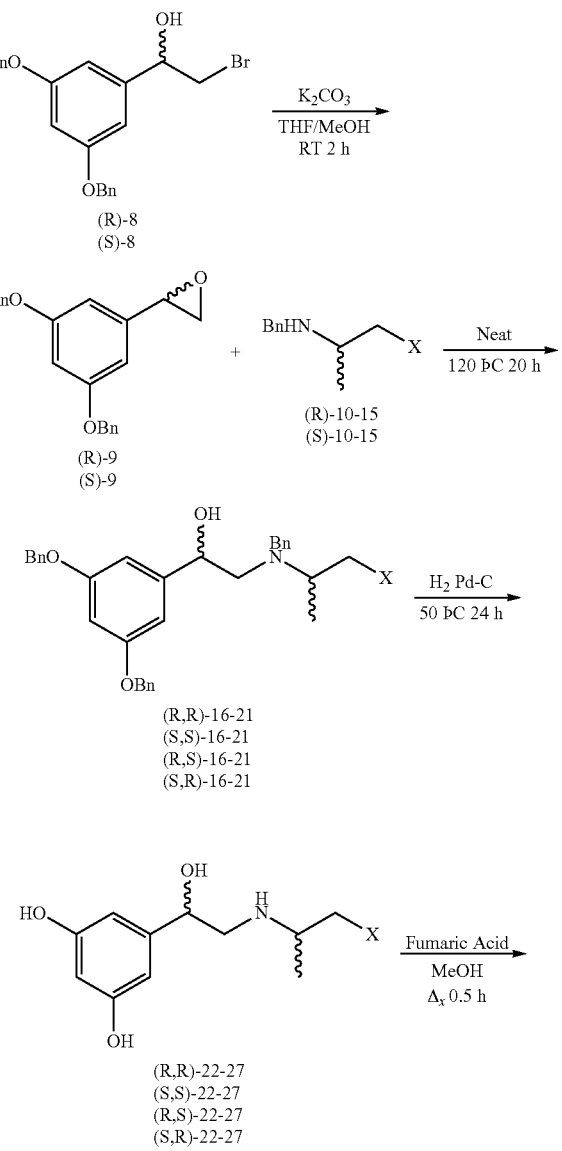

Scheme I: An exemplary synthesis of 4 stereoisomers of 1-6 including the coupling of the epoxide formed from either (R)- or (S)-3',5'-dibenzyloxyphenylbromohydrin with the (R)- or (S)-enantiomer of the appropriate benzyl-protected 2-amino-3-benzylpropane (1-5) or the (R) or (S)-enantiomer of N-benzyl-2-aminoheptane (6).

-continued

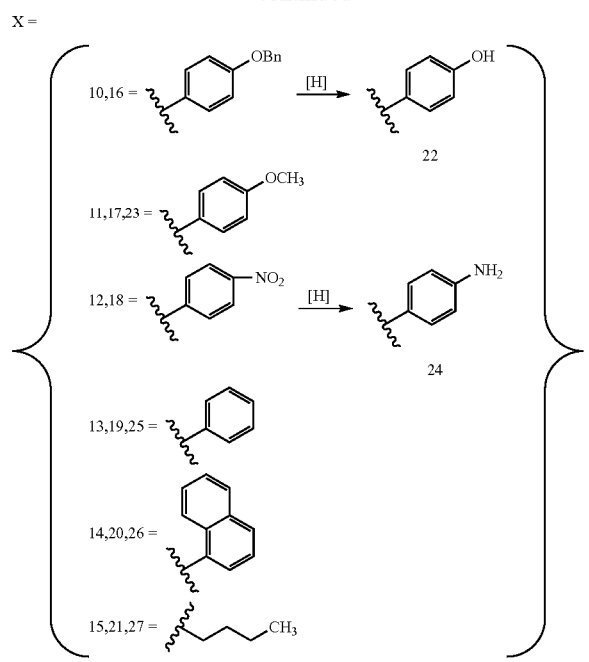

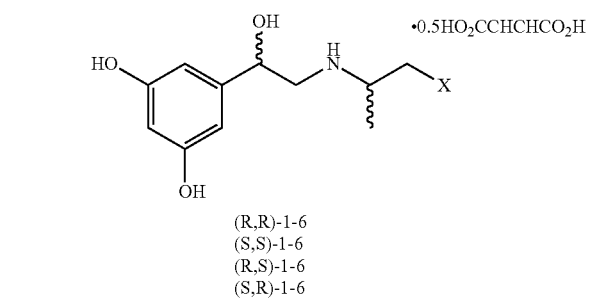

(R,R)-1-6
(S,S)-1-6
(R,S)-1-6
(S,R)-1-6

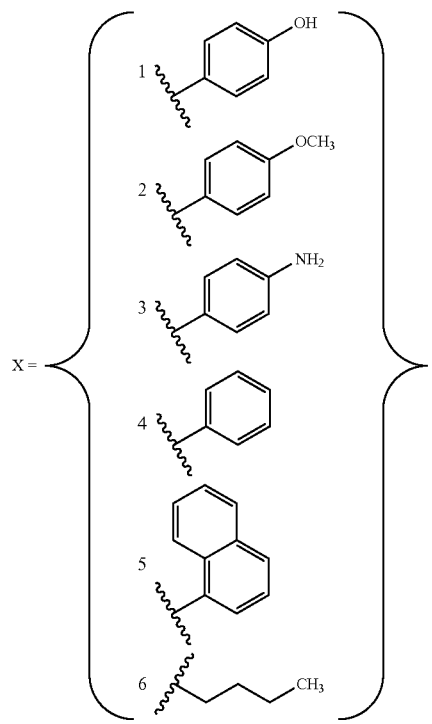

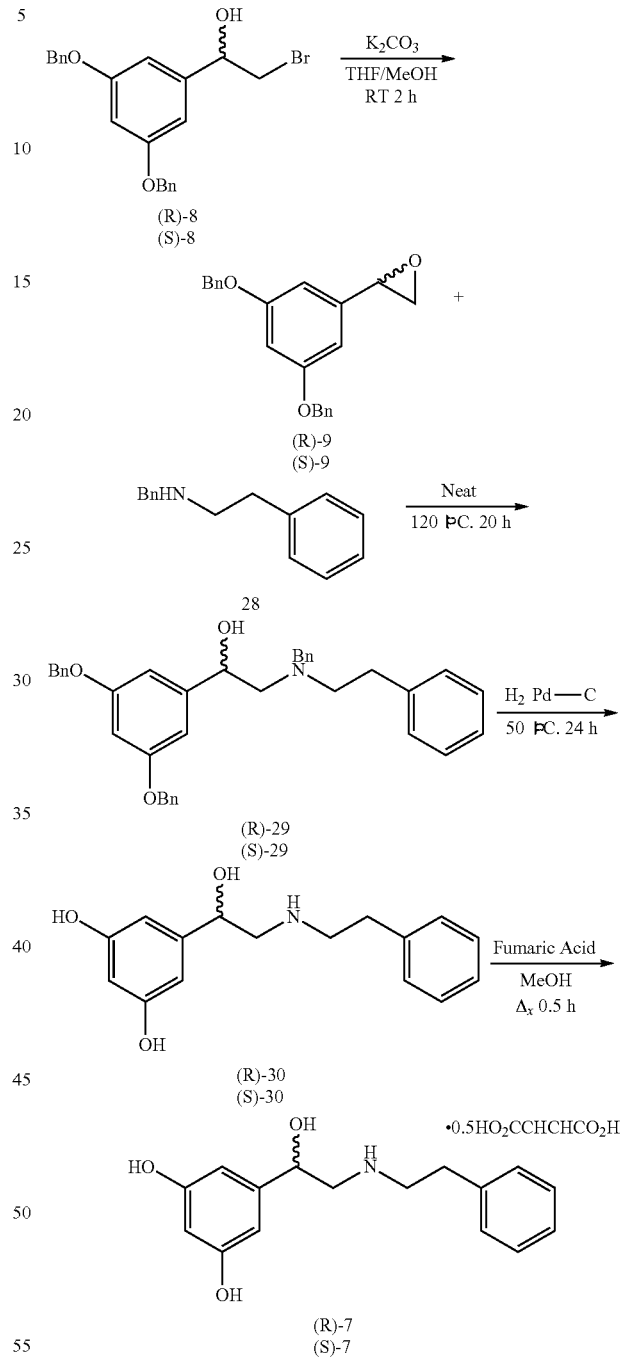

Scheme II: Exemplary synthesis of (R)-7 and (S)-7 using 2-phenethylamine. The resulting compounds may be deprotected by hydrogenation over Pd/C and purified as the fumarate salts.

Scheme III describes an exemplary synthesis for the chiral building blocks used in Scheme II. The (R)- and (S)-3',5'-dibenzyloxyphenyl-bromohydrin enantiomers were obtained by the enantiospecific reduction of 3,5-dibenzyloxy-α-bromoacetophenone using boron-methyl sulfide complex ($BH_3SCH_3$) and either (1R,2S)- or (1S,2R)-cis-1-amino-2-indanol. The required (R)- and (S)-2-benzylaminopropanes were prepared by enantioselective crystallization of the rac-2-benzylaminopropanes using either (R)- or (S)-mandelic acid as the counter ion.

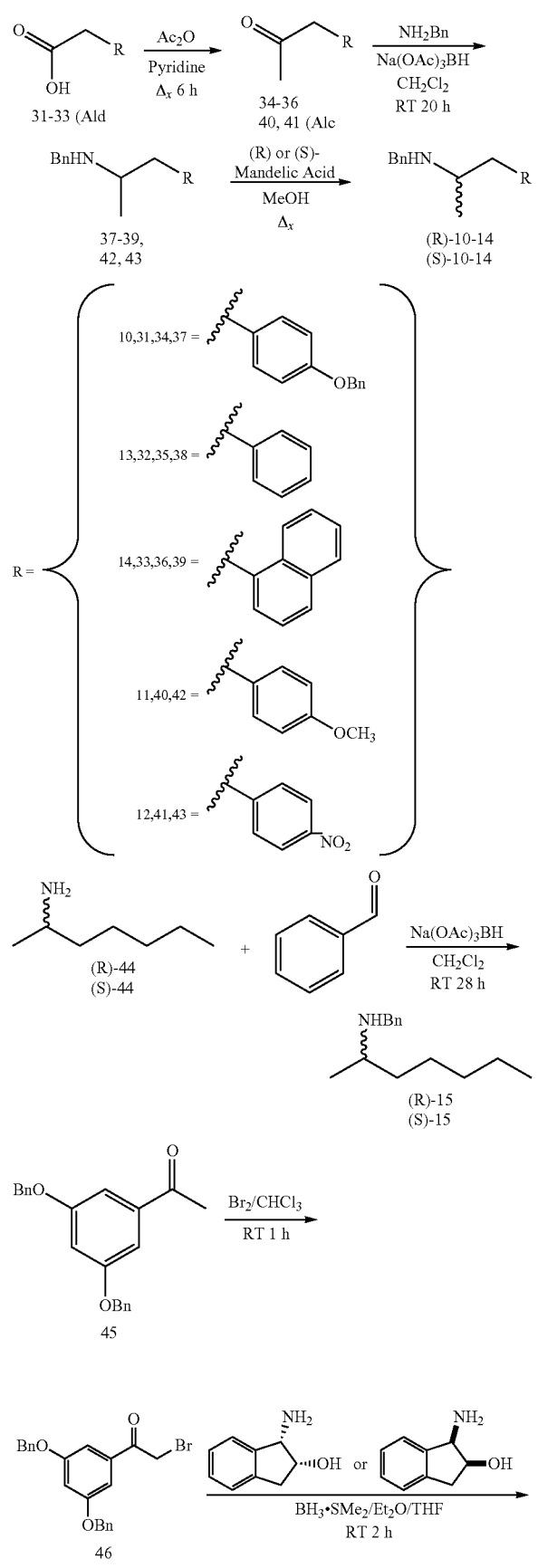

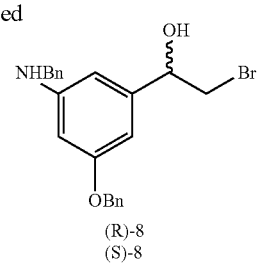

(R)-8
(S)-8

IV. Pharmaceutical Compositions

The disclosed (R,R)-fenoterol and fenoterol analogues can be useful, at least, for the treatment of pulmonary disorders such as asthma and chronic obstructive pulmonary disease (COPD) and cardiac disorders such as congestive heart failure. Accordingly, pharmaceutical compositions comprising at least one disclosed fenoterol compound or analogue are also described herein.

Formulations for pharmaceutical compositions are well known in the art. For example, *Remington's Pharmaceutical Sciences*, by E. W. Martin, Mack Publishing Co., Easton, Pa., 19th Edition, 1995, describes exemplary formulations (and components thereof) suitable for pharmaceutical delivery of (R,R)-fenoterol and disclosed fenoterol analogues. Pharmaceutical compositions comprising at least one of these compounds can be formulated for use in human or veterinary medicine. Particular formulations of a disclosed pharmaceutical composition may depend, for example, on the mode of administration (e.g., oral or parenteral) and/or on the disorder to be treated (e.g., pulmonary disorder or cardiac disorder such as congestive heart failure). In some embodiments, formulations include a pharmaceutically acceptable carrier in addition to at least one active ingredient, such as a fenoterol compound.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions such as powder, pill, tablet, or capsule forms conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances or excipients, such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

The disclosed pharmaceutical compositions may be formulated as a pharmaceutically acceptable salt. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydriodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in *Remington's Pharmaceutical Sciences*, 19th Edition, Mack Publishing Company, Easton, Pa., 1995. A pharmaceutically acceptable salt may also serve to adjust the osmotic pressure of the composition.

The dosage form of a disclosed pharmaceutical composition will be determined by the mode of administration chosen. For example, in addition to injectable fluids, oral dosage forms may be employed. Oral formulations may be liquid such as syrups, solutions or suspensions or solid such as powders, pills, tablets, or capsules. Methods of preparing such dosage forms are known, or will be apparent, to those skilled in the art.

Certain embodiments of the pharmaceutical compositions comprising a disclosed compound may be formulated in unit dosage form suitable for individual administration of precise dosages. The amount of active ingredient such as (R,R)-fenoterol administered will depend on the subject being treated, the severity of the disorder, and the manner of administration, and is known to those skilled in the art. Within these bounds, the formulation to be administered will contain a quantity of the extracts or compounds disclosed herein in an amount effective to achieve the desired effect in the subject being treated. In particular examples, for oral administration the compositions are provided in the form of a tablet containing from about 1.0 to about 50 mg of the active ingredient, particularly about 2.0 mg, about 2.5 mg, 5 mg, about 10 mg, or about 50 mg of the active ingredient for the symptomatic adjustment of the dosage to the subject being treated. In one exemplary oral dosage regimen, a tablet containing from about 1 mg to about 50 mg (such as about 2 mg to about 10 mg) active ingredient is administered two to four times a day, such as two times, three times or four times.

V. Methods of Use

The present disclosure includes methods of treating disorders including pulmonary and cardiac disorders. In some examples, the pulmonary disorder is asthma or chronic obstructive pulmonary disease. In other examples, the cardiac disorder is congestive heart failure.

Disclosed methods includes administering (R,R)-fenoterol or a disclosed fenoterol analogue (and, optionally, one or more other pharmaceutical agents) to a subject in a pharmaceutically acceptable carrier and in an amount effective to treat the pulmonary and/or cardiac disorder. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described above.

An effective amount of (R,R)-fenoterol or a disclosed fenoterol analogue will depend, at least, on the particular method of use, the subject being treated, the severity of the disorder, and the manner of administration of the therapeutic composition. A "therapeutically effective amount" of a composition is a quantity of a specified compound sufficient to achieve a desired effect in a subject being treated. For example, this may be the amount of a (R,R)-fenoterol necessary to prevent, inhibit, reduce or relieve the pulmonary and/or cardiac disorder and/or one or more symptoms of disorder in a subject. Ideally, a therapeutically effective amount of (R,R)-fenoterol or a disclosed fenoterol analogue is an amount sufficient to prevent, inhibit, reduce or relieve the pulmonary and/or cardiac disorder and/or one or more symptoms of the disorder without causing a substantial cytotoxic effect on host cells.

Therapeutically effective doses of a disclosed fenoterol compound or pharmaceutical composition can be determined by one of skill in the art, with a goal of achieving concentrations that are at least as high as the $EC_{50}$ of the applicable compound disclosed in the examples herein. An example of a dosage range is from about 0.001 to about 10 mg/kg body weight orally in single or divided doses. In particular examples, a dosage range is from about 0.005 to about 5 mg/kg body weight orally in single or divided doses (assuming an average body weight of approximately 70 kg; values adjusted accordingly for persons weighing more or less than average). For oral administration, the compositions are, for example, provided in the form of a tablet containing from about 1.0 to about 50 mg of the active ingredient, particularly about 2.5 mg, about 5 mg, about 10 mg, or about 50 mg of the active ingredient for the symptomatic adjustment of the dosage to the subject being treated. In one exemplary oral dosage regimen, a tablet containing from about 1 mg to about 50 mg active ingredient is administered two to four times a day, such as two times, three times or four times.

The specific dose level and frequency of dosage for any particular subject may be varied and will depend upon a variety of factors, including the activity of the specific compound, the metabolic stability and length of action of that compound, the age, body weight, general health, sex and diet of the subject, mode and time of administration, rate of excretion, drug combination, and severity of the condition of the subject undergoing therapy.

The subject matter of the present disclosure is further illustrated by the following non-limiting Examples.

EXAMPLES

Example 1

Materials and Methods

Reagents.
Phenylmethylsulfonyl fluoride (PMSF), benzamidine, leupeptin, pepstatin A, $MgCl_2$, EDTA, Trizma-Hydrochloride (Tris-HCl), (±)-propranolol and minimal essential medium (MEM) were obtained from Sigma Aldrich (St. Louis, Mo.). Egg phosphatidylcholine lipids (PC) were obtained from Avanti Polar Lipids (Alabaster, Ala.). (±)-fenoterol was purchased from Sigma Aldrich and [$^3$H]-(±)-fenoterol was acquired from Amersham Biosciences (Boston, Mass.). The organic solvents n-hexane, 2-propanol and triethylamine were obtained as ultra pure HPLC grade solvents from Carlo Erba (Milan, Italy). Fetal bovine serum and penicillin-streptomycin were purchased from Life Technologies (Gaithersburg, Md.), and [$^{125}$I]-(±)-iodocyanopindolol (ICYP) was purchased from NEN Life Science Products, Inc. (Boston, Mass.).

Preparation and Identification of (R,R)-Fenoterol and (S,S)-Fenoterol.

(R,R)-fenoterol and (S,S)-fenoterol were prepared from (±)-fenoterol using chiral HPLC techniques employing an HPLC column (25 cm×0.46 cm i.d.) containing the amylose tris-(3,5-dimethylphenylcarbamate) chiral stationary phase (CHIRALPAK® AD CSP, Chiral Technologies, West Chester, Pa.; CHIRALPAK is a registered trademark of Daicel Chemical Industries Ltd., Exton, Pa.). The chromatographic system consisted of a JASCO® PU-980 solvent delivery system, and a JASCO® MD-910 multi-wavelength detector set at λ=230 nm, connected to a computer workstation; JASCO is a registered trademark of JASCO, Inc., Tokyo, Japan). A Rheodyne model 7125 injector with 20 µl sample loop was used to inject 0.2-0.3 mg (±)-fenoterol onto the chromatographic system. The mobile phase was n-hexane/2-propanol (88/12 v/v) with 0.1% triethylamine, the flow rate was 1 mL/minute and the temperature of the system was maintained at 25° C. using a column heater/chiller (Model 7955, Jones Chromatography Ltd., UK). The separated (R,R)-fenoterol and (S,S)-fenoterol were collected in 10-mL fractions as the respective peaks eluted from the chromatographic column. A 2-mL intermediate fraction was collected and discarded to improve the enantiomeric purity of the collected isomers.

The stereochemical configurations of the resolved (R,R)-fenoterol and (S,S)-fenoterol were established using circular dichroism (CD) measurements obtained with a JASCO® J-800 spectropolarimeter. The (R,R)-fenoterol and (S,S)-fenoterol were dissolved in 2-propanol and the measurements were obtained using 1 cm path length at room temperature.

Immobilized β2-AR Frontal Chromatography.

The liquid chromatography column containing the immobilized β2-AR was prepared using a previously described technique (Beigi et al., Anal. Chem., 76: 7187-7193, 2004). In brief, cellular membranes were obtained from a HEK 293 cell line that had been transfected with cDNA encoding human β2-AR. An aliquot of a cell pellet suspension corresponding to 5-7 mg total protein, as determined by the micro BCA method, was used to create the column. The membranes were prepared in 10 mL buffer composed of Tris-HCl [50 mM, pH 7.4] containing $MgCl_2$ (2 mM), benzamidine (1 mM), leupeptin (0.03 mM) pepstatin A (0.005 mM) and EDTA (1 mM).

A 180 mg aliquot of immobilized artificial membrane chromatographic support (IAM-PC, 12 micron particle size, 300 Å pore size obtained from Regis Chemical Co., Morton Grove, Ill.) and 80 µM PC were added to the membrane preparation and the resulting mixture was stirred at room temperature for 3 hours, transferred into (5 cm length) nitrocellulose dialysis membrane (MW cutoff 10,000 Da, Pierce Chemical, Rockford, Ill.) and placed in 1 L of dialysis buffer composed of Tris-HCl [50 mM, pH 7.4] containing EDTA (1 mM), $MgCl_2$ (2 mM), NaCl (300 mM) and PMSF (0.2 mM) at 4° C. for 24 hours. The dialysis step was repeated twice using fresh buffer.

After dialysis, the mixture was centrifuged at 120×g for 3 minutes, the supernatant was discarded and the pellet of IAM support containing the immobilized receptor-bearing membranes was collected. The pellet was resuspended in 2 mL chromatographic running buffer, composed of Tris-HCl [10 mM, pH 7.4] containing EDTA (1 mM) and $MgCl_2$ (2 mM) and the suspension was pumped through a HR 5/2 chromatographic glass column (Amersham Pharmacia Biotech, Uppsala, Sweden) at a flow rate of 0.3 mL/minutes using a peristaltic pump. The end adaptors were assembled producing a total gel-bed volume of 0.4 mL. The column was stored at 4° C. when not in use.

The column containing the immobilized β2-AR stationary phase was placed in a chromatographic system composed of a HPLC pump (10-AD, Shimadzu Inc., Columbia, Md.), a manually controlled FPLC injector (Amersham Biotechnology, Uppsala, Sweden) with a 50 µL sample loop, the packed immobilized receptor column and an on-line radioactive flow detector (IN/US, Tampa, Fla.), all connected sequentially. In the frontal chromatographic studies, sample volumes of 5-7 mL were applied continuously until the elution profile showed a plateau region. The running buffer was composed of Tris-HCl [10 mM, pH 7.4] containing EDTA (1 mM) and $MgCl_2$ (2 mM) and 0.05 nM [$^3$H]-(±)-fenoterol, the marker ligand. (R,R)-fenoterol or (S,S)-fenoterol was added to the running buffer in sequential concentrations of 0.1, 80.0, 240, and 700 nM, and applied to the column. The immobilized receptor column was equilibrated with about 80 mL of running buffer, without the added (R,R)-fenoterol or (S,S)-fenoterol respectively, in between each sample injection. All chromatographic studies were carried out at room temperature at a flow rate of 0.2 mL/minutes.

The data were analyzed to determine the number of binding sites and dissociation constant using the non-linear equation (1), $$[M](Vi - V\min) = \frac{P[M]}{Kd + [M]} \quad \text{(Eq. 1)}$$

where $V_i$ is the solute elution volume, $V_{min}$ is the elution volume at the saturation point, P is the number of available binding sites, M is the concentration of the marker ligand and $K_d$ is the dissociation constant of the ligand.

Ligand-Displacement Binding.

Twenty-four hours after adenoviral infection with human β2-AR, HEK293 cells were harvested in lysis buffer, Tris-HCl [5 mM, pH 7.4] containing EGTA [5 mM], and homogenized with 15 strokes on ice. Samples were centrifuged at 30,000×g for 15 minutes to pellet membranes. Membranes were resuspended in binding buffer, Tris-HCl [20 mM, pH 7.4] containing NaCl (120 mM), KCl (5.4 mM), $CaCl_2$ (1.8 mM), $MgCl_2$ (0.8 mM), and glucose (5 mM) and stored in aliquots at −80° C. Binding assays were performed on 5-10 µg of membrane protein using saturating amounts (1-300 pM) of the β-AR-specific ligand [$^{125}$I]cyanopindolol (ICYP). For competition binding, the 5-10 µg of membrane protein were pretreated with 50 µM of $GTP_{\gamma s}$ (non-hydrolyzable guanosine triphosphate) and then incubated with $^{125}$ICYP (50 pM) and different concentrations of fenoterol or its isomers in a total volume of 250 µL. Nonspecific binding was determined in the presence of 20 µM propranolol. Reactions were conducted in 250 µL of binding buffer at 37° C. for 1 hour. The binding reaction was terminated by addition of ice-cold Tris-HCl [10 mM, pH 7.4] to the membrane suspension, followed by rapid vacuum filtration through glass-fiber filters (Whatman GF/C). Each filter was washed three times with an additional 7 mL of ice-cold Tris-HCl [10 mM, pH 7.4]. The radioactivity of the wet filters was determined in a gamma counter. All assays were performed in duplicate, and receptor density was normalized to milligrams of membrane protein. $K_d$ and the maximal number of binding sites ($B_{max}$) for ICYP were determined by Scatchard analysis of saturation binding isotherms. Data from competition studies were analyzed using 1- or 2-site competition binding curves with GRAPHPAD PRISM®

Software (GRAPHPAD PRISM is a registered trademark of GraphPad Software, Inc., San Diego, Calif.).

Example 2

Purification and Identification of (R,R)-Fenoterol and (S,S)-Fenoterol

This example demonstrates the resolution of (R,R)-fenoterol and (S,S)-fenoterol from (±)-fenoterol to a high degree of enantiomeric purity.

Using the chromatographic conditions described in Example 1, (±)-fenoterol was separated into its component enantiomers, (R,R)-fenoterol and (S,S)-fenoterol, on the AD-CSP. As illustrated in FIG. 1, the two stereoisomers were resolved with enantioselectivity factor ($\alpha$) of 1.21 and a resolution factor ($R_S$) of 1.06. Because of the observed tailing of the chromatographic peaks, a 2-mL intermediate fraction was collected and discarded. The collected peaks were analyzed using the same chromatographic conditions and the data demonstrated that both enantiomers had been prepared with >97% stereochemical purity.

Figure 2A:
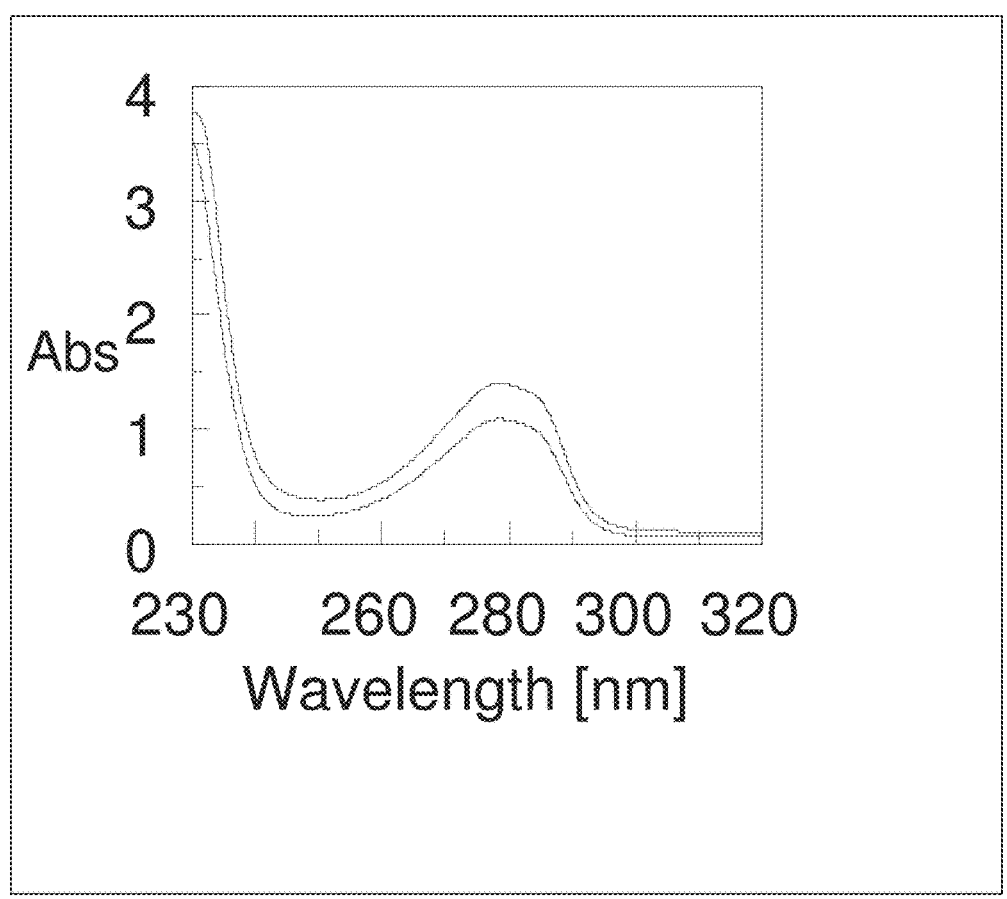
FIG. 2A provides an ultraviolet spectra of (R,R)- and (S,S)-fenoterol.
Figure 2B:
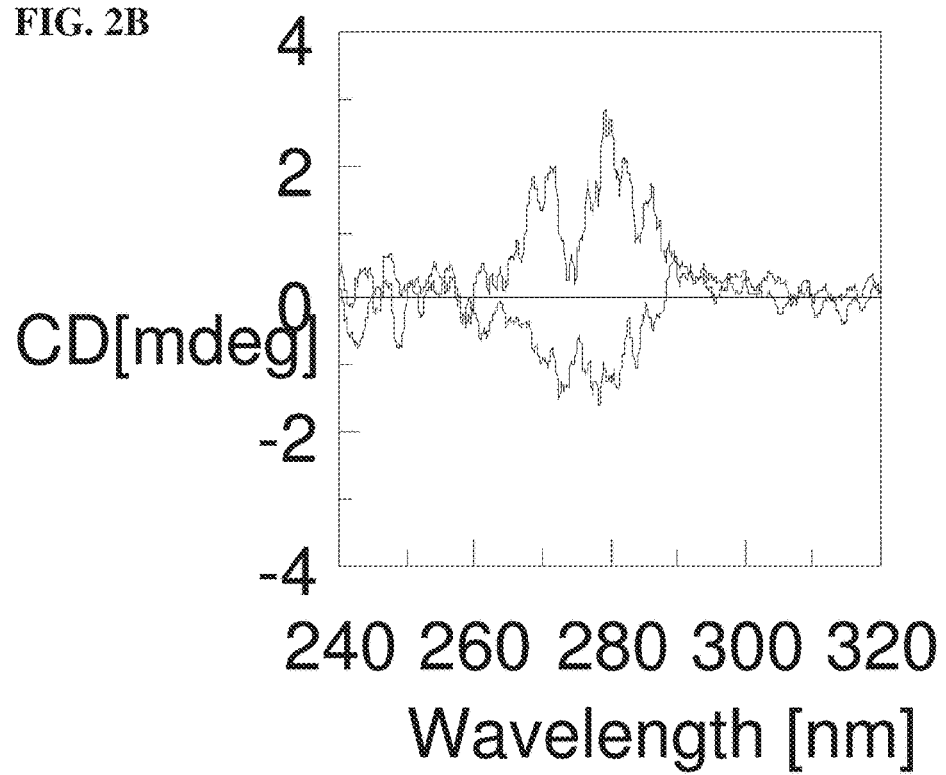
FIG. 2B illustrates a circular dichroism spectra of (R,R)- and (S,S)-fenoterol.

The assignment of the absolute configuration of the isolated fractions was accomplished using their chiroptical properties. The ultraviolet (UV) spectra of both fractions contained identical maxima at about 280 and 230, indicating the same UV chromophores for the two enantiomers. The circular dichroism (CD) spectrum shows, for the less retained enantiomeric fraction, negative CD bands at about 280 and 215 nm, while the spectrum is positive at 230 and 200 nm. The sign of the CD bands is reversed for the most retained fenoterol fraction, this confirming the enantiomeric nature of the two fractions. The lowest energy UV and CD spectra of the two enantiomeric fractions are presented in FIGS. 2A and 2B, respectively. The less retained chromatographic fraction showed a negative CD band at about 280 nm, while the CD spectrum of the most retained chromatographic fraction contained a positive CD band at the same wavelength (FIG. 2B). These results indicate that each of the fractions contained one of the fenoterol enantiomers.

The sign of the lowest energy CD band can be used to assign the absolute configuration to the separated fenoterol enantiomers, by applying the Brewster-Buta/Smith-Fontana sector rule for chiral benzylic derivatives (Brewster and Buta, *J. Am. Chem. Soc.*, 88: 2233-2240, 1996). This sector rule is used to predict the sign of the CD band related to the $^1L_b$ electronic transition of the benzylic compounds, with either hydroxyl or amine moieties and has been primarily applied to conformationally mobile aromatic compounds containing a single stereogenic center. In the case of fenoterol, there are two stereogenic centers. However, it is believed that the observed optical activity is mainly determined by the arylcarbinol moiety, because of the distance between the aromatic ring and the stereogenic center. The application of this rule permitted the assignment of the absolute configuration of (S,S) to the fenoterol enantiomer contained in the less retained fraction that showed a negative CD band at 280 nm, and the absolute configuration of (R,R) to the fenoterol enantiomer contained in the most retained fraction that showed a positive CD band at 280 nm. This assignment was confirmed by the independent synthesis of (S,S)-fenoterol and (R,R)-fenoterol.

These studies indicate that (R,R)-fenoterol and (S,S)-fenoterol can be separated from (±)-fenoterol to a high degree of enantiomeric purity.

Example 3

Chromatographic Determination of the Binding of (R,R)-Fenoterol and (S,S)-Fenoterol to the Immobilized β2-AR This example demonstrates that (R,R)-fenoterol is responsible for the β2-AR binding of the clinically used drug (±)-fenoterol.

The preparation, characterization and application of a liquid chromatographic stationary phase containing immobilized membranes obtained from the β2-AR HEK-293 cell line have been previously reported (Beigi et al., *Anal. Chem.*, 76: 7187-7193, 2004). For example, Beigi et al. (*Anal. Chem.*, 76: 7187-7193, 2004) demonstrated that frontal displacement chromatography could be used to determine the dissociation constants ($K_d$) for the binding of two β2-AR antagonists, (S)-propranolol and CGP 12177A, to the immobilized β2-AR. Zonal displacement chromatography using CGP 12177A as the marker ligand demonstrated that the immobilized β2-AR had retained its enantioselectivity as the addition of (S)-propranolol to the mobile phase produced a greater displacement than the addition of (R)-propranolol (Id.). The addition of (±)-fenoterol to the mobile phase was also shown to produce a conformation change in the immobilized β2-AR (Id.). Agonist-induced conformational changes of the β2-AR, as well as most G-protein coupled receptors, from a resting to active state have been documented (Ghanoui et al., *Proc. Natl. Acad. Sci. U.S.A.*, 98: 5997-6002, 2001).

Presently, the immobilized β2-AR column was equilibrated with the running buffer containing the [$^3$H]-fenoterol, the marker ligand, before the initiation of the displacement studies. It was assumed that the binding data calculated using frontal displacement chromatography reflects the binding of (R,R)-fenoterol and (S,S)-fenoterol to the active state of the receptor. In frontal chromatography, the initial flat portion of the chromatographic trace represents the binding of a marker ligand that is specific for the immobilized target, in this study the β2-AR, as well as non-specific binding to other sites on the immobilized membrane fragments. Saturation of specific binding sites produces a breakthrough front followed by a plateau representing the establishment of a new equilibrium. The addition of a second compound into the mobile phase will produce a shift of the chromatographic trace to the left if the compound competes with the marker for binding to the β2-AR. The relationship between the magnitude of this shift and the concentration of the marker ligand can be used to calculate the binding affinity of the displacer for the target and the number of active binding sites. This approach has been recently reviewed (Moaddel and Wainer, *Anal. Chem. Acata*, 546: 97-105, 2006).

Figure 3:
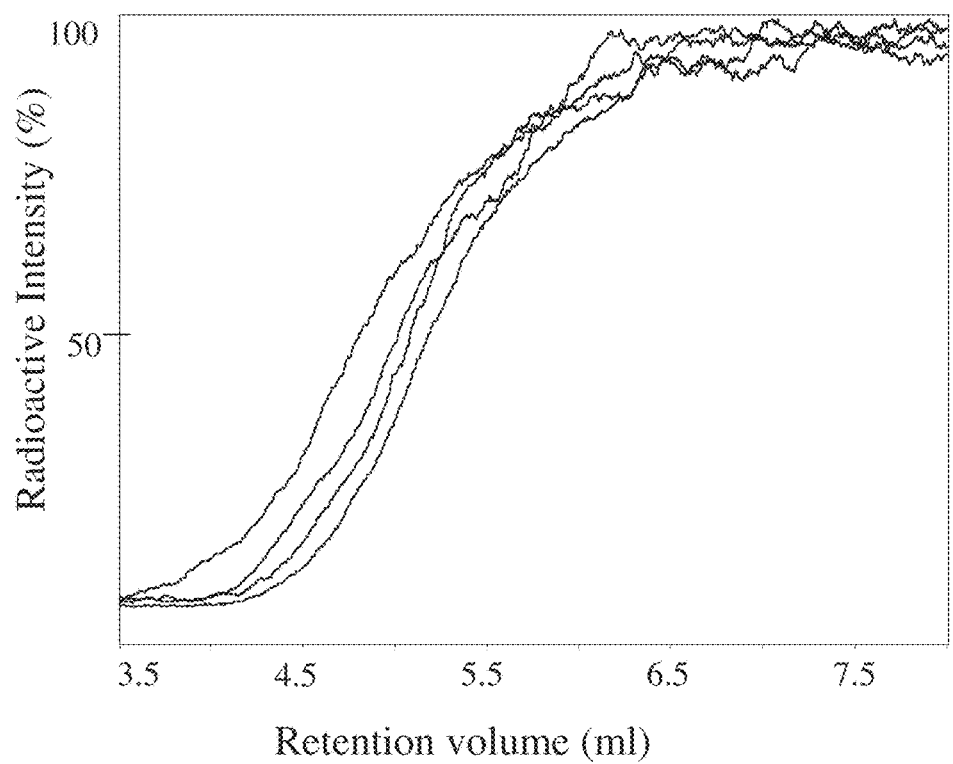
FIG. 3 provides frontal chromatographic elution profiles of [+H]-(±)-fenoterol produced by the addition of (R,R)-fenoterol to the running buffer.

As shown in FIG. 3 (curve 1), the addition of [$^3$H]-fenoterol to the running buffer produced the expected frontal chromatography trace. Sequential addition of increasing concentrations of (R,R)-fenoterol to the running buffer produced a corresponding shift in the chromatographic traces towards smaller retention volumes (FIG. 3, curves 2-4). The magnitude and the shift and the corresponding concentrations of (R,R)-fenoterol were analyzed using Eqn 1 and the calculated dissociation constant, $K_d$, was 472 nM and the amount of available binding sites [P] was 176 pmoles per column, $r^2$=0.9999 (n=2).

The sequential addition of increasing concentrations of (S,S)-fenoterol to the running buffer produced no corresponding shift in the chromatographic traces toward shorter retention times. Thus, (S,S)-fenoterol had no significant affinity for the immobilized β2-AR.

In order to validate the chromatographic results, a standard membrane binding study was conducted using membranes obtained from the same HEK-293 cell line used to create the immobilized β2-AR column. The data reflected the presence of a single binding site with (mean±SD) $K_d$=457±55 nM (n=4) for (R,R)-fenoterol and 109,000±10,400 nM (n=4) for (S,S)-fenoterol. These data indicate that frontal affinity chromatography on immobilized cellular membrane columns can be used to determine the magnitude and enantioselectivity of ligand binding to the target receptor. Further, the results from the frontal affinity chromatography and ligand competition binding studies both demonstrate that (R,R)-fenoterol is responsible for the β2-AR binding of the clinically used drug (±)-fenoterol.

Example 4

The Effect of (R,R)-Fenoterol and (S,S)-Fenoterol on Cardiomyocyte Contractility This example demonstrates that (R,R)-fenoterol and (S,S)-fenoterol differentially activate β2-adrenergic receptor/stimulatory heterotrimeric G protein (AR/$G_s$) signaling in regards to cell contractility.

To determine if (R,R)-fenoterol and (S,S)-fenoterol differentially activate β2-AR/$G_s$ signaling in the regulation of cell contractility, freshly isolated adult rat cardiomyocytes were perfused with various concentrations of either (R,R)-fenoterol or (S,S)-fenoterol. These studies were carried out using a previously described approach (Thou et al., *Mol. Pharmacol.*, 200, 58: 887-894). In brief, single ventricular myocytes were isolated from 2-4 month old rat hearts by a standard enzymatic technique. The isolated cells were resuspended in HEPES buffer solution [20 mM, pH 7.4] containing, NaCl (137 mM), KCl (5.4 mM), $MgCl_2$ (1.2 mM), $NaH_2PO_4$ (1.0 mM), $CaCl_2$ (1.0 mM), and glucose (20 mM). All studies were performed within 8 hours of cell isolation.

The cells were placed on the stage of an inverted microscope (Zeiss model IM-35, Zeiss, Thornwood, N.Y.), perfused with the HEPES-buffered solution at a flow rate of 1.8 mL/minutes, and electrically stimulated at 0.5 Hz at 23° C. Cell length was monitored by an optical edge-tracking method using a photodiode array (Model 1024 SAQ, Reticon, Boston, Mass.) with a 3 ms time resolution. Cell contraction was measured by the percent shortening of cell length following electrical stimulation.

Figure 4A:
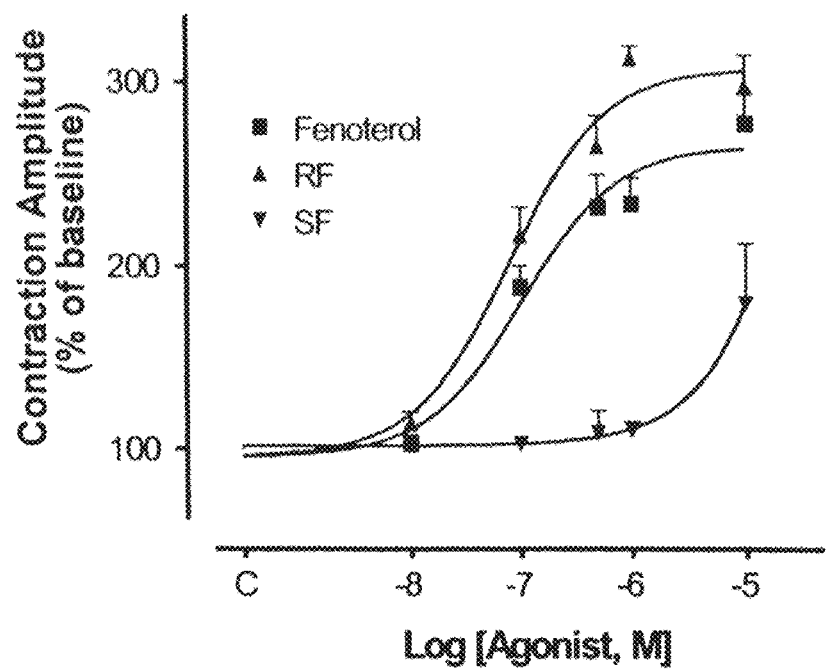
FIG. 4A is a graph including dose-response curves generated by treating freshly isolated rat ventricular myocytes with (±)-fenoterol, (R,R)-fenoterol or (S,S)-fenoterol.
Figure 4B:
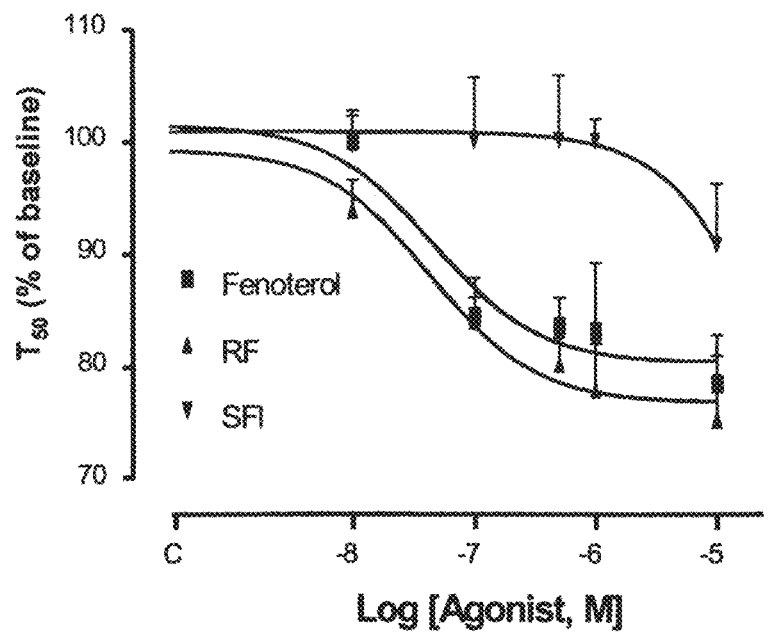
FIG. 4B is a graph including dose-response curves of $T_{50\%}$ relaxation in freshly isolated rat ventricular myocytes generated by treatment with (±)-fenoterol, (R,R)-fenoterol or (S,S)-fenoterol.

The addition of (R,R)-fenoterol ($10^{-8}$ to $10^{-5}$ M) produced a markedly elevated positive inotropic effect and a significant upward shift of the dose-response curve compared to (±)-fenoterol (FIG. 4A). This was demonstrated by an increase in the maximum contractile response from 265±11.6% to 306±11.8% resting cell length (p<0.05) and a reduction in $EC_{50}$ from −7.0±0.2 to −7.1±0.2 log [M] (p<0.05). In contrast, (S,S)-fenoterol had only a minor positive inotropic effect (FIG. 4B).

The cardiomyocyte contractility studies indicate that (R,R)-fenoterol is responsible for the observed β2-AR agonist activity in cardiomyocytes.

Example 5

Synthesis

General Procedures:

All reactions were carried out using commercial grade reagents and solvents. Tetrahydrofuran (THF) was dried by refluxing over sodium and benzophenone. Dichloromethane was dried by refluxing over calcium hydride. Ultraviolet spectra were recorded on a Cary 50 Concentration spectrophotometer. Optical rotations were done on a Rudolph Research Autopol IV. NMR Spectra were recorded on a Varian Mercury VMX 300-MHz spectrophotometer using tetramethylsilane as the internal standard. NMR multiplicities were reported by using the following abbreviations: s, singlet; d, doublet; t, triplet; q, quartet; p, pentet; m, multiplet; apt., apparent; and br, broad. Low resolution mass spectra were obtained on a Finnigan $LCQ^{Duo}$ LC MS/MS atmospheric pressure chemical ionization (API) quadrupole ion trap MS system equipped with both electrospray (ESI) and atmospheric pressure chemical ionization (APCI) probes. Analytical HPLC data was obtained using a Waters 2690 Separations Module with PDA detection. Method (a): ThermoHypersil BDS 100×4.6 mm C18 column, $H_2O$/$CH_3CN$/TFA. Method (b): Brownlee Phenyl Spheri-5 100×4.6 mm, water/acetonitrile/TFA. Method (c): Vydac 150×4 mm C18 column, $H_2O$/isopropanol/TFA. Method (d): CHIRALPAK® AD-H 250×10 mm, 95/5/0.05 $CH_3CN$/isopropanol/diethylamine. Merck silica gel (230-400 mesh) was used for open column chromatography.

3',5'-Dibenzyloxy-α-bromoacetophenone (46).

A solution of 2.4 mL (46 mmol) of $Br_2$ in 45 mL of $CHCl_3$ was added dropwise over 1 h to a chilled, stirring solution of 9.66 g (29 mmol) of 3',5'-dibenzyloxyacetophenone (45) in 40 mL of $CHCl_3$. The resulting solution was allowed to warm to room temperature over 1 hour with good stirring, then poured into 100 mL of cold $H_2O$ and transferred to a separatory funnel where the $CHCl_3$ fraction was isolated, washed with brine solution, dried ($Na_2SO_4$), filtered, and concentrated to 10.8 g. This material was applied to 500 g of silica gel, eluting with $CHCl_3$ to obtain 2.65 g (22%) of compound 46 as a white solid. $^1H$ NMR ($CDCl_3$) δ 4.39 (s, 2H), 5.08 (s, 4H), 6.85 (t, 1H, J=2.1 Hz), 7.20 (d, 2H, J=2.4 Hz), 7.31-7.44 (m, 10H).

General Procedure for the Enantioselective Reduction of Compound 46 to 3',5'-Dibenzyloxyphenylbromohydrins [(R)-8, (S)-8].

Under argon atmosphere, 0.06 mL (0.316 mmol, 10 mol %) of 5.0 M boron-methyl sulfide complex ($BH_3SCH_3$) in diethyl ether was added in one portion to a solution of 25 mg (0.16 mmol, 5 mol %) of the appropriate cis-1-amino-2-indanol in 3 mL of dry THF. This material under argon was added over 30 minutes to a solution of 1.3 g (3.16 mmol) of 3',5'-dibenzyloxy-α-bromoacetophenone in 20 mL of dry THF, while at the same time adding in ~0.05 mL pulses, 0.45 mL of 5.0 M boron-methyl sulfide complex. The resulting solution was stirred under argon for 2 hours, and then quenched with 3 mL of methanol, controlling gas evolution. Solvents were removed in vacuo and the resulting residue taken up in 30 mL of $CHCl_3$ and washed with 25 mL of 0.2 M sulfuric acid followed by 20 mL of brine, then dried ($Na_2SO_4$), filtered, and evaporated.

(R)-(−)-3',5'-Dibenzyloxyphenylbromohydrin [(R)-8].

Prepared with (1R,2S)-(+)-cis-1-amino-2-indanol as the enantioselective reduction catalyst to give 1.02 g (78%) of (R)-8 as a fine white powder. $^1H$ NMR ($CDCl_3$) δ 3.44 (dd, 1H, J=9.0, 10.5 Hz), 3.55 (dd, 1H, J=3.3, 10.5 Hz), 4.79 (dd, 1H, J=3.3, 8.7 Hz), 4.97 (s, 4H), 6.51 (t, 1H, J=2.4 Hz), 6.57 (d, 2H, J=1.8 Hz), 7.21-7.38 (m, 10H); $[\alpha]_D$=−12.1° (c=1.0 MeOH).

(S)-(+)-3',5'-Dibenzyloxyphenylbromohydrin [(S)-8].

Prepared with (1S,2R)-(−)-cis-1-amino-2-indanol as the enantioselective reduction catalyst to give 1.07 g (82%) of (S)-8 as a fine white powder. $^1$H NMR (CDCl$_3$) δ 3.43 (dd, 1H, J=9.0, 10.5 Hz), 3.55 (dd, 1H, J=3.3, 10.5 Hz), 4.78 (dd, 1H, J=3.3, 8.7 Hz), 4.96 (s, 4H), 6.50 (t, 1H, J=2.4 Hz), 6.57 (d, 2H, J=1.8 Hz), 7.21-7.39 (m, 10H); $[\alpha]_D$=+11.8° (c=0.90 MeOH).

4-Benzyloxyphenylacetone (34).

To 10.0 g (41.3 mmol) of 4-benzyloxyphenylacetic acid (31) was added, 20 mL of acetic anhydride and 20 mL of pyridine, which was heated to reflux with stirring under argon atmosphere for 6 hours. Solvents were evaporated and residue dissolved in CHCl$_3$ (50 mL) and washed with 1N NaOH (2×50 mL). Dried organic layer (MgSO$_4$), filtered, and evaporated to 11.8 g of an amber oil. Vacuum distillation at 0.1 mm Hg in an oil-bath set to 170° C. followed by silica gel chromatography eluting with 8/2 CH$_2$Cl$_2$-hexanes gave 2.68 g (27%). $^1$H NMR (CDCl$_3$) δ 2.14 (s, 3H), 3.63 (s, 2H), 5.05 (s, 2H), 6.94 (d, 2H, J=8.7 Hz), 7.10 (d, 2H, J=8.7 Hz), 7.26-7.47 (m, 5H).

Phenylacetone (35).

A solution of 20.4 g (0.15 mol) of phenylacetic acid, acetic anhydride (70 mL) and pyridine (70 mL) was heated to reflux with stirring under argon atmosphere for 6 hours. Solvents were evaporated and residue dissolved in CHCl$_3$ (100 mL), washed with 1N NaOH (2×100 mL) and dried the organic layer (MgSO$_4$), filtered, and evaporated to give 20.4 g. Vacuum distillation at 0.1 mm Hg in an oil bath set to 160° C., followed by silica gel chromatography eluting with 1/1 hexanes/CH$_2$Cl$_2$ gave 5.5 g (27%). $^1$H (CDCl$_3$) δ 2.15 (s, 3H), 3.70 (s, 2H), 7.20-7.36 (m, 5H).

1-Naphthalen-1-yl-propan-2-one (36).

A solution of 37.2 g (20 mmol) of naphthoic acid (33), acetic anhydride (100 mL) and pyridine (100 mL) was heated to reflux with stirring under argon atmosphere for 6 hours. Evaporated solvents, dissolved residue in CHCl$_3$ (200 mL) and washed with 1N NaOH (2×150 mL), dried organic layer (MgSO$_4$), filtered, and evaporated to give 34.6 g. Distillation at 0.5 mm Hg in an oil bath set to 170° C., followed silica gel chromatography eluting with 1/1 hexanes/CH$_2$Cl$_2$ gave 9.7 g (26%). $^1$H (CDCl$_3$) δ 2.11 (s, 3H), 4.12 (s, 2H), 7.40-7.53 (m, 4H), 7.81 (d, 1H, J=8.4 Hz), 7.87-7.90 (m, 2H).

General Procedure for Preparation of 2-benzylaminopropanes (37-39, 42, 43).

To the appropriate ketone (1 eq) in CH$_2$Cl$_2$ (c=0.5 M), cooled to 0° C. was added glacial HOAc (1 eq), followed by benzylamine (1 eq) and NaBH(AcO)$_3$ (1.4 eq). The reaction mixture was warmed to room temperature and stirred under argon for 20 hours. The reaction mixture was cooled (ice bath), 10% NaOH (5 eq) was added dropwise and then extracted into CH$_2$Cl$_2$, washed with brine. The product was then dried (Na$_2$SO$_4$), filtered and evaporated.

1-(4-benzyloxy)-2-benzylaminopropane (37).

Prepared from 4-benzyloxyphenylacetone (34; 2.0 g, 8.3 mmol) to afford 2.61 g (95%) as a tan solid. $^1$H (CDCl$_3$) δ 1.10 (d, 3H, J=6.3 Hz), 2.50-2.58 (m, 1H). 2.68-2.77 (m, 1H), 2.82-2.89 (m, 1H), 3.75 (dd, 2H, J=12 Hz, J=30 Hz), 5.05 (s, 2H), 6.90 (d, 2H, J=8.7 Hz), 7.04 (d, 2H, J=8.7 Hz), 7.17-7.42 (m, 10H); MS (APCI+) m/z (rel): 332 (100).

1-Phenyl-2-benzylaminopropane (38).

Prepared from phenylacetone (35; 5.5 g, 41 mmol) to afford 8.4 g (91%) as a tan solid. $^1$H (CDCl$_3$) δ 1.09 (d, 3H, J=6.3 Hz), 2.61-2.81 (m, 2H), 2.92 (m, 1H), 3.80 (dd, 2H), 7.14-7.30 (m, 10H); MS (APCI+) m/z (rel): 226 (100).

1-(1'-Naphthyl)-2-benzylaminopropane (39).

Prepared from 1-naphthalen-1-yl-propan-2-one (36; 5.0 g, 27.1 mmol) to afford 7.0 g (94%) as a tan solid. $^1$H (CDCl$_3$) δ 1.14 (d, 3H, J=6.0 Hz), 3.02-3.18 (m, 2H), 3.27 (m, 1H), 3.80 (dd, 2H, J=13.2, 43.8 Hz), 7.13-7.23 (m, 5H), 7.31-7.48 (m, 4H), 7.73 (d, 1H, J=7.8 Hz), 7.83-7.86 (m, 1H), 7.96-7.99 (m, 1H); MS (APCI+) m/z (rel): 276 (100).

1-(4'-Methoxyphenyl)-2-benzylaminopropane (42).

Prepared from 4-methoxyphenyl-acetone (40; 2.75 g, 13.1 mmol) to afford 2.31 g (97%). $^1$H (CDCl$_3$) δ 1.10 (d, 3H, J=6.3 Hz), 2.56-2.75 (m, 2H), 2.90 (m, 1H), 3.79 (s, 1H), 3.79 (m, 2H, J=13.2 Hz), 6.82 (d, 2H, J=8.7 Hz), 7.07 (d, 2H, J=8.7 Hz), 7.18-7.32 (m, 5H); MS (APCI+) m/z (rel): 256 (100).

1-(4'-nitrophenyl)-2-benzylaminopropane (43).

Prepared from 4-nitrophenyl-acetone (41; 4.95 g, 28 mmol) to afford 7.32 g (98%) as an amber oil. $^1$H (CDCl$_3$) δ 1.60 (d, 3H, J=6.3 Hz), 2.73-2.85 (m, 1H), 3.00-3.12 (m, 2H), 3.86 (dd, 2H, J=26 Hz, J=60 Hz), 7.23-7.40 (m, 5H), 7.30 (d, 2H, J=9.0 Hz), 8.14 (d, 2H, J=8.7 Hz). MS (APCI+) m/z (rel): 271 (100).

General Procedure for Enantiomeric Separation of 2-benzylaminopropanes [(R)-10-14, (S)-10-14].

The appropriate racemic 2-benzylaminopropane (1 eq) was combined with the appropriate optically active mandelic acid (1 eq) in methanol (c=0.5 M) and refluxed until the solution homogenized, then cooled to RT. The crystals were filtered, collected, and recrystallized twice from methanol (c=0.3 M) to afford the optically active 2-benzylaminopropane.mandelic acid salt. The salts were converted to the free amine for the purpose of collecting NMR and rotation data by partitioning the mandelic acid salt between 10% K$_2$CO$_3$ and CHCl$_3$, drying organic extracts (Na$_2$SO$_4$) and evaporating.

(R)-(−)-1-(4'-benzyloxy)-2-benzylaminopropane [(R)-10].

A sample of 2.13 g (6.42 mmol) of 1-(4-benzyloxy)-2-benzylaminopropane (37) was reacted with 972 mg (6.42 mmol) of (R)-(−)-mandelic acid to give 295 mg (28% based on enantiomeric abundance) of the free amine after workup. $^1$H NMR (CDCl$_3$) δ 1.12 (d, 3H, J=6.3 Hz), 2.58-2.78 (m, 2H), 2.82-2.91 (m, 1H), 3.75 (dd, 2H, J=12 Hz, J=30 Hz)), 5.07 (s, 2H), 6.93 (d, 2H, J=8.7 Hz), 7.10 (d, 2H, J=8.7 Hz), 7.21-7.42 (m, 10H); MS (APCI+) m/z (rel): 332 (100); $[\alpha]_D$=−19.1° (c=1.4, MeOH).

(S)-(+)-1-(4'-benzyloxy)-2-benzylaminopropane [(S)-10].

The washes from the separation of (R)-10 were concentrated and partitioned between 50 mL of chloroform and 50 mL of 10% K$_2$CO$_3$ in water. Washed organics with brine, dried (Na$_2$SO$_4$), filtered and evaporated to 1.70 g (5.1 mmol). The organics were brought to reflux with 782 mg (5.1 mmol) of (S)-(+)-mandelic acid (as previously described) and crystallized 3 times to obtain 670 mg of the (S)-amine.(S)-mandelic acid salt. The (S)-amine.(S)-mandelic acid salt was triturated in ether then partitioned between 30 mL of chloroform and 20 mL of 10% K$_2$CO$_3$ in water. The organic partition was washed with brine, then dried (Na$_2$SO$_4$), filtered and evaporated to give 366 mg of the free amine (33% based on enantiomeric abundance). $^1$H NMR (CDCl$_3$) δ 1.10 (d, 3H, J=6.3 Hz), 2.58-2.78 (m, 2H), 2.82-2.91 (m, 1H), 3.76 (dd, 2H, J=12, 30 Hz), 5.06 (s, 2H), 6.93 (d, 2H, J=8.7 Hz), 7.09 (d, 2H, J=8.7 Hz), 7.21-7.42 (m, 10H); MS (APCI+) m/z (rel): 332 (100); $[\alpha]_D$=+19.2° (c=1.5 MeOH).

(R)-(−)-1-(4'-Methoxyphenyl)-2-benzylaminopropane [(R)-11].

A sample of 3.02 g (11.8 mmol) of 1-(4'-methoxyphenyl)-2-benzylaminopropane (42) was reacted with 1.8 g (11.8 mmol) (S)-(+)-mandelic acid to give 530 mg (35% based on enantiomeric abundance) of the free amine after workup. $^1$H NMR (CDCl$_3$) δ 1.10 (d, 3H, J=6.3 Hz), 2.57-2.76 (m, 2H), 2.88-2.94 (m, 1H), 3.79 (s, 3H), 3.72-3.88 (m, 2H), 6.82 (d, 2H, J=8.7 Hz), 7.07 (d, 2H, J=8.4 Hz), 7.15-7.31 (m, 5H); MS (APCI+) m/z (rel): 256 (100); [α]$_D$=−30.4° (c=1.25 MeOH).

(S)-(+)-1-(4'-Methoxyphenyl)-2-benzylaminopropane [(S)-11].

A sample of 3.36 g (13.2 mmol) of the racemate 1-(4'-methoxyphenyl)-2-benzylaminopropane (42) was reacted with 2.0 g (13.2 mmol) of (R)-(−)-mandelic acid to give 740 mg (44% based on enantiomeric abundance) of the free amine after workup. $^1$H NMR, (CDCl$_3$) δ 1.10 (d, 3H, J=6.2 Hz), 2.55-2.76 (m, 2H), 2.88-2.95 (m, 1H), 3.73-3.88 (m, 2H), 3.79 (s, 3H), 6.80 (d, 2H, J=8.7 Hz), 7.08 (d, 2H, J=8.4 Hz), 7.15-7.30 (m, 5H); MS (APCI+) m/z (rel): 256 (100); [α]$_D$=+30.5° (c=1.1 MeOH).

(R)-(−)-1-(4'-nitrophenyl)-2-benzylaminopropane [(R)-12].

A sample of 2.0 g (7.3 mmol) of 1-(4'-nitrophenyl)-2-benzylaminopropane (43) was reacted with 1.13 g (7.3 mmol) of (S)-(+)-mandelic acid to give 486 mg (49% based on enantiomeric abundance) of the free amine after workup. $^1$H NMR (CDCl$_3$) δ 1.60 (d, 3H, J=6.3 Hz), 2.73-2.85 (m, 1H), 3.00-3.12 (m, 2H), 3.86 (dd, 2H, J=26 Hz, J=60 Hz), 7.23-7.40 (m, 5H), 7.30 (d, 2H, J=9.0 Hz), 8.14 (d, 2H, J=8.7 Hz); MS (APCI+) m/z (rel): 271 (100); [α]$_D$=−9.3° (c=1.0 MeOH).

(S)-(+)-1-(4'-nitrophenyl)-2-benzylaminopropane [(S)-12].

A sample of 2.0 g (7.3 mmol) of 1-(4'-nitrophenyl)-2-benzylaminopropane (43) was reacted with 1.13 g (7.3 mmol) of (R)-(−)-mandelic acid to give 640 mg (65% based on enantiomeric abundance) of the free amine after workup. $^1$H NMR (CDCl$_3$) δ 1.60 (d, 3H, J=6.3 Hz), 2.73-2.85 (m, 1H), 3.00-3.12 (m, 2H), 3.86 (dd, 2H, J=26, 60 Hz), 7.23-7.40 (m, 5H), 7.30 (d, 2H, J=9.0 Hz), 8.14 (d, 2H, J=8.7 Hz); MS (APCI+) m/z (rel): 271 (100); [α]$_D$=+8.2° (c=1.0 MeOH).

(R)-(−)-1-Phenyl-2-benzylaminopropane [(R)-13].

A sample of 2.62 g (11.6 mmol) of 1-phenyl-2-benzylaminopropane (38) was reacted with 1.77 g (11.6 mmol) of (S)-(+)-mandelic acid to give 747 mg (57% based on enantiomeric abundance) of the free amine after workup. $^1$H NMR (CDCl$_3$) δ 1.13 (d, 3H, J=6.0 Hz), 2.62-2.84 (m, 2H), 2.92-2.99 (m, 1H), 3.81 (dd, 2H, J=13.2, 34.5 Hz) 7.14-7.29 (m, 10H); MS (APCI+) m/z (rel): 226 (100); [α]$_D$=−24.5° (c=1.10 MeOH).

(S)-(+)-1-Phenyl-2-benzylaminopropane [(S)-13].

A sample of 5.0 g (22.2 mmol) of racemic 1-phenyl-2-benzylaminopropane (38) was reacted with 3.4 g (22.2 mmol) of (R)-(−)-mandelic acid to give 2.15 g (86% based on enantiomeric abundance) of the free amine after workup. $^1$H NMR (CDCl$_3$) δ 1.11 (d, 3H, J=6.0 Hz), 2.62-2.84 (m, 2H), 2.92-2.99 (m, 1H), 3.81 (dd, 2H, J=13.2, 34.5 Hz), 7.14-7.29 (m, 5H); MS (APCI+) m/z (rel): 226 (100); [α]$_D$=+18.2° (c=0.85 MeOH).

(R)-(−)-1-(1'-Naphthyl)-2-benzylaminopropane [(R)-14].

The washes recovered from the separation of (S)-14 were concentrated and partitioned between 40 mL of chloroform and 40 mL of 10% K$_2$CO$_3$ in water. The organic partition was washed with 20 mL of brine then dried (Na$_2$SO$_4$) to afford 1.16 g (4.2 mmol) of the free amine, which was reacted with 640 mg (4.2 mmol) of (S)-(+)-mandelic acid. 588 mg (46% based on enantiomeric abundance) of the free amine was obtained. $^1$H NMR (CDCl$_3$) δ 1.07 (d, 3H, J=6.0 Hz), 3.02-3.18 (m, 2H), 3.27 (m, 1H), 3.74 (dd, 2H, J=13.2, 30.9 Hz), 7.13-7.23 (m, 5H), 7.31-7.48 (m, 4H), 7.73 (d, 1H, J=7.8 Hz), 7.83-7.86 (m, 1H), 7.96-7.99 (m, 1H); MS (APCI+) m/z (rel): 276 (100); [α]$_D$=−5.8° (c=1.0 MeOH).

(S)-(+)-1-(1'-Naphthyl)-2-benzylaminopropane [(S)-14].

A sample of 2.6 g (9.4 mmol) of 1-(1'-naphthyl)-2-benzylaminopropane (39) was reacted with 1.44 g (9.4 mmol) of (R)-(−)-mandelic acid to give 420 mg (21% based on enantiomeric abundance) of the free amine after workup. $^1$H NMR (CDCl$_3$) δ 1.07 (d, 3H, J=6.0 Hz), 3.02-3.18 (m, 2H), 3.27 (m, 1H), 3.74 (dd, 2H, J=13.2, 30.9 Hz), 7.13-7.23 (m, 5H), 7.31-7.48 (m, 4H), 7.73 (d, 1H, J=7.8 Hz), 7.83-7.86 (m, 1H), 7.96-7.99 (m, 1H); MS (APCI+) m/z (rel): 276 (100); [α]$_D$=+6.3° (c=1.0 MeOH).

(R)-(−)-2-Benzylaminoheptane [(R)-15].

A sample of 0.65 mL (4.4 mmol) of (R)-(−)-2-aminoheptane (R-44) 0.44 mL (4.4 mmol) of benzaldehyde and 0.1 mL of HOAc were combined in 40 mL of CH$_2$Cl$_2$ and then cooled to 0° C. To the reaction mixture was added 2.75 mg (13 mmol) of sodium triacetoxyborohydride in one portion, which was stirred under argon at room temperature for 28 hours. The reaction mixture was diluted with 30 mL of CH$_2$Cl$_2$, cooled in an ice bath and 80 mL of 5% NaOH (in water) was added. Fractions were separated, organics (Na$_2$SO$_4$) dried and evaporated to 638 mg (71%) of (R)-15. $^1$H NMR (CDCl$_3$) δ 0.88 (m, 3H), 1.08 (d, 3H J=6.6 Hz), 1.20-1.39 (m, 6H), 1.41-1.67 (m, 2H), 3.62-3.77 (m, 1H), 3.75 (p, 2H, J=12 Hz), 7.17-7.41 (m, 5H); MS (APCI+) m/z (rel): 206 (100); [α]$_D$=+6.9° (c=1.0, MeOH).

(S)-(+)-2-Benzylaminoheptane [(S)-15].

A sample of 0.15 mL (1 mmol) of (S)-(+)-2-aminoheptane ((S)-44) 0.1 mL (1 mmol) of benzaldehyde and 0.1 mL of HOAc were combined in 10 mL of CH$_2$Cl$_2$ and cooled to 0° C., then added 650 mg (3 mmol) of sodium triacetoxyborohydride in one portion. The reaction mixture was stirred under argon at room temperature for 28 hours. The mixture was diluted with 10 mL of dichloromethane, cooled in an ice bath and 20 mL of 5% NaOH (in water) was added. Fractions were separated, organics were dried (Na$_2$SO$_4$) and evaporated to 154 mg (70%). $^1$H NMR (CDCl$_3$) δ 0.88 (m, 3H), 1.08 (d, 3H J=6.6 Hz), 1.19-1.37 (m, 6H), 1.41-1.67 (m, 2H), 3.62-3.77 (m, 1H), 3.75 (p, 2H, J=12 Hz), 7.17-7.41 (m, 5H); MS (APCI+) m/z (rel): 206 (100); [α]$_D$=+7.8° (c=1.0, MeOH).

Preparation of Fenoterol Analogs, Procedure A.

To form the epoxide, the appropriate 3',5'-dibenzyloxyphenylbromohydrin ((R)-8) or (S)-8 (1 eq) was combined with K$_2$CO$_3$ (1.4 eq) in 1:1 THF/MeOH (c=0.3 M) and stirred for 2 hours under argon at room temperature. The solvent was removed and the residue partitioned between toluene and H$_2$O. The toluene fraction was isolated, dried (Na$_2$SO$_4$), filtered, and evaporated. The residue was dissolved with the appropriate free benzylamine (R)- or (S)-10-15, 28 (0.95 eq) in a good amount of toluene and evaporated again under high vacuum to remove trace H$_2$O. The resulting colorless residue was heated to 120° C. under argon for 20 hours, cooled and checked by $^1$H NMR and mass spectrometry to confirm coupling. The residue was dissolved in EtOH (c=0.07 M) with heat and transferred to a Parr flask, where it was hydrogenated at 50 psi of hydrogen over 10% (wt) Pd/C (10 mg cat/65 mg bromohydrin) for 24 hours. Complete debenzylation was confirmed by mass spectrometry. The mixture was filtered through Celite, the filter cake rinsed with isopropanol, and the filtrate concentrated. The residue was dissolved in 1:1 isopropanol/EtOH (c=0.2 M) and brought to reflux for 30 minutes with 0.5 eq of fumaric acid. The reaction was cooled and the solvent removed. The crude material was purified by open column chromatograph or preparative chromatograph.

Column Separation of (R,R)-1 and (S,S)-1, Procedure B.

A sample of 75 mg of fenoterol HBr was dissolved in 1.5 mL of 95/5/0.05 $CH_3CN$/isopropanol/$HNEt_2$ and applied in 100 μL injections to a CHIRALPAK® AD-H 10×250 mm 5 μm semi-preparative column using a waters 2690 Separations Module, PDA set to 280 nm. The eluting solvent was 95/5/0.05 $CH_3CN$/isopropanol/$HNEt_2$, 5 mL/min. Retention times for (S,S) and (R,R) isomers were 4.8 min and 7.8 min, respectively.

(R,R)-(−)-Fenoterol [(R,R)-1].

Obtained according to Procedure B to give 40 mg collected after evaporation. $^1$H NMR ($CD_3OD$) δ 1.05 (d, 3H, J=6.3 Hz), 2.49 (q, 1H, J=6.9 Hz), 2.62-2.74 (m, 2H), 2.80-2.91 (m, 2H), 4.55 (dd, 1H, J=5.1, J=3.3 Hz), 6.16 (t, 1H, J=2.4 Hz), 6.27 (d, 2H, J=2.1 Hz), 6.68 (d, 2H, J=8.4 Hz), 6.94 (d, 2H, J=8.4 Hz); $^{13}$C NMR ($CD_3CN$) δ 20.3, 43.2, 55.1, 55.2, 72.4, 102.2, 105.4, 116.0, 131.3, 131.8, 147.4, 156.2, 159.0; UV (MeOH) $\lambda_{max}$ 279 nm (ε 2,760), 225 (12,900), 204 (32,600); MS (APCI+) m/z (rel): 304 (100, M+H); $[\alpha]_D$=−29.0° (conc=0.2% MeOH); HPLC: (a) 0.1% diethylamine in $H_2O$, 0.50 mL/min, 254 nm, $t_R$ 2.90 min, 99% pure; (d) $t_R$ 7.8 min, >99% pure.

(S,S)-(+)-Fenoterol [(S,S)-1].

Obtained according to Procedure B to give 35 mg after evaporation. $^1$H NMR ($CD_3OD$) δ 1.05 (d, 3H, J=6.6 Hz), 2.49 (q, 1H, J=7.2 Hz), 2.62-2.76 (m, 2H), 2.80-2.94 (m, 2H), 4.55 (dd, 1H, J=4.8, J=3.3 Hz), 6.16 (t, 1H, J=2.1 Hz), 6.27 (d, 2H, J=2.4 Hz), 6.68 (d, 2H, J=8.4 Hz), 6.94 (d, 2H, J=8.4 Hz); $^{13}$C ($CD_3CN$) δ 20.3, 43.2, 55.0, 55.2, 72.4, 102.2, 105.4, 116.0, 131.3, 131.8, 147.4, 156.2, 159.0; UV (MeOH) $\lambda_{max}$ 279 nm (ε 2,680), 224 (12,700), 204 (32,800); MS (APCI+) m/z (rel): 304 (100, M+H); $[\alpha]_D$=+28.5° (conc=0.20% MeOH); HPLC: (a) 0.1% diethylamine in $H_2O$, 0.50 mL/min, 254 nm, $t_R$ 2.72 min, >99% pure; (d) $t_R$ 4.8 min, >99% pure.

(R,S)-(−)-Fenoterol Fumarate [(R,S)-1].

Prepared from (R)-8 and (S)-10 according to Procedure A to give 168 mg (64%). $^1$H NMR ($CD_3OD$) δ 1.22 (d, 3H, J=6.6 Hz), 2.64 (dd, 1H, J=9.9 Hz, J=13.2 Hz), 3.01-3.51 (m, 4H), 4.79 (dd, 1H, J=3.0 Hz, J=9.9 Hz), 6.23 (t, 1H, J=2.4 Hz), 6.36 (d, 2H, J=2.1 Hz), 6.75 (s, 1H), 6.76 (d, 2H, J=8.4 Hz), 7.05 (d, 2H, J=8.1 Hz); $^{13}$C NMR ($CD_3OD$) δ 16.2, 39.1, 52.5, 57.4, 70.4, 103.4, 105.3, 116.7, 127.8, 131.4, 135.2, 144.6, 157.7, 160.0, 168.2; UV (MeOH) $\lambda_{max}$ 278 nm (ε 2,520), 205 (27,900); MS (ESI+) m/z (rel): 304 (100, M+H); $[\alpha]_D$=−7.5° (conc=0.75% MeOH); HPLC: (a) 70/30/0.05. 1.00 mL/min, 282 nm, $t_R$ 1.35 min, >99% pure; (b) 50/50/0.05. 1.0 ml, 0.50 mL/min, 254 nm, $t_R$ 2.72 min, >99% pure; (d) $t_R$ 4.8 min, 1.00 mL/min, 280 nm, $t_R$ 2.10 min, 97.5% pure.

(S,R)-(+)-Fenoterol Fumarate [(S,R)-1].

Prepared from (S)-8 and (R)-10 according to Procedure A to give 104 mg (39%). $^1$H NMR ($CD_3OD$) δ 1.22 (d, 3H, J=6.6 Hz), 2.64 (dd, 1H, J=9.9 Hz, J=13.5 Hz), 3.47-3.04 (m, 4H), 4.80 (dd, 1H, J=2.7, J=9.6 Hz), 6.23 (t, 1H, J=2.4 Hz), 6.36 (d, 2H, J=2.1 Hz), 6.75 (s, 1H), 6.76 (d, 2H, J=8.4 Hz), 7.05 (d, 2H, J=8.4 Hz); $^{13}$C NMR ($CD_3OD$) δ 16.2, 39.1, 52.5, 57.4, 70.4, 103.4, 105.3, 116.7, 127.8, 131.4, 135.2, 144.6, 157.7, 159.9, 168.2; UV (MeOH) $\lambda_{max}$ 278 nm (ε 2,640), 202 (36,600); MS (ESI+) m/z (rel): 304 (100, M+H), 413 (10); $[\alpha]_D$=+6.4° (conc=0.50% MeOH); HPLC: (a) 70/30/0.05, 1.00 mL/min, 282 nm, $t_R$ 1.35 min, 95.9% pure; (b) 50/50/0.05, 1.0 mL/min, 280 nm, $t_R$ 2.06 min, 99% pure.

(R,R)-(−)-1-p-Methoxyphenyl-2-(β-3',5'-dihydroxy-phenyl-β-oxy)ethylamino-propane Fumarate [(R,R)-2].

Prepared from (R)-8 and (R)-11 according to Procedure A to give 172 mg (38%). $^1$H NMR ($CD_3OD$) δ 1.08 (d, 3H, J=6.3 Hz), 3.05-2.56 (m, 5H), 4.57 (dd, 1H, J=8.4, 5.4 Hz), 6.16 (m, 1H), 6.26 (d, 2H, J=2.7 Hz), 6.81 (d, 2H, J=8.7 Hz), 7.03 (d, 2H J=8.7 Hz); $^{13}$C NMR ($CD_3OD$) δ 18.8, 42.3, 54.5, 55.6, 56.0, 72.6, 103.0, 105.4, 115.0, 131.1, 131.2, 131.3, 146.2, 159.8, 159.9; UV (MeOH) $\lambda_{max}$ 277 nm (ε 3,590), 224 (17,700), 207 (29,500); MS (ESI+) m/z (rel): 318 (100, M+H); $[\alpha]_D$=−24.9° (c=0.8 MeOH); HPLC: (a) 70/30/0.05, 1.0 mL/min, 282 nm, $t_R$ 1.54 min, 96.5% pure; (b) 50/50/0.05, 2.0 mL/min, 276 nm, $t_R$ 1.51 min, 95.9% pure.

(S,S)-(+)-1-p-Methoxyphenyl-2-(β-3',5'-dihydroxy-phenyl-(β-oxy)ethylamino-propane Fumarate [(S,S)-2].

Prepared from (S)-8 and (S)-11 according to Procedure A to give 318 mg (53%). $^1$H NMR ($CD_3OD$) δ 1.15 (d, 3H, J=6.0 Hz), 2.58-3.22 (m, 5H), 3.77 (s, 3H), 4.68 (dd, 1H, J=4.8, 8.4 Hz), 6.18 (t, 1H, J=2.1 Hz), 6.31 (d, 2H, J=2.1 Hz), 2.23 (s, 0.5 H, fumarate), 6.84 (d, 2H, J=8.7 Hz), 7.10 (d, 2H, J=9.0 Hz); $^{13}$C NMR ($CD_3OD$) δ 16.1, 39.9, 52.4, 54.5, 55.3, 70.4, 101.9, 104.2, 114.0, 129.2, 130.1, 144.4, 158.7, 158.9; UV (MeOH) $\lambda_{max}$ 277 nm (ε 2,100), 224 (11,00), 205 (22,700); MS (ESI+) m/z (rel): 318 (100, M+H); $[\alpha]_D$=+28.6° (c=0.95 MeOH); HPLC: (a) 70/30/0.05, 1.0 mL/min, 282 nm, $t_R$ 1.67 min, 96.0% pure; (b) 50/50/0.05, 2.0 mL/min, 276 nm, $t_R$ 1.51 min, 97.1% pure.

(R,S)-(+1p-Methoxyphenyl-2-(β-3',5'-dihydroxy-phenyl-(β-oxy)ethylaminopropane Fumarate [(R,S)-2].

Prepared from (R)-8 and (S)-11 according to Procedure A to give 160 mg (38%). $^1$H NMR ($CD_3OD$) δ 1.20 (d, 3H, J=6.6 Hz), 2.62-2.71 (m, 1H), 2.98-3.20 (m, 3H), 3.30-3.42 (m, 2H), 4.73-4.81 (m, 1H), 6.21 (m, 2H), 3.35 (m, 2H), 6.71 (s, 0.5H, fumarate), 6.56-6.89 (m, 2H), 7.11-7.19 (m, 2H); $^{13}$C NMR ($CD_3OD$) δ 15.6, 38.5, 51.8, 54.5, 55.9, 69.7, 102.1, 104.1, 114.1, 128.5, 130.2, 136.0, 143.8, 158.8, 159.1; UV (MeOH) $\lambda_{max}$ 277 nm (ε 4,100), 224 (21,400), 203 (50,600); MS (ESI+) m/z (rel): 318 (100, M+H); $[\alpha]_D$=−7.2° (c=1.5 MeOH); HPLC: (a) 70/30/0.05, 1.00 mL/min, 282 nm, $t_R$ 1.40 min, 99% pure; (b) 50/50/0.05, 2.0 mL/min, 276 nm, $t_R$ 1.51 min, 96.1% pure.

(S,R)-(+)-1-p-Methoxyphenyl-2-(β-3',5'-dihydroxyphenyl-β-oxy)ethylaminopropane Fumarate [(S,R)-2].

Prepared from (S)-8 and (R)-11 according to Procedure A to give 200 mg (51%). $^1$H NMR ($CD_3OD$) δ 1.12 (d, 3H, J=6.0 Hz), 2.58-3.13 (m, 5H), 3.77 (s, 3H), 4.62 (dd, 1H, J=3.6, 9.0 Hz), 6.15 (m, 1H), 6.30 (d, 2H, J=1.8 Hz), 6.85 (d, 2H, J=8.7 Hz), 7.11 (d, 2H, J=8.7 Hz); $^{13}$C NMR ($CD_3OD$) δ 18.2, 41.4, 54.1, 55.7, 56.5, 64.7, 103.0, 105.3, 115.1, 130.7, 131.3, 145.9, 159.8, 160.0; UV (MeOH) $\lambda_{max}$ 277 nm (ε 3,150), 224 (3,310), 205 (30,600); MS (ESI+) m/z (rel): 318 (100, M+H); $[\alpha]_D$=+14.1° (c=0.95 MeOH); HPLC: (a) 70/30/0.05, 1.00 mL/min, 282 nm, $t_R$ 1.42 min, 97.7% pure; (b) 50/50/0.05, 2.0 mL/min, 276 nm, $t_R$ 1.52 min, 97.8% pure.

(R,R)-(+5-{2-[2-(4-Aminophenyl)-1-methylethylamino]-1-hydroxyethyl}-1,3-benzenediol Fumarate [(R,R)-3].

Prepared from (R)-8 and (R)-12 according to Procedure A to give 88 mg (42%). $^1$H NMR ($CD_3OD$) δ 1.23 (m, 3H), 2.70-3.24 (m, 4H), 3.54 (m, 1H), 4.84 (dd, 1H, J=3.3, 9.6 Hz), 6.23 (t, 1H, J=2.4 Hz), 6.38 (d, 2H, J=2.1 Hz), 6.75 (s, 2H, fumarate), 7.35 (dd, 4H, J=8.1, 21.0 Hz); $^{13}$C ($CD_3OD$) δ 15.5, 39.6, 52.7, 56.6, 70.3, 103.4, 105.3, 123.8, 132.0, 132.1, 135.2, 137.5, 144.7, 160.0, 168.1; UV (MeOH) $\lambda_{max}$ 284 nm (ε 1,520), 206 (21,700); MS (ESI+) m/z (rel): 303 (100, M+H); $[\alpha]_D$=−6.8° (conc=1.0% MeOH); HPLC: (a) 80/20/0.05, 0.70 mL/min, 276 nm, $t_R$ 2.07 min, 95.5% pure; (b) 50/50/0.05, 1.0 mL/min, 282 nm, $t_R$ 2.60, 97.16% pure.

(S,S)-(+)-5-{2-[2-(4-Aminophenyl)-1-methylethylamino]-1-hydroxyethyl}-1,3-benzenediol Fumarate [(S,S)-3].

Prepared from (S)-8 and (S)-12 according to Procedure A to give 56 mg (25%). $^1$H NMR (CD$_3$OD) δ 1.23 (m, 3H), 2.62-3.27 (m, 4H), 3.55 (m, 1H), 4.74-4.88 (m, 1H), 6.22 (t, 1H, J=1.8 Hz), 6.37 (d, 2H, J=2.4 Hz), 6.75 (s, 2H, fumarate), 7.32 (dd, 4H, J=8.7, 25.8 Hz); $^{13}$C NMR (CD$_3$OD) δ 15.5, 39.6, 52.5, 56.7, 70.7, 103.4, 105.3, 123.3, 131.8, 132.0, 135.2, 136.9, 144.7, 160.0, 168.1; UV (MeOH) $\lambda_{max}$ 284 nm (ε 1,720), 207 (28,400); MS (ESI+) m/z (rel): 303 (100, M+H), 329 (20); $[\alpha]_D$=+11.1° (conc=0.50% MeOH); HPLC: (a) 80/20/0.05, 0.7 mL/min, 276 nm, $t_R$ 2.01 min, <99% pure; (b) 50/50/0.05, 1.0 mL/min, 282 nm, $t_R$ 2.50 min, 99.4% pure.

(R,S)-(+5-{2-[2-(4-Aminophenyl)-1-methylethylamino]-1-hydroxyethyl}-1,3-benzenediol Fumarate [(R,S)-3].

Prepared from (R)-8 and (S)-12 according to Procedure A to give 72 mg (35%). $^1$H NMR (CD$_3$OD) δ 1.23 (m, 3H), 2.73-3.24 (m, 4H), 3.51 (m, 1H), 4.80 (dd, 1H, J=2.7, 9.6 Hz), 6.22 (t, 1H, J=2.1 Hz), 6.36 (d, 2H, J=2.4 Hz), 6.75 (s, 2H, fumarate), 7.32 (dd, 4H, J=8.4, 25.2 Hz); $^{13}$C NMR (CD$_3$OD) δ 16.1, 39.12, 5.16, 56.9, 70.4, 103.4, 105.3, 123.4, 132.0, 132.0, 135.2, 136.8, 144.6, 160, 168.10; UV (MeOH) $\lambda_{max}$ 284 nm (ε 1,620), 205 (27,200); MS (ESI+) m/z (rel): 303 (100, M+H), 134 (14); $[\alpha]_D$=−7.5° (conc=0.50% MeOH); HPLC: (a) 80/20/0.05, 0.7 mL/min, 276 nm, $t_R$ 2.08 min, 95.0% pure; (b) 50/50/0.05, 1.0 mL/min, 282 nm, $t_R$ 2.51 min, 97.4% pure.

(S,R)-(+)-5-{2-[2-(4-Aminophenyl)-1-methylethylamino]-1-hydroxyethyl}-1,3-benzenediol Fumarate [(S,R)-3].

Prepared from (S)-8 and (R)-12 according to Procedure A to give 93 mg (42%). $^1$H NMR (CD$_3$OD) δ 1.23 (d, 3H, J=6.3 Hz), 2.70-3.78 (m, 4H), 3.42-3.62 (m, 1H), 4.80 (dd, 1H, J=3.0, 9.9 Hz), 6.22 (t, 1H, J=2.1 Hz), 6.37 (d, 2H, J=2.1 Hz), 6.75 (s, 2H, fumarate), 7.33 (dd, 4H, J=8.4, 26.7 Hz); $^{13}$C NMR (CD$_3$OD) δ 16.2, 39.1, 52.6, 56.9, 70.5, 103.4, 105.3, 123.5, 132.1, 133.7, 135.2, 137.1, 144.7, 160.0, 168.1 UV (MeOH) $\lambda_{max}$ 284 nm (ε 8,230), 207 (100,000); MS (ESI+) m/z (rel): 303 (100, M+H), 134 (18); $[\alpha]_D$=+11.4° (conc=0.50% MeOH); HPLC: (a) 70/30/0.05, 1.00 mL/min, 280 nm, $t_R$ 1.45 min, 99% pure; (b) 50/50/0.05, 1.0 mL/min, 282 nm, $t_R$ 2.63 min, 95.33% pure.

(R,R)-(+5-[1-Hydroxy-2-(1-methyl-2-phenylethylamino) ethyl]-1,3-benzenediol fumarate [(R,R)-4].

Prepared from (R)-8 and (R)-13 according to Procedure A to give 92 mg (26%). $^1$H NMR (CD$_3$OD) δ 1.22 (m, 3H), 2.68-3.28 (m, 2H), 3.10-3.28 (m, 2H), 3.53 (br-m, 1H), 4.75-4.80 (m, 1H), 6.24 (t, 1H, J=2.4 Hz), 6.38 (d, 2H, J=2.1 Hz), 6.75 (s, 1H, fumarate), 7.22-7.33 (m, 5H); $^{13}$C NMR (CD$_3$OD) δ 15.5, 40.3, 56.9, 70.2, 103.4, 105.3, 128.3, 129.9, 130.3, 135.2, 137.3, 144.6, 144.6, 159.9, 168.1; UV (MeOH) $\lambda_{max}$ 277 nm (ε 926), 204 (18,700); MS (APCI+) m/z (rel): 288 (100, M+H); $[\alpha]_D$=−21.2° (conc=0.85% MeOH); HPLC: (a) 50/50/0.05, 1.00 mL/min, 282 nm; $t_R$ 1.73 min; 99% pure; (b) 50/50/0.05, 2.0 mL/min, 276 nm, $t_R$ 1.46 min, 97.5% pure.

(S,S)-(+)-5-[1-Hydroxy-2-(1-methyl-2-phenylethylamino)ethyl]-1,3-benzenediol fumarate [(S,S)-4].

Prepared from (S)-8 and (S)-13 according to Procedure A to give 184 mg (51%). $^1$H NMR (CD$_3$OD) δ 1.21 (m, 3H), 2.70-3.13 (m, 2H), 3.15-3.23 (m, 2H), 3.54 (br-m, 1H), 4.79-4.86 (m, 1H), 6.24 (t, 1H, J=2.1 Hz), 6.39 (t, 2H, J=2.7 Hz), 6.76 (s, 1H, fumarate), 7.22-7.32 (m, 5H); $^{13}$C NMR (CD$_3$OD) δ 15.5, 40.3, 56.9, 70.2, 103.4, 105.3, 128.3, 129.9, 130.3, 135.1, 137.3, 144.6, 144.6, 159.9, 168.1 UV (MeOH) $\lambda_{max}$ 278 nm (ε 1,510), 207 (26,600); MS (APCI+) m/z 288 (100, M+H); $[\alpha]_D$=+19.3° (conc=0.90% MeOH); HPLC: (a) 50/50/0.05, 1.00 mL/min, 282 nm, $t_R$ 1.49 min; 98.4% pure; (b) 50/50/0.05, 2.0 mL/min, 276 nm, $t_R$ 1.35 min, 99% pure.

(R,S)-(+5-[1-Hydroxy-2-(1-methyl-2-phenylethylamino)ethyl]-1,3-benzenediol fumarate [(R,S)-4].

Prepared from (R)-8 and (S)-13 according to Procedure A to give 170 mg (45%). $^1$H NMR (CD$_3$OD) δ 1.22 (m, 3H), 2.68-3.28 (m, 2H), 3.13-3.28 (m, 2H), 3.53 (br-m, 1H), 4.76-4.80 (m, 1H), 6.23 (t, 1H, J=2.1 Hz), 6.37 (t, 2H, J=3.0 Hz), 6.75 (s, 1H, fumarate), 7.24-7.37 (m, 5H); $^{13}$C NMR (CD$_3$OD) δ 16.3, 24.2, 39.8, 57.2, 70.5, 103.4, 105.3, 128.4, 130.0, 130.4, 135.2, 137.4, 144.6, 160.1 UV (MeOH) $\lambda_{max}$ 278 nm (ε 1,110), 205 (31,000); MS (APCI+) m/z (rel): 288 (100, M+H); $[\alpha]_D$=−6.9° (conc=0.85% MeOH); HPLC: (a) 50/50/0.05, 1.00 mL/min, 282 nm, $t_R$ 1.53 min, 99% pure; (b) 50/50/0.05, 2.0 mL/min, 276 nm, $t_R$ 1.46 min, 98.5% pure.

(S,R)-(+)-5-[1-Hydroxy-2-(1-methyl-2-phenylethylamino)ethyl]-1,3-benzenediol fumarate [(S,R)-4].

Prepared from (S)-8 and (R)-13 according to Procedure A to give 212 mg (59%). $^1$H NMR (CD$_3$OD) δ 1.22 (m, 3H), 2.72 (dd, 1H J=10.2, 13.2 Hz), 3.11 (dd, 1H, J=10.2, 12.6 Hz), 3.18-3.27 (m, 2H), 3.48-3.61 (m, 1H), 4.83 (dd, 1H, J=3.3, 9.9 Hz), 6.22 (t, 1H, J=2.4 Hz), 6.36 (d, 2H, J=2.4 Hz), 6.75 (s, 1H, fumarate), 7.24-7.37 (m, 5H); $^{13}$C NMR (CD$_3$OD) δ 16.3, 24.2, 39.8, 57.2, 70.5, 103.4, 105.3, 128.4, 130.0, 130.4, 135.2, 137.4, 144.6, 160.1; UV (MeOH) $\lambda_{max}$ 278 nm (ε 1,680), 206 (35,500); MS (APCI+) m/z (rel): 288 (100, M+H), 270 (19, M-OH); $[\alpha]_D$=+9.1° (conc=1.1%, MeOH); HPLC: (a) 50/50/0.05, 1.00 mL/min, 282 nm, $t_R$ 1.51 min, 99% pure; (b) 50/50/0.05, 2.0 mL/min, 276 nm, $t_R$ 1.43 min, 99% pure.

(R,R)-(+5-{1-hydroxy-2-[1-methyl-2-(1-naphthyl)ethylamino]ethyl}-1,3-benzenediol fumarate [(R,R)-5].

Prepared from (R)-8 and (R)-14 according to Procedure A to give 135 mg (46%). $^1$H NMR (CD$_3$OD) δ 1.18-1.23 (m, 3H), 3.16-3.34 (m, 1H, 2H), 3.69-3.74 (m, 2H), 4.78-4.80 (m, 1H), 6.23 (t, 1H, J=2.4 Hz), 6.38 (m, 2H), 7.41-7.61 (m, 4H), 7.83 (d, 1H, J=7.5 Hz), 7.90 (d, 1H, J=7.8 Hz), 8.10 (m, 1H); $^{13}$C NMR (CD$_3$OD) δ 16.2, 37.2, 54.5, 56.1, 70.3, 103.4, 105.3, 124.3, 126.5, 127.0, 127.7, 129.3, 130.1, 133.2, 135.2, 135.6, 144.7, 160.1, 168.2; UV (MeOH) $\lambda_{max}$ 282 nm (ε 5,860), 224 (50,900), 208 (35,500); MS (APCI+) m/z (rel): 338 (100, M+H), 169 (15, fragment); $[\alpha]_D$=−20.4 (conc=0.50% MeOH); HPLC: (a) 60/40/0.05, 1.00 mL/min, 282 nm, $t_R$ 2.08 min, 95.7% pure; (b) 50/50/0.05, 1.5 mL/min, 282 nm, $t_R$ 2.20 min, 99% pure.

(S,S)-(+)-5-{1-hydroxy-2-[1-methyl-2-(1-naphthyl)ethylamino]ethyl}-1,3-benzenediol fumarate [(S,S)-5].

Prepared from (S)-8 and (S)-14 according to Procedure A to give 118 mg (40%)$^1$H NMR (CD$_3$OD) δ 1.13-1.17 (m, 3H), 3.14-3.26 (m, 1H, 2H), 3.61-3.76 (m, 2H), 4.44-4.75 (m, 1H), 6.18 (t, 1H, J=2.4 Hz), 6.33 (m, 2H), 7.36-7.52 (m, 4H), 7.77 (dd, 1H, J=1.8, 7.5 Hz), 7.84 (d, 1H, J=8.1 Hz), 8.04 (t, 1H, J=8.4 Hz); $^{13}$C NMR (CD$_3$OD) δ 16.1, 37.1, 54.4, 56.0, 70.3, 103.3, 105.3, 124.3, 126.5, 127.0, 127.7, 129.2, 130.0, 133.2, 135.2, 135.7, 144.5, 160.0, 168.1; UV (MeOH) $\lambda_{max}$ 282 nm (ε 6,210), 223 (56,400), 208 (42,700); MS (APCI+) m/z (rel): 338 (100, M+H), 169 (8, fragment); $[\alpha]_D$=+20.0° (conc=1.1% MeOH); HPLC: (a) 60/40/0.05, 1.00 mL/min, 282 nm, $t_R$ 2.35 min, 98.9% pure; (b) 50/50/0.05, 1.5 mL/min, 282 nm, $t_R$ 2.26 min, 97.2% pure.

(R,S)-(+5-{1-hydroxy-2-[1-methyl-2-(1-naphthyl)ethylamino]ethyl}-1,3-benzenediol fumarate [(R,S)-5].

Prepared from (R)-8 and (S)-14 according to Procedure A to give 114 mg (39%). $^1$H NMR (CD$_3$OD) δ 1.08-1.11 (m, 3H), 3.02-3.24 (m, 1H, 2H), 3.54-3.68 (m, 2H), 4.45-4.75 (m, 1H), 6.11 (t, 1H, J=1.8 Hz), 6.26 (m, 2H), 6.63 (s, 2H fumarate), 7.28-7.48 (m, 4H), 7.70 (d, 1H, J=7.5 Hz), 7.77 (d, 1H, J=7.8 Hz), 7.97 (t, 1H, J=7.8 Hz); $^{13}$C NMR (CD$_3$OD) δ 16.0, 37.1, 52.5, 56.0, 70.4, 103.4, 105.3, 124.4, 126.5, 127.0, 127.6, 129.2, 130.1, 133.1, 135.2, 135.5, 144.7, 159.9, 168.2; UV (MeOH) $\lambda_{max}$ 281 nm (ε 12,600), 224 (61,900), 204 (47,200); MS (APCI+) m/z (rel): 338 (100, M+H), 190 (15, fragment); $[\alpha]_D$=−11.3° (conc=0.85% MeOH); HPLC: (a) 60/40/0.05, 1.00 mL/min, 282 nm, $t_r$ 2.30 min, 98.6% pure; (b) 50/50/0.05, 1.5 mL/min, 282 nm, $t_R$ 2.36 min, 99% pure.

(S,R)-(+)-5-{1-hydroxy-2-[1-methyl-2-(1-naphthyl)ethylamino]ethyl}-1,3-benzenediol fumarate [(S,R)-5].

Prepared from (S)-8 and (R)-14 according to Procedure A to give 123 mg (42%). $^1$H NMR (CD$_3$OD) δ 1.18-1.22 (m, 3H), 3.10-3.28 (m, 1H, 2H), 3.69-3.78 (m, 2H), 4.45-4.75 (m, 1H), 6.23 (t, 1H, J=2.1 Hz), 6.39 (m, 2H), 6.73 (s, 2H fumarate), 7.39-7.59 (m, 4H), 7.80 (d, 1H, J=7.5 Hz), 7.88 (d, 1H, J=7.8 Hz), 8.01 (t, 1H, J=9.0 Hz); $^{13}$C NMR (CD$_3$OD) δ 16.4, 37.4, 52.5, 56.2, 70.6, 103.4, 105.3, 124.4, 126.5, 127.0, 129.3, 130.1, 133.1, 133.4, 135.6, 136.3, 144.8, 160.0, 171.4; UV (MeOH) $\lambda_{max}$ 282 nm (ε 7,740), 224 (70,900), 206 (55,800); MS (ESI+) m/z (rel): 338 (100, M+H); $[\alpha]_D$=+15.5 (conc=1.0% MeOH) HPLC: (a) 60/40/0.05, 1.0 mL/min, 282 nm, $t_R$ 1.95, 95.7% pure; (b) 50/50/0.05, 1.5 mL/min, 282 nm, $t_R$ 2.29 min, 95.7% pure.

(R,R)-(+5-[1-Hydroxy-2-(1-methylhexylamino)ethyl]-1,3-benzenediol Fumarate [(R,R)-6].

Prepared from (R)-8 and (R)-15 according to Procedure A to give 45 mg (29%). $^1$H NMR (CD$_3$OD) δ 0.920 (t, 3H, J=6.9 Hz), 1.30 (d, 3H, J=6.9 Hz), 1.29-1.64 (m, 8H), 3.01-3.18 (m, 2H), 3.14-3.30 (m, 1H), 4.80 (dd, 1H, J=3.3, 9.6 Hz), 6.22 (t, 1H, J=2.1 Hz), 6.36 (d, 2H, J=2.4 Hz), 6.75 (s, 1H, fumarate); $^{13}$C NMR (CD$_3$OD) δ 14.3, 16.0, 23.5, 26.2, 32.6, 34.2, 52.1, 55.7, 70.2, 103.3, 105.3, 135.2, 144.7, 160.0, 168.0; UV (MeOH) $\lambda_{max}$ 278 nm (ε 931), 203 nm (20,100); MS (ESI+) m/z (rel): 268 (100, M+H); $[\alpha]_D$=−8.8° (conc=1.1% MeOH); HPLC: (c) 70/30/0.1, 1.0 mL/min, 276 nm, $t_R$ 2.18 min, 96.6% pure; (b) 50/50/0.05, 1.0 mL/min, 279 nm, $t_R$ 2.06 min, 98.9% pure.

(S,S)-(+)-5-[1-Hydroxy-2-(1-methylhexylamino)ethyl]-1,3-benzenediol Fumarate [(S,S)-6].

Prepared from (S)-8 and (S)-15 according to Procedure A to give 96 mg (43%). $^1$H NMR (CD$_3$OD) δ 0.923 (t, 3H, J=6.6 Hz); 1.31 (d, 3H, J=6.6 Hz), 1.26-1.84 (m, 8H), 2.01-3.18 (m, 2H), 3.14-3.30 (m, 1H), 4.81 (dd, 1H, J=3.3, 9.6 Hz), 6.23 (t, 1H, J=2.4 Hz), 6.39 (d, 2H, J=2.1 Hz), 6.76 (s, 1H, fumarate); $^{13}$C NMR (CD$_3$OD) δ 14.2, 16.0, 23.4, 26.3, 32.6, 34.1, 52.1, 55.8, 70.2, 103.4, 105.3, 135.2, 144.7, 159.9, 168.2; UV (MeOH) $\lambda_{max}$ 278 nm (ε 1,340), 203 (28,800); MS (APCI+) m/z (rel): 268 (100, M+H); $[\alpha]_D$=+10.8° (conc=0.50% MeOH); HPLC: (c) 70/30/0.1, 1.0 mL/min, 276 nm, $t_R$ 2.16 min, 97.0% pure; (b) 50/50/0.05, 1.0 mL/min, 279 nm, $t_R$ 2.11 min, 99% pure.

(R,S)-(+5-[1-Hydroxy-2-(1-methylhexylamino)ethyl]-1,3-benzenediol Fumarate [(R,S)-6].

Prepared from (R)-8 and (S)-15 according to Procedure A to give 83 mg (38%). $^1$H NMR (CD$_3$OD) δ 0.924 (m, 3H); 1.32 (d, 3H, J=6.6 Hz), 1.26-1.84 (m, 8H), 2.98-3.20 (m, 2H), 3.32-3.22 (m, 1H), 4.78 (dd, 1H, J=3.0, 9.9 Hz), 6.23 (t, 1H, J=2.1 Hz), 6.37 (d, 2H, J=1.8 Hz), 6.76 (s, 1H, fumarate); $^{13}$C NMR (CD$_3$OD) δ 14.2, 16.4, 23.4, 26.2, 32.6, 33.5, 52.2, 56.0, 70.4, 103.4, 105.3, 135.2, 144.7, 160.0, 168.1; UV (MeOH) $\lambda_{max}$ 276 nm (ε 2,770), 203 (35,900); MS (APCI+) m/z (rel): 268 (100, M+H); $[\alpha]_D$=−15.9° (conc=0.70% MeOH); HPLC: (c) 70/30/0.1, 1.0 mL/min, 276 nm, $t_R$ 2.16 min, 97.0% pure; (b) 50/50/0.05, 1.0 mL/min, 279 nm, $t_R$ 2.07 min, 96.2% pure.

(S,R)-(+)-5-[1-Hydroxy-2-(1-methylhexylamino)ethyl]-1,3-benzenediol Fumarate [(S,R)-6].

Prepared from (S)-8 and (R)-15 according to Procedure A to give 81 mg (38%). $^1$H NMR (CD$_3$OD) δ 0.920 (t, 3H, J=6.3 Hz), 1.32 (d, 3H, J=6.9 Hz), 1.30-1.77 (m, 8H), 2.99-3.17 (m, 2H), 3.23-3.26 (m, 1H), 4.76 (dd, 1H, J=3.0, 9.6 Hz), 6.22 (t, 1H, J=2.4 Hz), 6.36 (d, 2H, J=2.1 Hz), 6.75 (s, 1H, fumarate); $^{13}$C NMR (CD$_3$OD) δ 14.2, 16.5, 23.5, 26.2, 32.6, 39.5, 52.2, 56.0, 70.4, 103.4, 105.3, 135.2, 144.7, 160.0, 168.0; UV (MeOH) $\lambda_{max}$ 278 nm (ε 1,440), 204 (29,900); MS (APCI+) m/z (rel): 268 (100, M+H); $[\alpha]_D$=+12.7° (conc=1.0% MeOH); HPLC: (c) 70/30/0.1, 1.0 mL/min, 276 nm, $t_R$ 2.16 min, 99% pure; (b) 50/50/0.05, 1.0 mL/min, 279 nm, $t_R$ 2.02 min, 95.7% pure.

(R)-(−)-5-(1-Hydroxy-2-phenethylaminoethyl)-1,3-benzenediol fumarate [(R)-7].

Prepared from (R)-8 and 28 to give 37 mg (15%). $^1$H NMR (CD$_3$OD) δ 2.94-3.23 (m, 6H), 4.73 (dd, 1H, J=3.3, 9.9 Hz), 6.15 (t, 1H, J=2.4 Hz), 6.29 (d, 2H, J=1.8 Hz), 7.19-7.28 (m, 5H), 6.69 (s, 1H); UV (MeOH) $\lambda_{max}$ 278 nm (ε 1,360), 205 (32,600); MS (APCI+) m/z (rel): 274 (100, M+H); $[\alpha]_D$=−13.0° (conc=1.0% MeOH); HPLC: (a) 80/20/0.05, 1.00 mL/min, 282 nm, $t_R$ 1.47 min, 96.7% pure; (b) 50/50/0.05, 1.0 mL/min, 272 nm, $t_R$ 2.78 min, 95.1% pure.

(S)-(+)-5-(1-hydroxy-2-phenethylaminoethyl)-1,3-benzenediol fumarate [(S)-7].

Prepared from (S)-8 and 28 to give 51 mg (17%). $^1$H NMR (CD$_3$OD) δ 2.87-3.21 (m, 6H), 4.68 (dd, 1H, J=3.6, 9.9 Hz), 6.10 (t, 1H, J=2.4 Hz), 6.24 (d, 2H, J=2.1 Hz), 6.63 (s, 1H), 7.12-7.21 (m, 5H); UV (MeOH) $\lambda_{max}$ 278 nm (ε 1,280), 204 (33,700); MS (APCI+) m/z (rel): 274 (100, M+H); $[\alpha]_D$=+14.64° (conc=1.1% MeOH); HPLC: (a) 80/20/0.05, 1.00 mL/min, 282 nm, $t_R$ 1.47 min, 98.6% pure; (b) 50/50/0.05, 1.0 mL/min, 272 nm, $t_R$ 2.74 min, 98.8% pure.

(R,R)-(−)-ethylfenoterol.

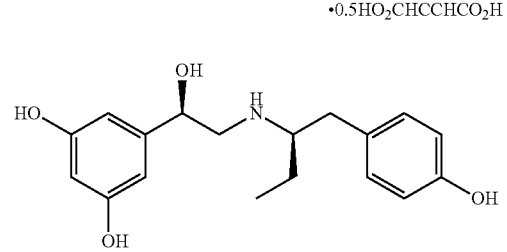 [SMILES: CC[C@H](Cc1ccc(O)cc1)NC[C@H](O)c1cc(O)cc(O)c1]

•0.5HO$_2$CHCCHCO$_2$H $^1$H NMR: (300 MHz, CD$_3$OD): δ 0.950 (t, 3H, J=7.5 Hz), 1.67 (m, 2H), 2.83-3.18 (m, 4H), 3.33-3.40 (m, 1H), 3.37 (s, 4H), 4.82 (m, 1H), 6.24 (d, 1H, J=2.1 Hz), 6.37 (d, 2H, J=1.8 Hz), 6.73 (s, 2H, fum), 6.76 (d, 2H, J=8.4 Hz), 7.05 (d, 2H, J=8.7 Hz) ppm. CMR: $^{13}$C (75 MHz, CD$_3$OD): δ 9.43, 23.28, 36.56, 52.29, 62.16, 70.02, 103.4, 105.3, 116.7, 127.8, 131.3, 136.5, 144.6, 157.6, 159.9, 172.3 ppm. UV: (Methanol, $\lambda_{max}$ (ε): 206 nm (22,500), 223 (12,300), 278 (2,460). MS: (LCQ DUO ESI positive ion mass spectrum) M/z (rel): 318 (100, M+H). HPLC 1: Column: Varian Sunfire C18 100×4.6; 70/30/0.1 water/acetonitrile/TFA; 1.0 mL/min; Det: 278 nm; 2.76 min (fumarate, 6.99%), 3.57 min (90.11%); Purity: 97.1%. HPLC 2: Column: Chiralpak IA 250×10; 90/10/0.05 acetonitrile/methanol/TFA; 2.0 mL/min; Det: 278 nm; 5.26 (RR isomer, 92.37%), 7.11 min (fumarate, 5.02%); Purity 97.5%. Specific Rotation: $[\alpha]_D=-15.6$ (free amine, 0.5% MeOH).

(R,S)-(−)-ethylfenoterol.

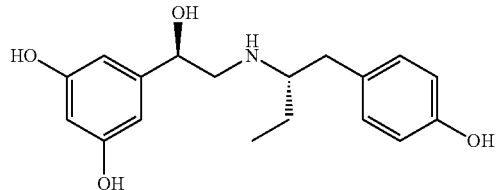

·0.5HO$_2$CHCCHCO$_2$H $^1$H NMR: (300 MHz, CD$_3$OD): δ 0.972 (t, 3H, J=7.5 Hz), 1.70 (p, 2H, J=6.9 Hz)), 2.86-3.22 (m, 4H), 3.32-3.37 (m, 1H), 3.34 (s, 4H), 4.82 (m, 1H), 6.25 (t, 1H, J=2.1 Hz), 6.36 (d, 2H, J=1.8 Hz), 6.74 (s, 2H, fum), 6.77 (d, 2H, J=8.4 Hz), 7.08 (d, 2H, J=8.7 Hz) ppm. CMR: $^{13}$C (75 MHz, CD$_3$OD): δ 9.820, 24.16, 36.48, 52.30, 62.32, 69.92, 103.3, 105.3, 116.8, 127.7, 131.3, 136.1, 144.4, 157.6, 159.8, 171.3 ppm. UV: (Methanol), $\lambda_{max}$ (ε): 204 nm (26,900), 224 (11,500), 278 (2,320). MS: (LCQ DUO ESI positive ion mass spectrum) M/z (rel): 318 (100, M+H). HPLC 1: Column: Varian Sunfire C18 100×4.6; 70/30/0.1 water/acetonitrile/TFA; 1.0 mL/min; Det: 278 nm; 2.79 min (fumarate, 3.34%), 3.56 min (96.11%); Purity: 99.5% HPLC 2: Column: Chiralpak IA 250×10; 90/10/0.05 acetonitrile/methanol/TFA; 2.0 mL/min; Det: 278 nm; 5.88 (RS isomer, 97.08%), 7.12 min (fumarate, 2.92%); Purity >99%. Specific Rotation: $[\alpha]_D=-7.2$ (free amine, 0.5% MeOH).

$C_{22}H_{25}NO_4 \cdot 0.5C_4H_4O_4$

·0.5HO$_2$CCH=CHCO$_2$H

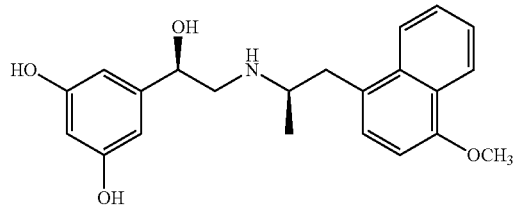

$^1$H NMR: (300 MHz, CD$_3$OD): δ 1.22 (t, 3H, J=6.6 Hz), 3.09-3.21 (m, 3H), 3.59-3.69 (m, 2H), 3.99 (s, 3H), 4.74-4.83 (m, 1H), 6.23 (t, 1H, J=2.4 Hz), 6.37 (dd, 2H, J=2.4, 5.7 Hz), 6.74 (s, 1H), 6.86 (d, 1H, J=7.8 Hz), 7.32 (d, 1H, J=7.8 Hz), 7.48 (t, 1H, J=6.9 Hz), 7.56 (t, 1H, J=6.9 Hz), 8.02 (dd, 1H, J=8.4, 12.0 Hz), 8.27 (d, 1H, J=8.7 Hz) ppm. CMR: $^{13}$C (75 MHz, CD$_3$OD): δ 15.78, 36.66, 52.39, 55.96, 70.20, 103.4, 104.5, 105.3, 123.8, 124.3, 124.9, 126.2, 127.4, 128.1, 129.5, 133.8, 135.2, 144.6, 156.6, 160.0, 168.3 ppm. UV: (Methanol), $\lambda_{max}$ (ε): 298 nm (4,970), 286 (9,920), 234 (22,600), 210 (42,500). MS: (LCQ DUO ESI positive ion mass spectrum) M/z (rel): 368 (100, M+H). Specific Rotation: $[\alpha]_D=-28.8$ (Free Amine; 0.5% MeOH).

$C_{22}H_{25}NO_4 \cdot 0.5C_4H_4O_4$

·0.5HO$_2$CCH=CHCO$_2$H

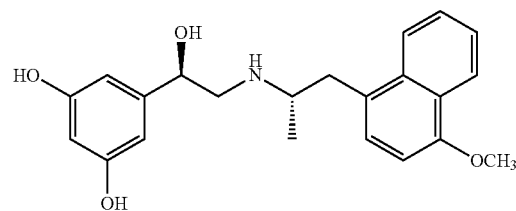

$^1$H NMR: (300 MHz, CD$_3$OD): δ 1.20 (t, 3H, J=6.6 Hz), 3.07-3.21 (m, 3H), 3.52-3.75 (m, 2H), 3.97 (s, 3H), 4.69-4.83 (m, 1H), 6.24 (t, 1H, J=2.1 Hz), 6.39 (dd, 2H, J=2.4, 5.4 Hz), 6.74 (s, 1H), 6.84 (d, 1H, J=7.8 Hz), 7.31 (d, 1H, J=8.1 Hz), 7.48 (t, 1H, J=6.9 Hz), 7.56 (t, 1H, J=6.9 Hz), 8.01 (dd, 1H, J=8.4, 13.5 Hz), 8.27 (d, 1H, J=7.8 Hz) ppm. CMR: $^{13}$C (75 MHz, CD$_3$OD): δ 15.77, 36.64, 52.37, 55.94, 70.46, 103.4, 104.5, 105.3, 123.8, 124.3, 124.9, 126.2, 127.4, 128.1, 129.4, 133.8, 135.5, 144.7, 156.6, 160.0, 169.0 ppm. UV: (Methanol), $\lambda_{max}$ (ε): 298 nm (5,430), 286 (5,710), 233 (25,100), 210 (43,200). MS: (LCQ DUO ESI positive ion mass spectrum) M/z (rel): 368 (100, M+H). Specific Rotation: $[\alpha]_D=-15.8$ (Free Amine; 0.5% MeOH).

A step in the synthesis of the 4 stereoisomers of 1-6 was the coupling of the epoxide formed from either (R)- or (S)-3',5'-dibenzyloxyphenylbromohydrin with the (R)- or (S)-enantiomer of the appropriate benzyl-protected 2-amino-3-benzylpropane (1-5) or the (R)- or (S)-enantiomer of N-benzyl-2-aminoheptane (6), Scheme I.

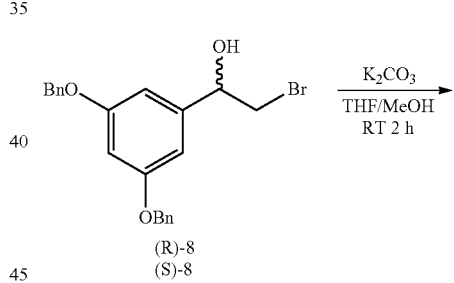

(R)-8
(S)-8

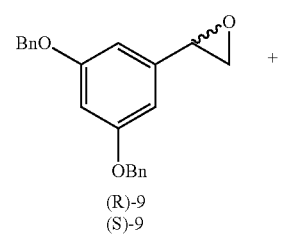

(R)-9
(S)-9

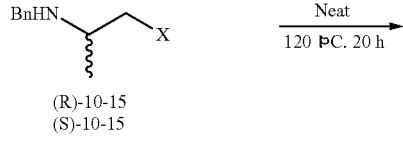

(R)-10-15
(S)-10-15

-continued

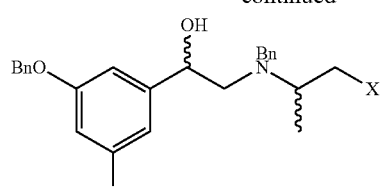

(R, R)-16-21
(S, S)-16-21
(R, S)-16-21
(S, R)-16-21

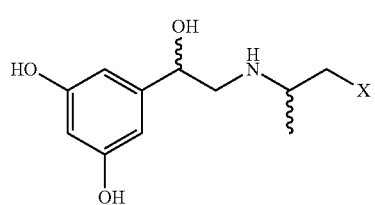

(R, R)-22-27
(S, S)-22-27
(R, S)-22-27
(S, R)-22-27

X =

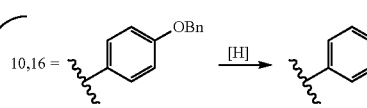  10,16 =

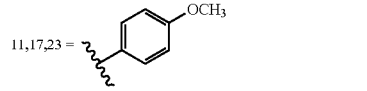  11,17,23 =

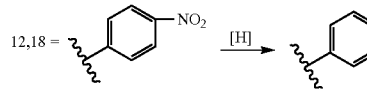  12,18 =

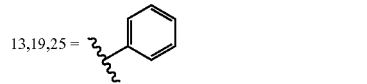  13,19,25 =

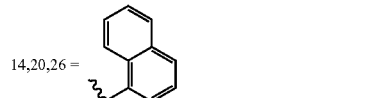  14,20,26 =

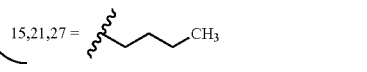  15,21,27 =

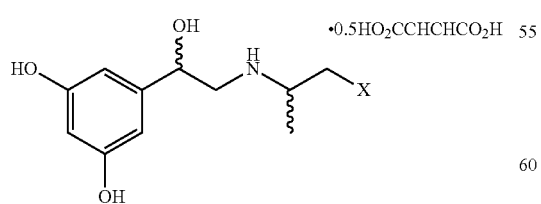

(R, R)-1-6
(S, S)-1-6
(R, S)-1-6
(S, R)-1-6

-continued

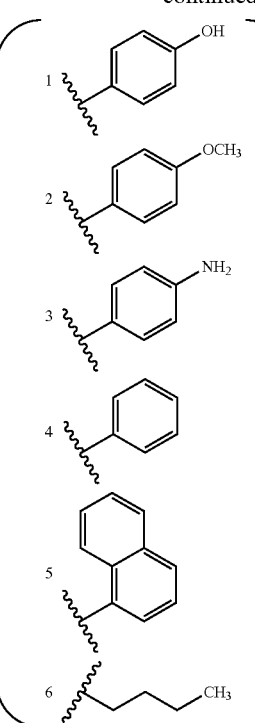

X =

1
2
3
4
5
6

Figure 6:
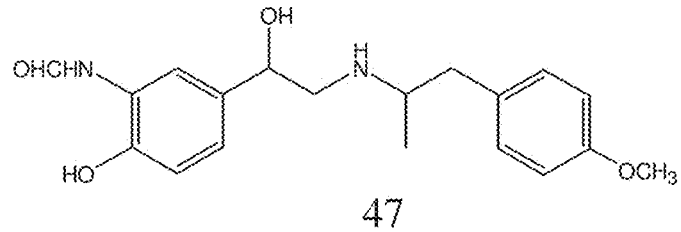
FIG. 6 illustrates the chemical structures of compounds 47-51.
Figure 6:
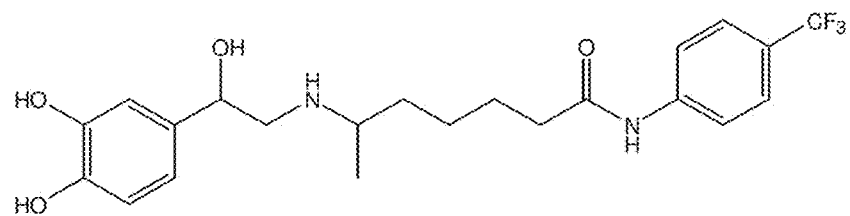
Figure 6:
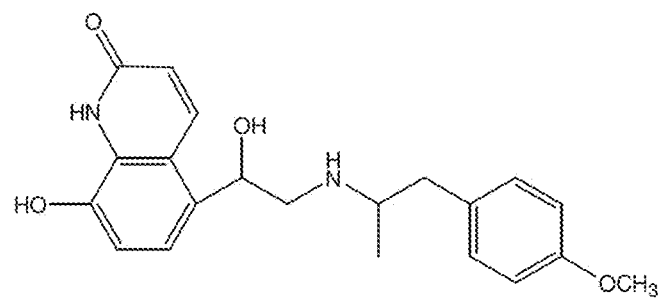
Figure 6:
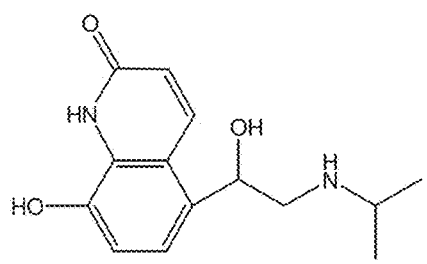
Figure 6:
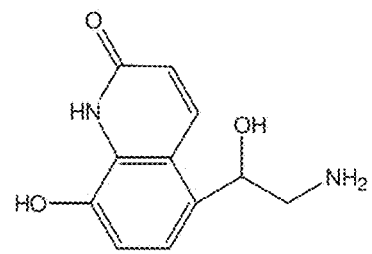

The synthesis of (R)-7 and (S)-7 was accomplished using 2-phenethylamine, Scheme II. This approach was similar to the one developed by Trofast et al. (*Chirality* 3: 443-450, 1991) for the synthesis of the stereoisomers of formoterol, compound 47, FIG. 6. The resulting compounds were then deprotected by hydrogenation over Pd/C and purified as the fumarate salts.

Scheme II

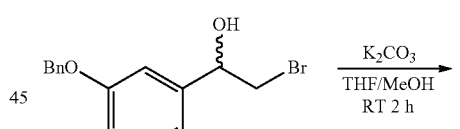

(R)-8
(S)-8

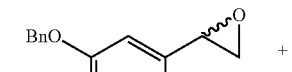

(R)-9
(S)-9

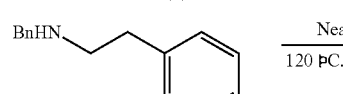

28

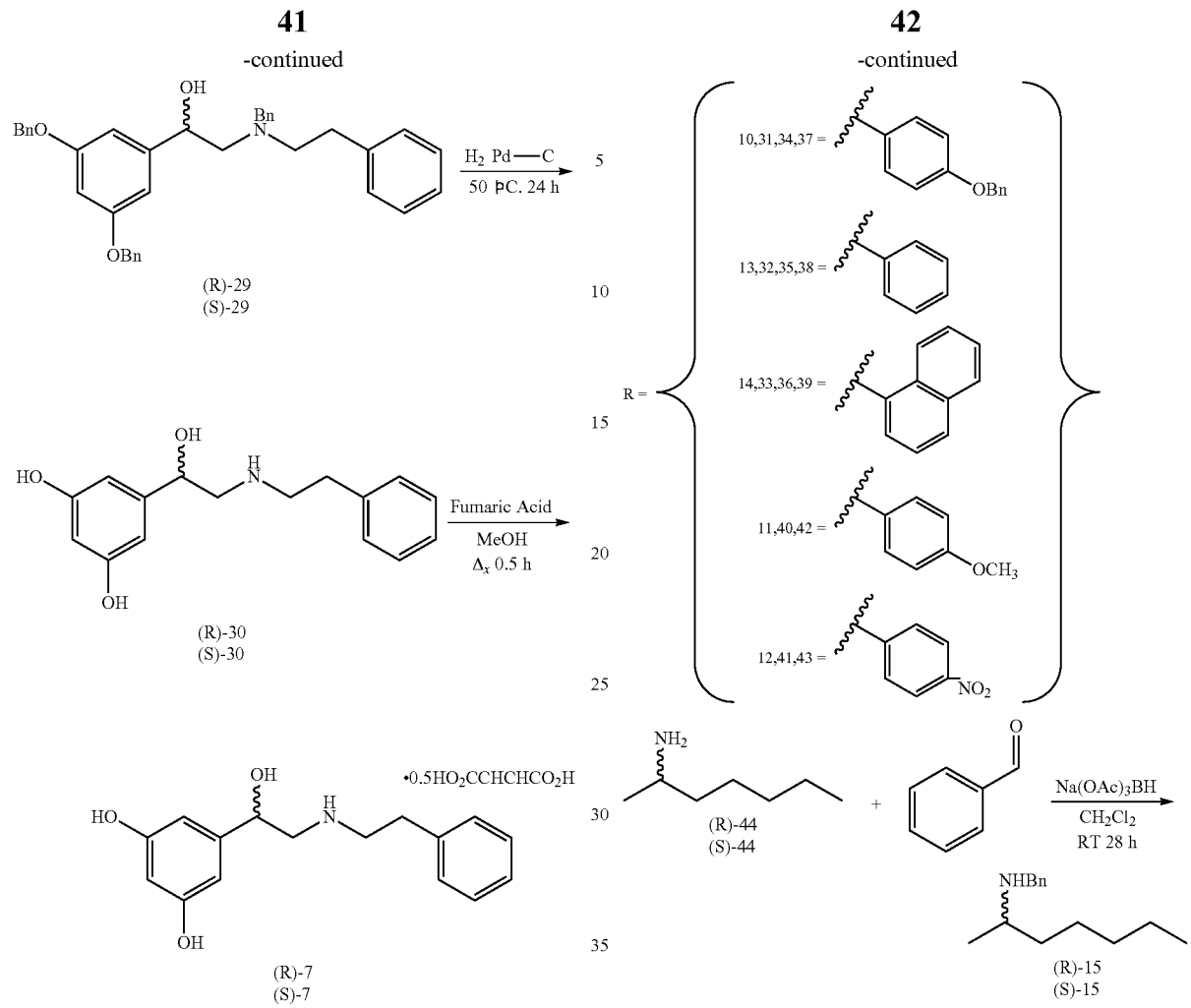

The chiral building blocks used in the syntheses were produced using Scheme III. The (R)- and (S)-3',5'-dibenzyloxyphenyl-bromohydrin enantiomers were obtained by the enantiospecific reduction of 3,5-dibenzyloxy-α-bromoacetophenone using boron-methyl sulfide complex (BH$_3$SCH$_3$) and either (1R,2S)- or (1S,2R)-cis-1-amino-2-indanol. The required (R)- and (S)-2-benzylaminopropanes were prepared by enantioselective crystallization of the rac-2-benzylaminopropanes using either (R)- or (S)-mandelic acid as the counter ion.

Scheme III

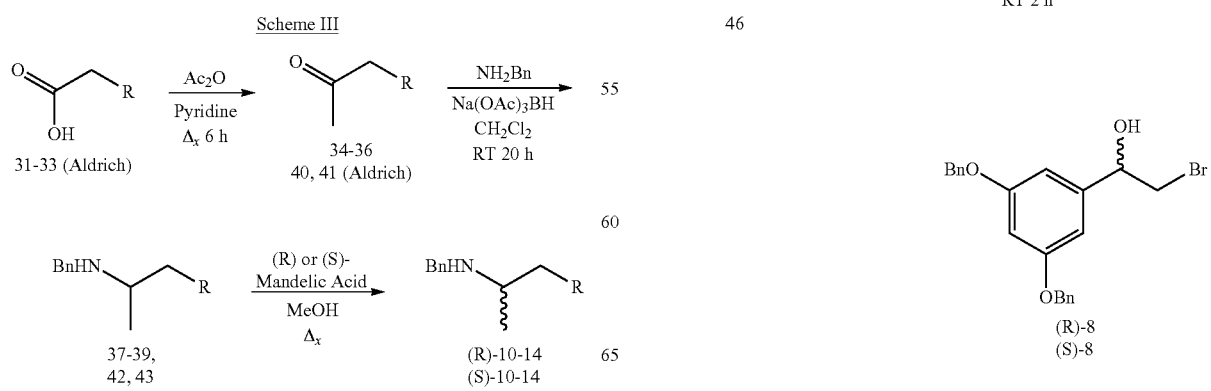

Example 6

Binding Affinities of Exemplary Fenoterol Analogues for β1 and β2 Adrenergic Receptors This example demonstrates that fenoterol analogues have an equivalent if not greater binding affinity for β2-adrenergic receptors than fenoterol.

Compounds were tested up to three times each to determine their binding affinities at the $\beta_1$- and $\beta_2$-adrenergic receptors. Competition curves with standard and unknown compounds included at least six concentrations (in triplicate). For each compound, graphs were prepared containing individual competition curves obtained for that test compound. $IC_{50}$ values and Hill coefficients were calculated using GraphPad Prism® software. $K_i$ values were calculated using the Cheng-Prusoff transformation (*Biochem Pharmacol* 22: 3099-3108, 1973). In each experiment, a standard compound was simultaneously run on the 96-well plate. If the standard compound did not have an $IC_{50}$ value close to the established average for that compound, the entire experiment was discarded and repeated again.

$\beta_1$-adrenergic receptor binding was done on rat cortical membrane following a previously described procedure (Beer et al., *Biochem. Pharmacol.* 37: 1145-1151, 1988). In brief, male Sprague-Dawley rats weighing 250-350 g were decapitated and their brains quickly removed. The cerebral cortices were dissected on ice, weighed and promptly transferred to a 50 ml test tube containing approximately 30 ml of 50 mM Tris-HCl, pH 7.8 (at room temperature). The tissues were homogenized with a polytron and centrifuged at 20,000×g for 12 min at 4° C. The pellet was washed again in the same manner and resuspended at a concentration of 20 mg (original wet wt) per 1 ml in the assay buffer (20 mM Tris-HCl, 10 mM $MgCl_2$, 1 mM EDTA, 0.1 mM ascorbic acid at pH 7.8). To block the $\beta_2$ sites present in the cortical membrane preparation, 30 nM ICI 118-551 was also added to the assay buffer. To wells containing 100 μl of the test drug and 100 μl of [$^3$H]CGP-12177 (1.4 nM final concentration), 0.8 ml of tissue homogenate was added. After 2 hours at 25° C., the incubation was terminated by rapid filtration. Nonspecific binding was determined by 10 μM propranolol.

HEK 293 cells stability transfected with cDNA encoding human $\beta_2$-AR (provided by Dr. Brian Kobilka, Stanford Medical Center, Palo Alto, Calif.) were grown in Dulbecco's Modified Eagle Medium (DMEM) containing 10% fetal bovine serum (FBS), 0.05% penicillin-streptomycin, and 400 μg/ml G418 as previously described (Pauwels et al., *Biochem. Pharmacol.* 42: 1683-1689, 1991). The cells were scraped from the 150×25 mm plates and centrifuged at 500×g for 5 minutes. The pellet was homogenized in 50 mM Tris-HCl, pH 7.7, with a Polytron, centrifuged at 27,000×g, and resuspended in the same buffer. The latter process was repeated, and the pellet was resuspended in 25 mM Tris-HCl containing 120 mM NaCl, 5.4 mM KCl, 1.8 mM $CaCl_2$, 0.8 mM $MgCl_2$, and 5 mM glucose, pH 7.4. The binding assays contained 0.3 nM [$^3$H]CGP-12177 in a volume of 1.0 ml. Nonspecific binding was determined by 1 μM propranolol.

According to the above-described methods, binding affinities, expressed as $K_i$ values, were determined using membranes obtained from a HEK 293 cell line stably transfected with cDNA encoding human $\beta_2$-AR (Pauwels et al., *Biochem. Pharmacol.* 42: 1683-1689, 1991) with [$^3$H] CGP-12177 as the marker ligand. The resulting $IC_{50}$ values and Hill coefficients were calculated for each test compound using GraphPad Prism® software and $K_i$ values were cal-culated using the Cheng-Prusoff transformation (*Biochem Pharmacol* 22: 3099-3108, 1973):

$$K_i = IC_{50}/(1+L/K_d) + \text{Eqn. 1.}$$

Where: L is the concentration of [$^3$H]CGP-12177 and $K_d$ is the binding affinity of the [$^3$]CGP-12177. Each test compounds was assayed three times.

Figure 5:
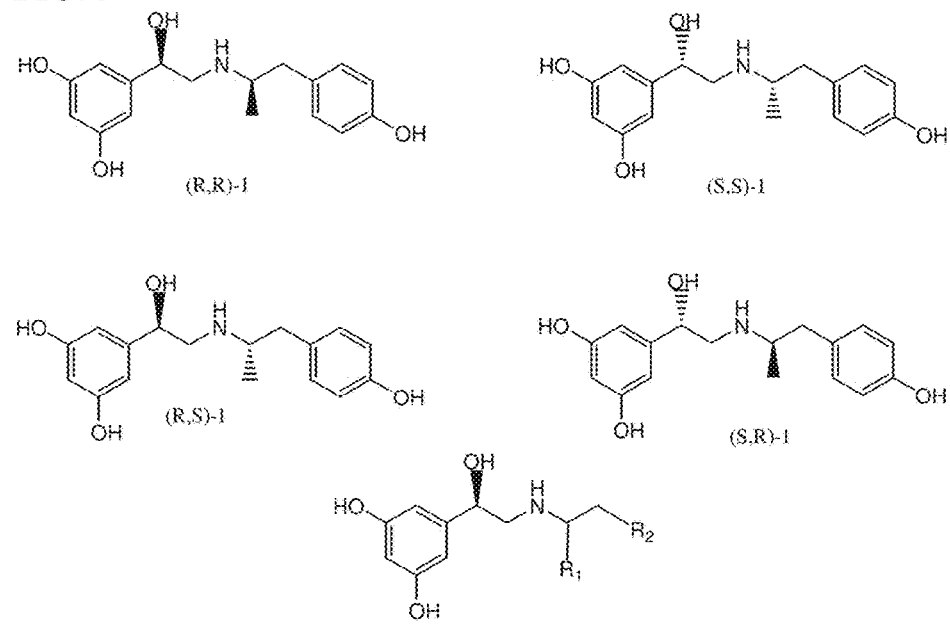
FIG. 5 illustrates the chemical structures of the stereoisomers of fenoterol and fenoterol analogs (compounds 2-7).

The relative binding affinities to the $\beta_2$-AR for the stereoisomers of compounds 1-4 and 6 were R,R>R,S>S, R≈S,S (FIG. 5; Table 1, below). This stereoselectivity is consistent with the previously reported potencies of the formoterol stereoisomers (Trofast et al., *Chiralty* 3: 443-450, 1991) and results from binding studies with the isoproterenol derivative PTFAM, compound 48, FIG. 6 (Eimerl et al., *Biochem. Pharmacol.* 36: 3523-3527, 1987). With compound 5, no significant difference was found between the $K_i$ values of the R,R and R,S isomers, thus the order was R,R=R,S>S,R>S,S. The $K_i$ value for (R)-7 was greater than that of (S)-7, which is consistent with the established enantioselective binding preference for $\beta_2$-ARs with the R-configuration at the stereogenic center containing the β-OH moiety, c.f. (Eimerl et al., *Biochem. Pharmacol.* 36: 3523-3527, 1987; Wieland et al., *Proc. Natl. Acad. Sci. USA* 93: 9276-9281, 1996; Kikkawa et al., *Mol. Pharmacol.* 53: 128-134, 1998; and Zuurmond et al., *Mol. Pharmacol.* 56: 909-916, 1999).

TABLE 1

The binding affinities to the $\beta_2$-AR of the compounds synthesized in this study calculated as $K_i \pm$ SEM (nM), n = 3. Comparison of $\beta_1$- and $\beta_2$ adrenergic binding affinity of fenoterol isomers

| Compound | $K_i \beta_1$ | $K_i \beta_2$ | $K_i \beta_1/K_i \beta_2$ |
|---|---|---|---|
| (R,R)-1 | 14750 ± 2510 | 345 ± 34 | 43 |
| (R,S)-1 | 18910 ± 2367 | 3695 ± 246 | 5 |
| (S,R)-1 | >100,000 | 10330 ± 1406 | NC |
| (S,S)-1 | >100,000 | 27749 ± 6816 | NC |
| (R,R)-2 | 21992 ± 3096 | 474 ± 35 | 46 |
| (R,S)-2 | 30747 ± 6499 | 1930 ± 135 | 16 |
| (S,R)-2 | 33378 ± 9170 | 5269 ± 509 | 6 |
| (S,S)-2 | >100,000 | 15881 ± 2723 | NC |
| (R,R)-3 | 24956 ± 2100 | 2934 ± 168 | 9 |
| (R,S)-3 | 31324 ± 3485 | 7937 ± 397 | 4 |
| (S,R)-3 | 77491 ± 3583 | 23125 ± 2093 | 3 |
| (S,S)-3 | 31440 ± 1681 | 28624 ± 906 | 1 |
| (R,R)-4 | 17218 ± 1270 | 1864 ± 175 | 9 |
| (R,S)-4 | 33047 ± 2779 | 6035 ± 434 | 4 |
| (S,R)-4 | >100,000 | 30773 ± 3259 | NC |
| (S,S)-4 | >100,000 | 28749 ± 1811 | NC |
| (R,R)-5 | 3349 ± 125 | 241 ± 38 | 14 |
| (R,S)-5 | 15791 ± 6269 | 341 ± 23 | 46 |
| (S,R)-5 | 34715 ± 9092 | 1784 ± 148 | 19 |
| (S,S)-5 | >100,000 | 2535 ± 209 | NC |
| (R,R)-6 | 10185 ± 499 | 9275 ± 902 | 1 |
| (R,S)-6 | >100,000 | 31440 ± 1681 | NC |
| (S,R)-6 | 61295 ± 5821 | >100,000 | NC |
| (S,S)-6 | 52609 ± 1434 | 56420 ± 5186 | 1 |
| (R)-7 | 42466 ± 3466 | 10466 ± 1461 | 4 |
| (S)-7 | 52178 ± 3006 | 20562 ± 3721 | 3 |

When just the R,R isomers were compared, (R,R)-5 had the highest relative affinity of the tested compounds, although the difference between (R,R)-5 and (R,R)-1 did not reach statistical significance, Table 1. The only other (R,R) stereoisomer with sub-micromolar affinity was (R,R)-2, which had a significantly lower binding affinity than (R,R)-5, p=0.0051, and (R,R)-1, p=0.0291, although the mean $K_i$ value for (R,R)-2 is only 23% greater than that of (R,R)-1. The minimal effect of transforming the p-OH moiety into a methyl ether is consistent with previous data from Schirrmacher et al. (*Bioorg. Med. Chem. Lett.* 13: 2687-92, 2003).

In the previous study, rac-1 was converted into a [$^{18}$F]-fluoroethoxy ether without significant loss of in vitro activity and it was concluded that, within the accuracy of the experimental measurements, the derivatization did not change the binding affinity of the rac-1 to the $\beta_2$-AR.

Binding affinities, expressed as $K_i$ values, for the $\beta_1$-AR were determined using rat cortical membranes with [$^3$H]-CGP-12177 as the marker ligand (Beer et al., Biochem. Pharmacol. 37: 1145-1151, 1988.). The calculated $K_i$ for (R,R)-5 was 3,349 nM and the binding affinities for the all of the remaining test compounds were >10,000 nM, Table 1. Unlike the data from the $\beta_2$-AR binding studies, there was no clear trend which could be associated with the stereochemistry of the compounds.

The relative selectivity of the compounds for the $\beta_2$-AR and $\beta_1$-AR was determined using the ratio $K_i \beta_1/K_i \beta_2$, Table 1. Of particular interest were the ratios for the four compounds with sub-micromolar affinity for the $\beta_2$-AR, (R,R)-1, (R,R)-2, (R,R)-5 and (R,S)-5, which were 46, 43, 14 and 46, respectively. The results for (R,R)-1 and (R,R)-2 are consistent with previously reported $K_i \beta_1/K_i \beta_2$ ratio of 53 for the $\beta_2$-AR-selective agonist (R,R)-TA-2005, compound 49, FIG. 6.

The observed loss of $\beta_2$-AR selectivity for (R,R)-5 was unexpected as was the 3-fold increase in selectivity displayed by (R,S)-5 relative to (R,R)-5. Previous studies with the stereoisomers of 47 indicated that both the (R,R)- and (R,S)-isomers had a high degree of selectivity for the $\beta_2$-AR, relative to the $\beta_1$-AR, with the selectivity of the (R,R)-isomer greater than that of the (R,S)-isomer (Trofast et al., Chirality 3: 443-450, 1991). This is the case for compounds 1 and 2, but reversed for 5. It is also interesting to note that (S,R)-5 had a similar selectivity (19-fold) and its affinity for the $\beta_2$-AR was only 7-fold weaker than (R,R)-5, 1783 nM and 241 nM, respectively.

These studies demonstrate that (R,R)- or (R,S)-naphthyl fenoterol analogues have a higher binding affinity for $\beta_2$-adrenergic receptors than any isoform of fenoterol. The (R,R)-methyoxy fenoterol analogue has a similar $K_i$ for the $\beta_2$-adrenergic receptor as (R,R)-fenoterol. Thus, such analogues are viable candidates for $\beta_2$-adrenergic receptor agonists and can likely be used to treat disorders that are presently treated with commercially available (±)-fenoterol.

Example 7

Cardiomyocyte Contractility Studies with Fenoterol Analogues

This example illustrates the pharmacological activities of the compounds with sub-micromolar affinity for the $\beta_2$-AR and (R,S)-1 and (S,S)-1.

In these studies, the contraction amplitude indexed by electrical pacing induced shortening of cell length was measured in single ventricular myocytes before and after exposure to a single dose of the test compounds. Contractile response to the agonist was expressed as a percentage of the basal contractility and the specificity of the agonist towards $\beta_2$-adrenergic receptor was determined by the inhibitory effect of ICI 118,551 ($10^{-7}$ mol/L; Tocris Cookson Ltd., Bristol, U.K.), a selective $\beta_2$-AR antagonist.

Figure 7:
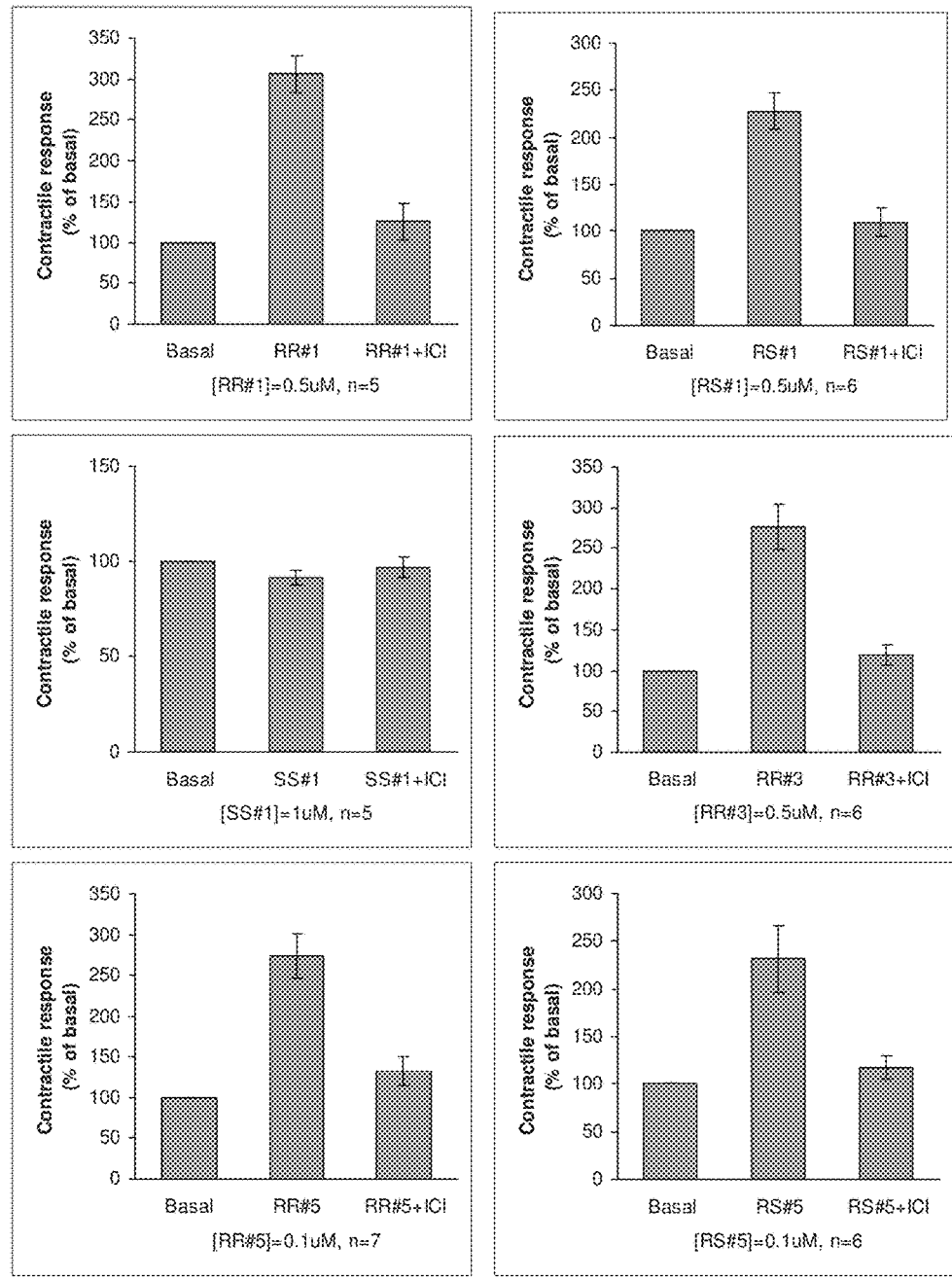
FIG. 7 illustrates the effect of fenoterol and fenoterol analogs on cell contraction in single ventricular myocytes.

All of the compounds tested, except for (S,S)-1, produced a significant contractile response which was blocked by ICI 118,551, while (S,S)-1 had no observed pharmacological effect, FIG. 7. These results were consistent with the results from the previous study (Beigi et al., Chirality, 18: 822-827, 2006) and with the observations that for agonist activity at the $\beta_2$-AR an R-configuration is preferred at the stereogenic center containing the $\beta$-OH moiety, c.f. (Eimerl et al., Biochem. Pharmacol. 36: 3523-3527, 1987; Wieland et al., Proc. Natl. Acad. Sci. USA 93: 9276-9281, 1996; Kikkawa et al., Mol. Pharmacol. 53: 128-134, 1998; and Zuurmond et al., Mol. Pharmacol. 56: 909-916, 1999). It is of interest to note that maximum effect was elicited with 0.1 µM (R,R)-5 and (R,S)-5 while the other active compounds required 0.5 µM concentrations. In addition, while the equivalent activities of (R,R)-5 and (R,S)-5 were suggested by the binding data, the observed activity of (R,S)-1 was unexpected as previous studies of the stereoisomers of 47 (Trofast et al., Chirality 3: 443-450, 1991) and 48 (Eimerl et al., Biochem. Pharmacol. 36: 3523-3527, 1987) indicated that the agonist activities of the (R,R)-isomers were significantly greater than the activities of the corresponding (R,S)-isomers.

Example 8

Comparative Molecular Field Analysis

This example illustrates the use of Comparative Molecular Field Analysis (CoMFA) to analyze the disclosed compounds.

The disclosed compounds were analyzed using Comparative Molecular Field Analysis, a 3D QSAR technique applicable to the analysis of the relative activities of stereoisomers and/or enantiomers at a selected target.

CoMFA was performed as implemented in SYBYL 7.2. (TRIMS Inc., St. Louis, Mo.). Molecular models of all derivatives were prepared in HyperChem v. 6.03 (HyperCube Inc., Gainesville, Fla.) using ModelBuild procedure to ensure the same conformation of the scaffold. Models were extracted to SYBYL and the partial atomic charges (Gasteiger-Huckel type) were calculated. Ligand models were aligned using as a common substructure of the two asymmetric carbon atoms in the core of the fenoterol molecule (—C*—CH$_2$—NH—C*—CH$_2$—). Two types of molecular fields (steric and electrostatic) were sampled on the grid (2 Å spacing) lattice surrounding each structure. Distance-dependent dielectric constant was used in electrostatic calculations and energetic cutoffs of 30 kcal/mol for both the steric and the electrostatic energies were set.

The Partial Least Square correlation procedure applied for resultant database extracted four statistically significant components and the following validation parameters were obtained for the best solution: $R^2$=0.920, $F_{(4,21)}$=60.380, standard error of estimate=0.223, cross-validated (leave-one-out) $R^2$=0.847. In general, electrostatic fields accounts for 48.1% of explained variance and steric fields accounts for 51.9%. The resulting 3D QSAR model shows good statistical correlation with experimental data, $R^2$=0.920 and F=60.380, and good prediction power as indicated by the cross-validated $R^2$ value ($Q^2$)=0.847 and the standard error of prediction (SEP)=0.309, Table 2.

TABLE 2

The pK$_d$ predicted by the CoMFA model.

| Derivative | pKd Measured | pKd Predicted |
| --- | --- | --- |
| (R,R)-1 | 6.46 | 5.84 |
| (R,S)-1 | 5.43 | 5.48 |
| (S,R)-1 | 4.99 | 5.02 |
| (S,S)-1 | 4.56 | 4.66 |
| (R,R)-2 | 6.32 | 6.17 |
| (R,S)-2 | 5.71 | 5.80 |

TABLE 2-continued

The pK$_d$ predicted by the CoMFA model.

| Derivative | pKd Measured | pKd Predicted |
|---|---|---|
| (S,R)-2 | 5.28 | 5.34 |
| (S,S)-2 | 4.80 | 4.99 |
| (R,R)-3 | 5.53 | 5.57 |
| (R,S)-3 | 5.10 | 5.21 |
| (S,R)-3 | 4.64 | 4.75 |
| (S,S)-3 | 4.54 | 4.39 |
| (R,R)-4 | 5.73 | 5.58 |
| (R,S)-4 | 5.22 | 5.25 |
| (S,R)-4 | 4.51 | 4.75 |
| (S,S)-4 | 4.54 | 4.43 |
| (R,R)-5 | 6.62 | 6.72 |
| (R,S)-5 | 6.47 | 6.36 |
| (S,R)-5 | 5.75 | 5.90 |
| (S,S)-5 | 5.60 | 5.54 |
| (R,R)-6 | 5.03 | 5.01 |
| (R,S)-6 | 4.50 | 4.66 |
| (S,R)-6 | 4.00 | 4.19 |
| (S,S)-6 | 4.25 | 3.84 |
| (R)-7 | 4.98 | 5.33 |
| (S)-7 | 4.69 | 4.51 |

In the first stage, the model was used to identify the regions responsible for the discrimination between the stereoisomers. The CoMFA procedure produced several distinct asymmetric regions located in close proximity of each chiral center. The first chiral center (carrying the β hydroxyl group) is surrounded by an electropositive region behind the molecule. An electropositive region can be associated with hydrogen bond formation and indicates favorable donor properties or unfavorable acceptor properties of the pseudoreceptor. In this case, the location of the electropositive field indicates that the orientation of the β-OH moiety behind the plane of the model (the S configuration at the chiral center) would hinder H bond formation with the receptor. The electropositive region is closely associated with a steric unfavorable region behind the first chiral center. This is an additional indication that the model demonstrates a preference for the β-hydroxyl group in the R configuration. The preference for the R configuration at this center is consistent with previous models and experimental data, which demonstrated that the R configuration is favored for functional activity at β-AR receptors (c.f., Eimerl et al., Biochem. Pharmacol. 36: 3523-3527, 1987; Wieland et al., Proc. Natl. Acad. Sci. USA 93: 9276-9281, 1996; Kikkawa et al., Mol. Pharmacol. 53: 128-134, 1998; and Zuurmond et al., Mol. Pharmacol. 56: 909-916, 1999).

The CoMFA model also demonstrated the effect of the second chiral center. The preferred configuration can be derived from the binding data, where for compounds 1-4 and 6 the (R,R)-isomers had the higher affinities relative to their respective (R,S)-isomers, while the K$_i$ values for (R,R)-5 and (R,S)-5 were equivalent, Table 1. Thus, in this model, the more active isomers are those with the methyl moiety on the stereogenic center on the aminoalkyl portion of the molecules pointing out of the plane of the figure of the CoMFA model. This is depicted by a steric disfavoring region behind the second chiral center of the molecule, and indicates a preference for the R configuration at this site.

In this study, only the aminoalkyl portion of the fenoterol molecule was altered and, therefore, the key CoMFA regions are associated with this aspect of the molecule. In the resulting analysis, all four interacting regions were identified in the proximity of the aromatic moiety and all can be used to generate hypotheses concerning the mode of binding action of the studied derivatives.

In the model, the large electropositive region encompassing the area close to the —OH or OCH$_3$ substituents represents H-bond donor properties of the pseudoreceptor to these moieties. These interactions are responsible for the relatively higher binding affinities of the O-derivatives, compounds 1 and 2, relative to compounds 3 and 4, in the latter compound the p-amino substituent should be positively charged under the experimental conditions.

A large electronegative region and another electropositive region, both located parallel on two sides of the aromatic system most likely represent π-π or π-hydrogen bond interactions between the β$_2$-AR and electron-rich aromatic moieties, such as the naphthyl ring. This is consistent with the increased affinity of compounds 1, 2 and 5 relative to the other compounds examined in this study. The role of this interaction is suggested by the observation that the K$_i$ values for (R,R)-5 and (R,S)-5 were equivalent to (R,R)-1 and (R,R)-2, Table 1.

Two steric regions are located close to the electrostatic regions and one favors and the other disfavors bulkiness in the respective areas. This indicates that the binding of the aminoalkyl portions of the molecules are also sterically restricted.

The binding of agonists and antagonists to the β$_2$-AR has been studied using site-directed mutagenesis and molecular modeling techniques (Eimerl et al., Biochem. Pharmacol. 36: 3523-3527, 1987; Wieland et al., Proc. Natl. Acad. Sci. USA 93: 9276-9281, 1996; Kikkawa et al., Mol. Pharmacol. 53: 128-134, 1998; Zuurmond et al., Mol. Pharmacol. 56: 909-916, 1999; Kontoyianni et al., J. Med. Chem. 39: 4406-4420, 1996; Furse et al., J. Med. Chem. 46: 4450-4462, 2003; and Swaminath et al. J. Biol. Chem. 279: 686-691, 2004). There is general agreement that the binding of the "catechol" portion of an agonist occurs within a binding area created by the transmembrane (TM) helices identified as TM3, TM5 and TM6. The binding process is a sequential event that produces conformational changes leading to G-protein activation (Furse et al., J. Med. Chem. 46: 4450-4462, 2003). A key aspect in this process is the interaction of the hydroxyl moiety on the chiral carbon of the agonist with the Asn-293 residue in TM6, and for this interaction an R-configuration is preferable at the chiral carbon (Eimerl et al., Biochem. Pharmacol. 36: 3523-3527, 1987; Kikkawa et al., Mol. Pharmacol. 53: 128-134, 1998; and Swaminath et al. J. Biol. Chem. 279: 686-691, 2004). Since the "catechol" portion of the fenoterol molecule was not altered in this study, it follows that in the CoMFA model, an R-configuration at the first stereogenic center is preferred in most stable complexes.

The majority of the binding and functional studies of β$_2$-AR agonists have been conducted with small N-alkyl substituents such as methyl, isopropyl and t-butyl, c.f. (Kontoyianni et al., J. Med. Chem. 39: 4406-4420, 1996). However, while these compounds are active at the β$_2$-AR, they are not subtype selective. This is illustrated by the K$_i$ β$_1$/K$_i$ β$_2$ ratios determined for compounds 49, 50 and 51 (FIG. 6) which were 53, 1.7 and 1.3, respectively (Kikkawa, et al. Mol. Pharmacol. 53: 128-134, 1998)). The removal of the p-methoxyphenyl moiety not only reduced the selectivity, but also the affinities as the respective β$_2$K$_i$ values were 12 nM, 170 nM and 6300 nM (Kikkawa, et al. Mol. Pharmacol. 53: 128-134, 1998).

The role that aminoalkyl substituents play in β$_2$-AR selectivity has been investigated using site-directed mutagenesis and molecular modeling techniques (Kikkawa, et al. Mol. Pharmacol. 53: 128-134, 1998; Furse et al., J. Med. Chem. 46: 4450-4462, 2003; and Swaminath et al. J. Biol.

*Chem.* 279: 686-691, 2004). Using (R,R)-49 as the model ligand, Kikkawa, et al. determined that hydrogen bond formation between the p-methoxy oxygen on compound 49 and the hydroxyl group of tyrosine 308 (Y308) located in the extracellular end of TM7 was the source of the $\beta_2$-AR selectivity (*Mol. Pharmacol.* 53: 128-134, 1998).

Furse and Lybrand developed a de novo model of the $\beta_2$-AR and investigated molecular complexes of several ligands (agonist and antagonist) with this subtype (*J. Med. Chem.* 46: 4450-4462, 2003). Among the structures investigated, (R,R)-49 has the same aminoalkyl substituent as the compound 2. Examination of the (R,R)-49/$\beta_2$-AR complex revealed that the p-methoxy group oxygen of (R,R)-49 formed a hydrogen bond with the hydroxy group of Y308, which supports the model proposed by Kikkawa, et al. (*Mol. Pharmacol.* 53: 128-134, 1998). The distance between the two oxygen atoms bonded in the model was 3.22 Å. However, the methoxy moiety of the ligand was also located in close proximity to three other polar residues, histidine 296 (H296) in TM6, tryptophan 109 (W109) in TM3 and asparagine 312 (N312) in TM7, each of which can interact with an aromatic group on the aminoalkyl portion of (R,R)-49.

In the Furse and Lybrand model, the distance between the oxygen atom of the ligand and the hydrogen atom of H296 was 5.88 Å and H296 was proposed as an alternative hydrogen bond donor for interaction with the methoxy group of (R,R)-49. Since Y308 and H296 are found only in $\beta_2$-AR, the corresponding residues found in the $\beta_1$-AR are F359 and K347, respectively, the interaction with H296 and Y308 has been proposed as the source of $\beta_1/\beta_2$ selectivity (Furse et al., *J. Med. Chem.* 46: 4450-4462, 2003).

Since the previous studies of $\beta_1/\beta_2$ selectivity utilized (R,R)-49, the subtype selectivity of the (R,R)-stereoisomers of the compounds synthesized in our study were compared to the subtype selectivity of (R,R)-49. The data from this study suggest that hydrogen bond formation between Y308 and/or H296 and the oxygen atom on the p-substituent of the agonist is involved in $\beta_2$-AR selectivity. The interaction is possible with (R,R)-1 and (R,R)-2 and the $K_i$ $\beta_1/K_i$ $\beta_2$ ratios for these compounds are 43 and 46, respectively, which are comparable to the $K_i$ $\beta_1/K_i$ $\beta_2$ ratio of 53 determined for (R,R)-49. The $K_i$ $\beta_1/K_i$ $\beta_2$ ratios for compounds 3, 4, 6 and 7 were <10 and reflect the fact that they do not have the ability to form hydrogen bonds with Y308 or H296. The hydrogen bonding interactions were also suggested by the CoMFA model identifying a large electropositive region surrounding the area close to the —OH or —OCH$_3$ substituents, representing hydrogen-bond donor properties of the pseudoreceptor.

The data from this study also suggest that an aromatic moiety on the aminoalkyl portion of the compound contributes to $K_i$ and subtype selectivity, even if the aromatic moiety is unable to form a hydrogen bond with the receptor. This is demonstrated by the comparison of the $K_i\beta_2$ values for the (R,R)-isomers of compounds 1-5 which were <3,000 nM with $K_i\beta_2$ value of (R,R)-6 which was 9,000 nM and the $K_i\beta_1/K_i$ $\beta_2$ ratios which were ≥9 for 1-5 while compound 6 displayed no subtype selectivity, Table 1. One possible mechanism to explain the data is π-hydrogen bond formation. The cloud of π-electrons of aromatic rings can act as hydrogen bond acceptors, although it has been estimated that the interaction would be about half as strong as a normal hydrogen bond (Levitt and Perutz *J. Mol. Biol.* 201: 751-754, 1998). The higher affinity and subtype selectivity for (R,R)-5 relative to (R,R)-3 and (R,R)-4 or (R)-7 is consistent with the greater π electron distribution in the napthyl ring relative to the other aromatic rings.

The CoMFA model also identified a large electronegative region and another electropositive region, both located parallel to the aromatic system, which are most likely associated with π-π or π-hydrogen bond interactions between the $\beta_2$-AR and electron-rich aromatic moieties, such as the naphthyl ring. Using the model developed by Furse and Lybrand with (R,R)-49 as the interacting ligand, Y308, H296, W109 and N312 were identified as possible sources of π-π and/or π-hydrogen bond interactions. In the $\beta_2$-AR model, the estimated distances between the p-methoxy moiety on (R,R)-49 and W109 and N312 were 4.80 Å and 3.45 Å, respectively. Since W109 and N312 are fully conserved in all β-AR subtypes, the interactions suggested by the CoMFA model may represent the source of the increase affinities for (R,R)-1, (R,R)-2 and (R,R)-5, relative to the other (R,R)-isomers, but not the observed $\beta_1/\beta_2$ selectivity.

The data from this study and the resulting CoMFA model indicate that the binding process of the tested compounds with the $\beta_2$-AR includes the interaction of the chiral center on the aminoalkyl portion of the agonist with a sterically restricted site on the receptor. The existence of a sterically restricted site has been previously suggested from the data obtained in the development of 3D models for agonist and antagonist complexes with the $\beta_2$-AR (Kobilka, *Mol. Pharm.* 65: 1060-1062, 2004). For example, (R,R)-49 and similar compounds with substituents larger than a methyl group at the stereogenic center on the aminoalkyl portion were suggested to produce significant steric interactions that would unfavorably affect the ligand-receptor complexes.

The binding of an agonist to the $\beta_2$-AR has been described as a multistep interrelated process, in which sequential interactions between the agonist and receptor produce corresponding conformational changes (Kobilka, *Mol. Pharm.* 65: 1060-1062, 2004). The CoMFA model reflects the final agonist/$\beta_2$-AR complex and, in order to discern the effect of the steric restricted site, it is necessary to consider the effect that interaction with this site has on the outcome of the binding process. A detailed description of the present CoMFA model is disclosed in Jozwiak et al. (*J. Med. Chem.*, 50 (12): 2903-2915, 2007) which is hereby incorporated by reference in its entirety.

If one assumes that the interaction of the "catechol" portion of the agonist with the binding area created by TM3, TM5 and TM6 (the first binding area), then these interactions will fix the position of the aminoalkyl portion of the agonist relative to the steric restricted site, and perhaps even create this site. In the CoMFA model, the steric restrictions at the site force the methyl moiety at the chiral center of the aminoalkyl portion to point out of the plane of the model.

Due to the free rotation about the N-atom, the configuration at the chiral center bearing the methyl moiety may likely not affect the ability of the molecule to minimize the interaction with the steric restricted site. However, in the minimum energy conformation, e.g., with the methyl group pointing out of the plane of the CoMFA model, the orientation of the remaining segment of the aminoalkyl portion relative to the second binding area would be affected by the stereochemistry. Indeed, R and S configurations would produce mirror image relationships to the second binding area. This situation is illustrated in FIG. 5 where the catechol, first chiral center and the methyl moieties of (R,R)-5 and (R,S)-5 have been overlaid upon each other.

The studies elucidating the source of $\beta_2$-AR selectivity have primarily utilized (R,R)-49 and one previous study of the effect of chirality on subtype selectivity reported that (R,R)-47 had a higher $\beta_2$-AR selectivity than (R,S)-47 (Trofast et al., *Chirality* 3: 443-450, 1991). Thus, the observed equivalent affinities and functional activities of (R,R)-5 and (R,S)-5 at the $\beta_2$-AR and the 3-fold increased $\beta_2$-AR selectivity of (R,S)-5 was an unexpected result. One possible explanation of these results is that the naphthyl moiety of (R,S)-5 does not interact with the site defined by Y308 and H296 and is directed towards and binds to another site on the $\beta_2$-AR. This interaction also conveys or participates in subtype selectivity as well as increased binding affinity and agonist activity. Since the previous models of $\beta_2$-AR selectivity only employed (R,R)-isomers, it is possible that this site has been overlooked.

Another explanation of the data is suggested by the "rocking tetrahedron" chiral recognition mechanism proposed by Sokolov and Zefirov (*Doklady Akademii Nauk SSSR* 319: 1382-1383, 1991). In this approach to molecular chiral recognition, the enantiomeric ligands are secured to a chiral selector by two binding interactions. The interactions must be non-equivalent and directional so that only one orientation is possible. The tethered enantiomers still have conformational mobility and the remaining moieties on the chiral center will sweep out overlapping but not identical steric volumes. Where and to what extent the chiral selector interacts with these steric volumes, determines the enantioselectivity of the process. If the chirality of the chiral selector places the interaction perpendicular to the plane of the ligand, no enantioselectivity is observed. As a deviation from the perpendicular increases, so does the enantioselectivity relative to the R or S configuration.

With (R,R)-5 and (R,S)-5, the interactions with the first binding area and the steric restricted site of the CoMFA model are two non-equivalent and directional interactions that place the remaining constituents on the second chiral center in the same, albeit mirror image, orientation relative to the second binding area. As discussed above, the interactions of the 1-napthyl moieties of compound 5 with Y308 and H296 are believed to be the source of the observed $\beta_2$-AR selectivity. If the 1-naphthyl rings sweep out overlapping but not identical steric volumes, then the observed $K_i\beta_2$ values and subtype selectivity indicate the following: 1) the $K_i\beta_2$-AR values represent the sum total of the $\pi$-hydrogen bond and $\pi$-$\pi$ interactions between the 1-naphthyl moieties and Y308 and H296, as well as additional non-$\beta_2$-AR specific interactions with other residues such as W109 and N312; 2) the steric volume swept out by (R,S)-5 increases the probability of interactions of Y308 and H296 with the $\pi$ cloud of the naphtyl moiety relative to the (R,R)-5; and 3) the steric volume swept out by (R,S)-5 increases the probability of interactions with non-$\beta_2$-AR specific sites relative to (R,S)-5.

The effect of the configuration at the second chiral center and conformational-based chiral selectivity is also illustrated by the affinities and subtype selectivities of (R,R)-3, (R,S)-3 and (R)-7, Table 1. The inversion of the chirality at the second chiral carbon from R to S, reduced the $K_i\beta_2$ value of the (R,S)-3/$\beta_2$-AR complex relative to the (R,R)-3/$\beta_2$-AR complex by ~3-fold while there was no significant difference between their $K_i\beta_1$ values. The increased subtype selectivity observed for (R,R)-3 relative to (R,S)-3, 9 versus 4, respectively, essentially reflects the differences in $K_i\beta_2$ values, which could be a reflection of increased conformational energy required to bring the aromatic portion of the aminoalkyl chain into contact with the electropositive and electronegative regions that comprise the second binding area or a decrease in the probability that this interaction would occur.

The removal of the methyl moiety on the second chiral center, and thereby the chirality at this site ((R)-7), had a similar effect as inverting the chirality at this site from R to S. The $K_i\beta_2$ values for (R)-7 was 32% higher than (R,S)-3 and there was no difference in the $\beta_2$-AR selectivity, Table 1. These results suggest that for compound 3, the primary effect of the R configuration at the second chiral site was to direct the aminoalkyl chain towards the second binding area which increased the probability of interacting with this site and reduces the conformational energy required to achieve this interaction.

A difference between compounds 3 and 5 is the steric areas swept out by the aromatic substituents. In the case of compound 3, the phenyl ring produces a smaller, more linear area, while with compound 5, the 1-naphthyl ring system produces a relatively larger and broader area. These differences can be used to guide the synthesis of additional derivatives.

In an example, (R,R)-2 and (R,S)-5 are chosen as possible candidates for the development of a new selective $\beta_2$-AR agonist. These compounds may have increased and extended systemic exposures relative to the commercially available rac-1 due to changes in molecular hydrophobicity, metabolic profile and transporter interactions.

The present example provides a pharmacophore model which may be used as a structural guide for the design of new compounds with $\beta_2$-AR selectivity which can be tested for use in the treatment of a desired condition, including congestive heart failure.

Example 9

Pharmacokinetic Studies of (R,R)-Fenoterol, (R,R)-Methoxyfenoterol and (R,S)-Naphtylfenoterol This example demonstrates the plasma concentrations of (R,R)-Fenoterol, (R,R)-Methoxyfenoterol and (R,S)-Naphtylfenoterol administered as an intravenous (IV) bolus to male Sprague-Dawley rats.

(R,R)-Fenoterol, (R,R)-Methoxyfenoterol and (R,S)-Naphtylfenoterol were administered to jungular vein cannulated (JVC) rats at a single dosage of 5 mg/ml intravenously (see Table 3). Dose calculations (mg/kg) were based on the individual body weight measured on the day of treatment. Study duration for pharmacokinetic studies was 6 hours. Plasma samples were collected over six hours at the following nine timepoints: prior to administration of the desired dose; 5.00-5.30 minutes after dose; 15.00-16.30 minutes after dose; 30.00-33.00 minutes after dose; 60-65 minutes after dose; 120-125 minutes after dose; 240-245 minutes after dose; 300-305 minutes after dose; and 360-365 minutes after dose. Urine was collected for 0-6 hours and 6 to 24 hours from 3 rats in each treatment group.

TABLE 3

Study conditions for measuring plasma concentrations of (R,R)-fenoterol, (R,R)-methoxyfenoterol and (R,S)-naphtylfenoterol.

| Compound: | Dose level (mg/kg): | Dose Concentration (mg/ml): | No. of Rats: | No. of Rats for plasma analysis: |
|---|---|---|---|---|
| (R,R)-fenoterol | 5 | 2.5 | 6 | 5 |
| (R,R)-methoxyfenoterol | 5 | 2.5 | 6 | 5 |
| (R,S)-naphtylfenoterol | 5 | 2.5 | 6 | 2 |

Pharmacokinetic parameters for (R,R)-fenoterol, (R,R)-methoxyfenoterol and (R,S)-naphtylfenoterol after intravenous administration to rats (5 mg/kg) were analyzed according to a two-compartment open model (see Table 4). A drug that follows the pharmacokinetics of a two-compartment model does not equilibrate rapidly throughout the body, as is assumed for a one-compartment model. In the two-compartment model, the drug distributes into two compartments, the central compartment and the tissue, or peripheral compartment. The central compartment represents the blood, extracellular fluid, and highly perfused tissues. The drug distributes rapidly and uniformly in the central compartment. A second compartment, known as the tissue or peripheral compartment, contains tissues in which the drug equilibrates more slowly. Drug transfer between the two compartments is assumed to take place by first-order processes.

The following abbreviations are utilized in Table 4 below: alpha—macro rate constant associated with the distribution phase; beta—macro rate constant associated with the elimination phase; A, B—zero time intercept associated with the alpha phase and beta phase, respectively; AUC—area under the curve; T1/2 (K10)—half-life associated with the rate constant K10; K10—elimination rate—rate at which the drug leaves the system from the central compartment; K12—rate at which drug enters tissue compartment from the central compartment; K21—rate at which drug enters central compartment from tissue compartment; V1—volume of distribution of the central compartment; V2—volume of distribution of the tissue compartment; Vss—volume of distribution at steady state; and Cl—clearance.

TABLE 4

Pharmacokinetic parameters for (R,R)-fenoterol, (R,R)-methoxyfenoterol and (R,S)-naphtylfenoterol after intravenous administration to rats (5 mg/kg).

| Parameter | Units | (R,R)-fenoterol (n = 2) Weight 306 ± 11 | (R,R)-methoxyfenoterol (n = 5) Weight 296 ± 8 | (R,S)-naphtylfenoterol (n = 5) Weight 297 ± 10 |
|---|---|---|---|---|
| | | Two-compartment open model | | |
| A | µg/ml | 1.6300 | 4.6437 | 4.0365 |
| Alpha | 1/min | 0.0710 | 0.1982 | 0.1764 |
| B | µg/ml | 0.0577 | 0.3900 | 0.4372 |
| Beta | 1/min | 0.0086 | 0.0054 | 0.0046 |
| AUC | min*µg/ml | 29.6861 | 96.1011 | 116.88 |
| $T_{1/2}$ (K10) | min | 12.19 | 13.23 | 18.11 |
| K10 | 1/min | 0.0568 | 0.0524 | 0.0383 |
| K12 | 1/min | 0.0119 | 0.1309 | 0.1213 |
| K21 | 1/min | 0.0107 | 0.0203 | 0.0214 |
| V1 | ml | 906.5 | 294.01 | 330.83 |
| V2 | ml | 1005.20 | 1895.00 | 1872.92 |
| Vss | ml | 1911.70 | 2189.02 | 2203.75 |
| Cl | ml/min | 51.54 | 15.40 | 12.66 |

Figure 8:
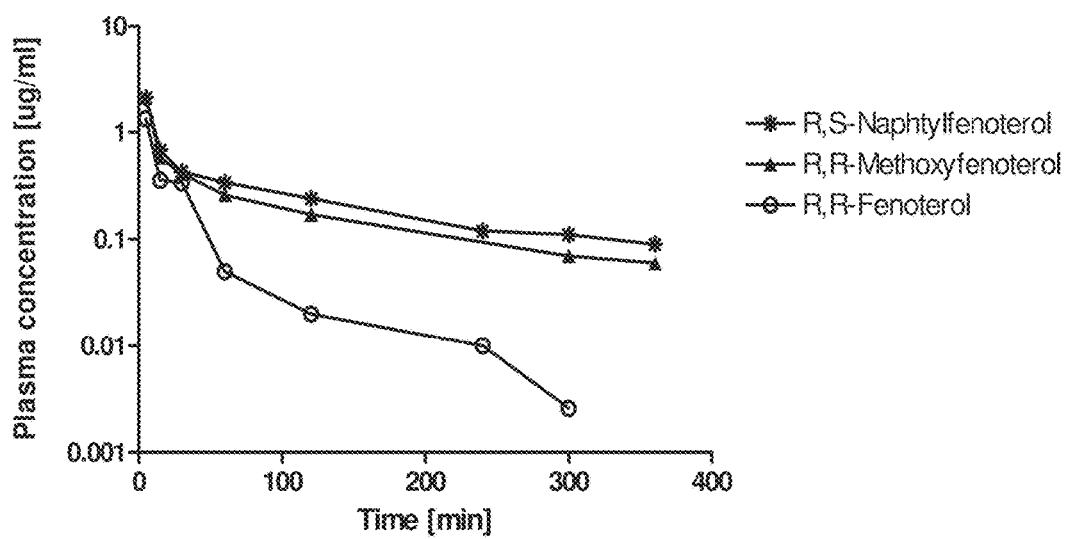
FIG. 8 is a graph illustrating time-dependent mean plasma concentration of (R,R)-fenoterol, (R,R)-methoxyfenoterol and (R,S)-napthylfenoterol after administration (5 mg/mL).

Tables 5-7 and FIG. 8 illustrate the individual plasma concentrations of (R,R)-fenoterol, (R,R)-methoxyfenoterol and (R,S)-naphtylfenoterol after IV administration to rats (5 mg/kg). The average concentration of (R,R)-fenoterol in plasma was dramatically lower (1.34 µg/ml) five minutes after IV administration to rats (5 mg/kg) compared to either the average concentration of (R,R)-methoxyfenoterol (2.12 µg/ml) or (R,S)-naphtylfenoterol (2.11 µg/ml).

TABLE 5

Individual plasma concentrations of (R,R)-fenoterol after intravenous administration (5 mg/kg).

| | Concentration (µg/ml) | | |
|---|---|---|---|
| Time (min) | Rat# 01 | Rat #02 | Average |
| 5 | | 1.34 | 1.34 |
| 15 | | 0.36 | 0.36 |
| 30 | 0.17 | 0.50 | 0.34 |
| 60 | 0.05 | 0.05 | 0.05 |
| 120 | 0.03 | 0.01 | 0.02 |
| 240 | 0.0003 | 0.02 | 0.01 |
| 300 | | 0.005 | 0.005 |
| 360 | 0.08 | 0.03 | 0.06 |

TABLE 6

Individual plasma concentrations of (R,R)-methoxyfenoterol after intravenous administration (5 mg/kg).

| | Concentration (µg/ml) | | | | | |
|---|---|---|---|---|---|---|
| Time (min) | Rat# 13 | Rat# 14 | Rat# 15 | Rat# 16 | Rat# 18 | Average |
| 5 | 1.94 | | 2.14 | 2.51 | 1.89 | 2.12 |
| 15 | 0.48 | 0.54 | 0.62 | 0.67 | 0.56 | 0.58 |
| 30 | 0.31 | 0.40 | 0.46 | 0.48 | 0.38 | 0.41 |
| 60 | 0.23 | 0.25 | 0.24 | 0.33 | 0.25 | 0.26 |
| 120 | 0.14 | 0.16 | 0.18 | 0.21 | 0.14 | 0.17 |
| 240 | 0.09 | 0.12 | 0.17 | 0.14 | 0.08 | 0.12 |
| 300 | 0.06 | 0.07 | 0.07 | 0.09 | 0.07 | 0.07 |
| 360 | 0.05 | 0.06 | 0.05 | 0.08 | 0.04 | 0.06 |

TABLE 7

Individual plasma concentrations of (R,S)-naphtylfenoterol after intravenous administration (5 mg/kg).

| | Concentration (µg/ml) | | | | | |
|---|---|---|---|---|---|---|
| Time (min) | Rat# 25 | Rat# 26 | Rat# 27 | Rat# 28 | Rat# 29 | Average |
| 5 | | 2.52 | 2.16 | 1.64 | 2.10 | 2.11 |
| 15 | | 0.85 | 0.78 | 0.50 | 0.60 | 0.68 |
| 30 | 0.49 | | 0.54 | 0.34 | 0.33 | 0.43 |
| 60 | 0.36 | 0.42 | 0.37 | 0.29 | 0.24 | 0.34 |
| 120 | 0.25 | 0.29 | 0.26 | 0.22 | 0.18 | 0.24 |
| 240 | 0.11 | 0.11 | 0.13 | 0.13 | 0.11 | 0.12 |
| 300 | 0.10 | 0.11 | 0.12 | 0.11 | 0.10 | 0.11 |
| 360 | 0.08 | 0.08 | 0.11 | 0.10 | 0.09 | 0.09 |

The data demonstrate that the two derivatives, (R,R)-methoxyfenoterol and (R,S)-naphtylfenoterol, have a significantly higher systemic exposure (AUC) and longer clearance compared to (R,R)-fenoterol which may produce a longer acting drug. It is suggested that the longer clearance time may be the result of inhibiting glucuronidation.

Example 10

Treatment of Cardiac Disorders with (R,R)-Fenoterol or Fenoterol Analogues

Based upon the teaching disclosed herein, a cardiac disorder such as congestive heart failure is treated by administering a therapeutic effective dose of (R,R)-fenoterol or one or more of the fenoterol analogues disclosed above (see Sections III and IV). In an example, a subject who has been diagnosed with congestive heart failure is identified. Following subject selection, a therapeutic effective dose of (R,R)-fenoterol or the respective fenoterol analogue is administered to the subject. For example, a therapeutic effective dose of the (R,R)-fenoterol analogue including a $OCH_3$ group or a naphthyl derivative is administered to the subject. In a further example, a therapeutic effective dose of the (R,S)-fenoterol analogue including a napthyl derivative is administered to the subject. The fenoterol analogue is prepared and purified as described in Section III.B and Example 5. The amount of (R,R)-fenoterol or fenoterol analogue or a pharmaceutical composition thereof administered to reduce, inhibit, and/or treat congestive heart failure depends on the subject being treated, the severity of the disorder, and the manner of administration of the therapeutic composition (see Section V). Ideally, a therapeutically effective amount of an agent is the amount sufficient to prevent, reduce, and/or inhibit, and/or treat the cardiac disorder (e.g., congestive heart failure) in a subject without causing a substantial cytotoxic effect in the subject.

In an example, (R,R)-fenoterol, a disclosed fenoterol analogue (such as an (R,R)-fenoterol analogue including a $OCH_3$ group or a naphthyl derivative or an (R,S)-fenoterol analogue including a napthyl derivative) or pharmaceutical composition is provided at a dosage range from about 0.001 to about 10 mg/kg body weight orally in single or divided doses. In particular examples, the dosage range is from about 0.005 to about 5 mg/kg body weight orally in single or divided doses (assuming an average body weight of approximately 70 kg; values adjusted accordingly for persons weighing more or less than average).

In certain examples, a disclosed fenoterol compound or pharmaceutical composition is provided by oral administration in the form of a tablet containing from about 1.0 to about 50 mg of the active ingredient, particularly about 2.0 mg to about 10 mg, more particularly about 2.5 mg, about 5 mg, or about 10 mg of the active ingredient for the symptomatic adjustment of the dosage to the subject being treated. In one exemplary oral dosage regimen, a tablet containing from about 1 mg to about 50 mg active ingredient is administered two to four times a day. For example, a tablet containing about 1 mg to about 10 mg active ingredient is administered two times a day.

Example 11

Treatment of Pulmonary Disorders with Fenoterol Analogues

According to the teachings herein, a pulmonary disorder such as asthma or chronic obstructive pulmonary disease is treated by administering a therapeutic effective dose of the fenoterol analogues disclosed above (see Sections III-V). In an example, a subject who has been diagnosed with or displays one of the symptoms associated with asthma or chronic obstructive pulmonary disease is identified. Following subject selection, a therapeutic effective dose of the desired fenoterol analogue is administered to the subject. For example, a therapeutic effective dose of the (R,R)-fenoterol analogue including a $OCH_3$ group or a naphthyl derivative is administered to the subject. In a further example, a therapeutic effective dose of the (R,S)-fenoterol analogue including a napthyl derivative is administered to the subject. The fenoterol analogue is prepared and purified as described in Section III.B and Example 5. The amount of the fenoterol analogue administered to prevent, reduce, inhibit, and/or treat the pulmonary disorder depends on the subject being treated, the severity of the disorder, and the manner of administration of the therapeutic composition. Ideally, a therapeutically effective amount of an agent will be the amount sufficient to prevent, reduce, and/or inhibit, and/or treat the pulmonary disorder in a subject without causing a substantial cytotoxic effect in the subject.

In an example, (R,R)-fenoterol, a disclosed fenoterol analogue (such as an (R,R)-fenoterol analogue including a $OCH_3$ group or a naphthyl derivative or an (R,S)-fenoterol analogue including a napthyl derivative) or pharmaceutical composition is provided at a dosage range from about 0.001 to about 10 mg/kg body weight orally in single or divided doses. In particular examples, the dosage range is from about 0.005 to about 5 mg/kg body weight orally in single or divided doses (assuming an average body weight of approximately 70 kg; values adjusted accordingly for persons weighing more or less than average).

In certain examples, a disclosed fenoterol compound or pharmaceutical composition is provided by oral administration in the form of a tablet containing from about 1.0 to about 50 mg of the active ingredient, particularly about 2.0 mg to about 10 mg, more particularly about 2.5 mg, about 5 mg, or about 10 mg of the active ingredient for the symptomatic adjustment of the dosage to the subject being treated. In one exemplary oral dosage regimen, a tablet containing from about 1 mg to about 50 mg active ingredient is administered two to four times a day. For example, a tablet containing about 1 mg to about 10 mg active ingredient is administered two times a day.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating congestive heart failure in a subject, comprising:
   administering to the subject with the cardiovascular disorder a therapeutically effective amount of a compound having the formula

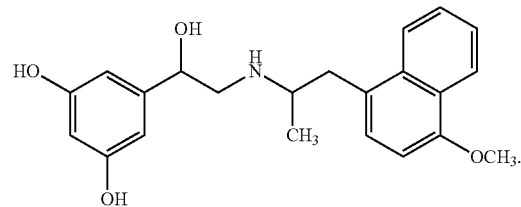 [SMILES: COc1ccc(CC(C)NCC(O)c2cc(O)cc(O)c2)c2ccccc12]

2. The method of claim 1, wherein the compound is

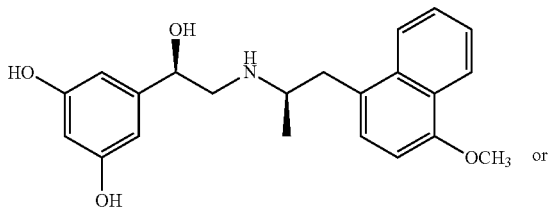
or

-continued

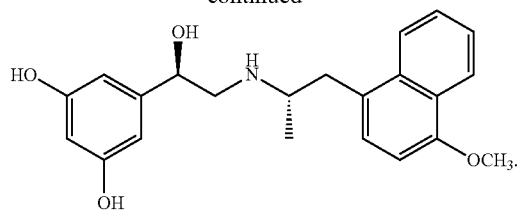

3. The method of claim 1, wherein administering a therapeutically effective amount of the compound comprises administering a pharmaceutical composition comprising the therapeutically effective amount of the compound and at least one pharmaceutically acceptable carrier.

4. The method of claim 1, wherein administering the therapeutically effective amount of the compound to the subject increases cardiomyocyte contractility.

\* \* \* \* \*